United States Patent
Hosokawa et al.

(10) Patent No.: US 7,396,915 B2
(45) Date of Patent: Jul. 8, 2008

(54) MONOCLONAL ANTIBODY AND GENE ENCODING THE SAME, HYBRIDOMA, PHARMACEUTICAL COMPOSITION, AND DIAGNOSTIC REAGENT

(75) Inventors: Saiko Hosokawa, Tokyo (JP); Masahiko Aoki, Tokyo (JP); Yoko Hirakawa, Tokyo (JP); Seima Itami, Tokyo (JP); Hiroe Umeki, Tokyo (JP); Yoshiro Saikawa, Tokyo (JP); Koichiro Kumai, Tokyo (JP); Kazumasa Fukuda, Tokyo (JP)

(73) Assignees: Mitsubishi Pharma Corporation, Osaka (JP); Keio University, Tokyo (JP)

( * ) Notice: Subject to any disclaimer, the term of this patent is extended or adjusted under 35 U.S.C. 154(b) by 358 days.

(21) Appl. No.: 10/546,594

(22) PCT Filed: Feb. 27, 2004

(86) PCT No.: PCT/JP2004/002402

§ 371 (c)(1),
(2), (4) Date: Aug. 19, 2005

(87) PCT Pub. No.: WO2004/076658

PCT Pub. Date: Sep. 10, 2004

(65) Prior Publication Data

US 2006/0088538 A1 Apr. 27, 2006

(30) Foreign Application Priority Data

Feb. 28, 2003 (JP) .............................. 2003-054670
Jul. 9, 2003 (JP) .............................. 2003-194643

(51) Int. Cl.
*C07K 16/00* (2006.01)
(52) U.S. Cl. .................. 530/387.7; 530/350; 536/23.1; 536/23.53; 435/252.3; 435/320.1; 435/325
(58) Field of Classification Search ................ 530/350, 530/387.1, 387.3, 387.7; 424/130.1, 9.341; 536/23.1, 23.53; 435/320.1, 325, 326, 252.3
See application file for complete search history.

(56) References Cited

U.S. PATENT DOCUMENTS 4,727,021 A * 2/1988 Cote et al.

FOREIGN PATENT DOCUMENTS

| GB | 2 378 949 A | 2/2003 |
| WO | WO 98/55619 A1 | 12/1998 |
| WO | WO 01/55437 A2 | 8/2001 |
| WO | WO 02/02641 A1 | 1/2002 |
| WO | WO 03/016354 A2 | 2/2003 |

OTHER PUBLICATIONS

Mariuzza et al. (Annu. Rev. Biophys. Biophys. Chem. 1987; 16: 139-159).*
Giusti et al. (PNAS, 84(9): 2926-2930, 1987).*
Rudikoff et al (PNAS, 79:1979-1983, 1982).*
Aoki et al (Anticancer Research, 25:3791-3798, 2005).*
Hudziak et al (MCB, 9(3):1165-1172, 1989).*
Hagiwara et al (Human Antibodies, 10:77-82, 2001).*
Thorpe (B. J. Haem., 76:116-120, 1990).*
Dellagi et al (PNAS, 79:446-450, 1982).*
Huber et al., *Eur. J. Immunol*, 23: 2868-2875 (1993).
Rittling et al., *Molecular and Cellular Biology*, 7(11): 3908-3915 (Nov. 1987).

* cited by examiner

*Primary Examiner*—Stephen L. Rawlings
*Assistant Examiner*—Brad Duffy
(74) *Attorney, Agent, or Firm*—Leydig, Voit & Mayer, Ltd.

(57) ABSTRACT

A novel human monoclonal antibody specifically recognizing cancer cells such as non-small cell lung cancer, pancreatic cancer and gastric cancer cells is produced by hybridomas which are obtained by fusing lymphocytes derived from a cancer tissue of a cancer patient with mouse myeloma cells. An anti-cancer drug is obtained by using the antibody alone or anchoring the antibody on the surface of a liposome containing a toxin or an anti-cancer drug encapsulated therein. More specifically, an anti-cancer drug is obtained by using an antibody, in which variable region of its heavy chain comprises the amino acid sequence of SEQ ID NO: 115 and variable region of the light chain comprises the amino acid sequence of SEQ ID NO: 117, alone or anchoring the antibody on the surface of a liposome containing a toxin or an anti-cancer drug encapsulated therein.

16 Claims, 9 Drawing Sheets autologous lung noncancerous tissue autologous lung cancer tissue

HLC-1

A549

SUIT2

PANC-1

PK8

MKN45

SEQUENCE LISTING

```
<160> NUMBER OF SEQ ID NOS: 132

<210> SEQ ID NO 1
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 1 cag gtg cag ctg gtg cag tct gg                                         23
Gln Val Gln Leu Val Gln Ser
1               5

<210> SEQ ID NO 2
<211> LENGTH: 7
<212> TYPE: PRT
<213> ORGANISM: Homo sapiens

<400> SEQUENCE: 2

Gln Val Gln Leu Val Gln Ser
1               5

<210> SEQ ID NO 3
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 3 cag gtc aac tta agg gag tct gg                                         23
Gln Val Asn Leu Arg Glu Ser
1               5

<210> SEQ ID NO 4
<211> LENGTH: 7
<212> TYPE: PRT
<213> ORGANISM: Homo sapiens

<400> SEQUENCE: 4

Gln Val Asn Leu Arg Glu Ser
1               5

<210> SEQ ID NO 5
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
```

```
<223> OTHER INFORMATION:

<400> SEQUENCE: 5 gag gtg cag ctg gtg gag tct gg                                            23
Glu Val Gln Leu Val Glu Ser
1               5

<210> SEQ ID NO 6
<211> LENGTH: 7
<212> TYPE: PRT
<213> ORGANISM: Homo sapiens

<400> SEQUENCE: 6

Glu Val Gln Leu Val Glu Ser
1               5

<210> SEQ ID NO 7
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 7 cag gtg cag ctg cag gag tcg gg                                            23
Gln Val Gln Leu Gln Glu Ser
1               5

<210> SEQ ID NO 8
<211> LENGTH: 7
<212> TYPE: PRT
<213> ORGANISM: Homo sapiens

<400> SEQUENCE: 8

Gln Val Gln Leu Gln Glu Ser
1               5

<210> SEQ ID NO 9
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 9 gag gtg cag ctg ttg cag tct gc                                            23
Glu Val Gln Leu Leu Gln Ser
1               5

<210> SEQ ID NO 10
<211> LENGTH: 7
<212> TYPE: PRT
<213> ORGANISM: Homo sapiens

<400> SEQUENCE: 10

Glu Val Gln Leu Leu Gln Ser
1               5

<210> SEQ ID NO 11
```

```
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 11 cag gta cag ctg cag cag tca gg                                          23
Gln Val Gln Leu Gln Gln Ser
1               5

<210> SEQ ID NO 12
<211> LENGTH: 7
<212> TYPE: PRT
<213> ORGANISM: Homo sapiens

<400> SEQUENCE: 12

Gln Val Gln Leu Gln Gln Ser
1               5

<210> SEQ ID NO 13
<211> LENGTH: 24
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(24)
<223> OTHER INFORMATION:

<400> SEQUENCE: 13 ggc acc ctg gtc acc gtc tcc tca                                         24
Gly Thr Leu Val Thr Val Ser Ser
1               5

<210> SEQ ID NO 14
<211> LENGTH: 8
<212> TYPE: PRT
<213> ORGANISM: Homo sapiens

<400> SEQUENCE: 14

Gly Thr Leu Val Thr Val Ser Ser
1               5

<210> SEQ ID NO 15
<211> LENGTH: 24
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(24)
<223> OTHER INFORMATION:

<400> SEQUENCE: 15 ggg aca atg gtc acc gtc tct tca                                         24
Gly Thr Met Val Thr Val Ser Ser
1               5

<210> SEQ ID NO 16
<211> LENGTH: 8
<212> TYPE: PRT
<213> ORGANISM: Homo sapiens
```

```
<400> SEQUENCE: 16

Gly Thr Met Val Thr Val Ser Ser
1               5

<210> SEQ ID NO 17
<211> LENGTH: 24
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(24)
<223> OTHER INFORMATION:

<400> SEQUENCE: 17 gga acc ctg gtc acc gtc tcc tca                                    24
Gly Thr Leu Val Thr Val Ser Ser
1               5

<210> SEQ ID NO 18
<211> LENGTH: 8
<212> TYPE: PRT
<213> ORGANISM: Homo sapiens

<400> SEQUENCE: 18

Gly Thr Leu Val Thr Val Ser Ser
1               5

<210> SEQ ID NO 19
<211> LENGTH: 24
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(24)
<223> OTHER INFORMATION:

<400> SEQUENCE: 19 ggg acc acg gtc acc gtc tcc tca                                    24
Gly Thr Thr Val Thr Val Ser Ser
1               5

<210> SEQ ID NO 20
<211> LENGTH: 8
<212> TYPE: PRT
<213> ORGANISM: Homo sapiens

<400> SEQUENCE: 20

Gly Thr Thr Val Thr Val Ser Ser
1               5

<210> SEQ ID NO 21
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 21 gac atc cag atg acc cag tct cc                                     23
```

```
Asp Ile Gln Met Thr Gln Ser
1               5

<210> SEQ ID NO 22
<211> LENGTH: 7
<212> TYPE: PRT
<213> ORGANISM: Homo sapiens

<400> SEQUENCE: 22

Asp Ile Gln Met Thr Gln Ser
1               5

<210> SEQ ID NO 23
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 23 gat gtt gtg atg act cag tct cc                                      23
Asp Val Val Met Thr Gln Ser
1               5

<210> SEQ ID NO 24
<211> LENGTH: 7
<212> TYPE: PRT
<213> ORGANISM: Homo sapiens

<400> SEQUENCE: 24

Asp Val Val Met Thr Gln Ser
1               5

<210> SEQ ID NO 25
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 25 gaa att gtg ttg acg cag tct cc                                      23
Glu Ile Val Leu Thr Gln Ser
1               5

<210> SEQ ID NO 26
<211> LENGTH: 7
<212> TYPE: PRT
<213> ORGANISM: Homo sapiens

<400> SEQUENCE: 26

Glu Ile Val Leu Thr Gln Ser
1               5

<210> SEQ ID NO 27
<211> LENGTH: 23
<212> TYPE: DNA
<213> ORGANISM: Homo sapiens
<220> FEATURE:
<223> OTHER INFORMATION: primer
```

```
<220> FEATURE:
<221> NAME/KEY: CDS
<222> LOCATION: (1)..(21)
<223> OTHER INFORMATION:

<400> SEQUENCE: 27 gac atc gtg atg acc cag tct cc                                          23
Asp Ile Val Met Thr Gln Ser
1               5

<210> SEQ ID NO 28
<211> LENGTH: 7
<212> TYPE: PRT
<213> ORGANISM: Homo sapiens

<400> SEQUENCE: 28

Asp Ile Val Met Thr Gln Ser
1               5

<210> SEQ ID NO 29
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 29 gaa acg aca ctc acg cag tct cc                                          23
Glu Thr Thr Leu Thr Gln Ser
1               5

<210> SEQ ID NO 30
<211> LENGTH: 7
<212> TYPE: PRT
<213> ORGANISM: Homo sapiens

<400> SEQUENCE: 30

Glu Thr Thr Leu Thr Gln Ser
1               5

<210> SEQ ID NO 31
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 31 gaa att gtg ctg act cag tct cc                                          23
Glu Ile Val Leu Thr Gln Ser
1               5

<210> SEQ ID NO 32
<211> LENGTH: 7
<212> TYPE: PRT
<213> ORGANISM: Homo sapiens

<400> SEQUENCE: 32

Glu Ile Val Leu Thr Gln Ser
1               5
```

```
<210> SEQ ID NO 33
<211> LENGTH: 24
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(24)
<223> OTHER INFORMATION:

<400> SEQUENCE: 33 ggg acc aag gtg gaa atc aaa cgt                              24
Gly Thr Lys Val Glu Ile Lys Arg
1               5

<210> SEQ ID NO 34
<211> LENGTH: 8
<212> TYPE: PRT
<213> ORGANISM: Homo sapiens

<400> SEQUENCE: 34

Gly Thr Lys Val Glu Ile Lys Arg
1               5

<210> SEQ ID NO 35
<211> LENGTH: 24
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(24)
<223> OTHER INFORMATION:

<400> SEQUENCE: 35 ggg acc aag ctg gag atc aaa cgt                              24
Gly Thr Lys Leu Glu Ile Lys Arg
1               5

<210> SEQ ID NO 36
<211> LENGTH: 8
<212> TYPE: PRT
<213> ORGANISM: Homo sapiens

<400> SEQUENCE: 36

Gly Thr Lys Leu Glu Ile Lys Arg
1               5

<210> SEQ ID NO 37
<211> LENGTH: 24
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(24)
<223> OTHER INFORMATION:

<400> SEQUENCE: 37 ggg acc aaa gtg gat atc aaa cgt                              24
Gly Thr Lys Val Asp Ile Lys Arg
1               5

<210> SEQ ID NO 38
```

```
<211> LENGTH: 8
<212> TYPE: PRT
<213> ORGANISM: Homo sapiens

<400> SEQUENCE: 38

Gly Thr Lys Val Asp Ile Lys Arg
1               5

<210> SEQ ID NO 39
<211> LENGTH: 24
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(24)
<223> OTHER INFORMATION:

<400> SEQUENCE: 39 ggg acc aag gtg gag atc aaa cgt                                        24
Gly Thr Lys Val Glu Ile Lys Arg
1               5

<210> SEQ ID NO 40
<211> LENGTH: 8
<212> TYPE: PRT
<213> ORGANISM: Homo sapiens

<400> SEQUENCE: 40

Gly Thr Lys Val Glu Ile Lys Arg
1               5

<210> SEQ ID NO 41
<211> LENGTH: 24
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(24)
<223> OTHER INFORMATION:

<400> SEQUENCE: 41 ggg aca cga ctg gag att aaa cgt                                        24
Gly Thr Arg Leu Glu Ile Lys Arg
1               5

<210> SEQ ID NO 42
<211> LENGTH: 8
<212> TYPE: PRT
<213> ORGANISM: Homo sapiens

<400> SEQUENCE: 42

Gly Thr Arg Leu Glu Ile Lys Arg
1               5

<210> SEQ ID NO 43
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:
```

```
<400> SEQUENCE: 43 cag tct gtg ttg acg cag ccg cc                                    23
Gln Ser Val Leu Thr Gln Pro
1               5

<210> SEQ ID NO 44
<211> LENGTH: 7
<212> TYPE: PRT
<213> ORGANISM: Homo sapiens

<400> SEQUENCE: 44

Gln Ser Val Leu Thr Gln Pro
1               5

<210> SEQ ID NO 45
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 45 cag tct gcc ctg act cag cct gc                                    23
Gln Ser Ala Leu Thr Gln Pro
1               5

<210> SEQ ID NO 46
<211> LENGTH: 7
<212> TYPE: PRT
<213> ORGANISM: Homo sapiens

<400> SEQUENCE: 46

Gln Ser Ala Leu Thr Gln Pro
1               5

<210> SEQ ID NO 47
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 47 tcc tat gtg ctg act cag cca cc                                    23
Ser Tyr Val Leu Thr Gln Pro
1               5

<210> SEQ ID NO 48
<211> LENGTH: 7
<212> TYPE: PRT
<213> ORGANISM: Homo sapiens

<400> SEQUENCE: 48

Ser Tyr Val Leu Thr Gln Pro
1               5

<210> SEQ ID NO 49
<211> LENGTH: 23
<212> TYPE: DNA
```

```
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 49 tct tct gag ctg act cag gac cc                                          23
Ser Ser Glu Leu Thr Gln Asp
1               5

<210> SEQ ID NO 50
<211> LENGTH: 7
<212> TYPE: PRT
<213> ORGANISM: Homo sapiens

<400> SEQUENCE: 50

Ser Ser Glu Leu Thr Gln Asp
1               5

<210> SEQ ID NO 51
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 51 cac gtt ata ctg act caa ccg cc                                          23
His Val Ile Leu Thr Gln Pro
1               5

<210> SEQ ID NO 52
<211> LENGTH: 7
<212> TYPE: PRT
<213> ORGANISM: Homo sapiens

<400> SEQUENCE: 52

His Val Ile Leu Thr Gln Pro
1               5

<210> SEQ ID NO 53
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 53 cag gct gtg ctc act cag ccg tc                                          23
Gln Ala Val Leu Thr Gln Pro
1               5

<210> SEQ ID NO 54
<211> LENGTH: 7
<212> TYPE: PRT
<213> ORGANISM: Homo sapiens

<400> SEQUENCE: 54
```

```
Gln Ala Val Leu Thr Gln Pro
1               5

<210> SEQ ID NO 55
<211> LENGTH: 23
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(21)
<223> OTHER INFORMATION:

<400> SEQUENCE: 55 aat ttt atg ctg act cag ccc ca                              23
Asn Phe Met Leu Thr Gln Pro
1               5

<210> SEQ ID NO 56
<211> LENGTH: 7
<212> TYPE: PRT
<213> ORGANISM: Homo sapiens

<400> SEQUENCE: 56

Asn Phe Met Leu Thr Gln Pro
1               5

<210> SEQ ID NO 57
<211> LENGTH: 24
<212> TYPE: DNA
<213> ORGANISM: Homo sapiens
<220> FEATURE:
<223> OTHER INFORMATION: Homo sapiens
<220> FEATURE:
<221> NAME/KEY: CDS
<222> LOCATION: (1)..(24)
<223> OTHER INFORMATION:

<400> SEQUENCE: 57 ggg acc aag gtc acc gtc cta ggt                             24
Gly Thr Lys Val Thr Val Leu Gly
1               5

<210> SEQ ID NO 58
<211> LENGTH: 8
<212> TYPE: PRT
<213> ORGANISM: Homo sapiens

<400> SEQUENCE: 58

Gly Thr Lys Val Thr Val Leu Gly
1               5

<210> SEQ ID NO 59
<211> LENGTH: 24
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(24)
<223> OTHER INFORMATION:

<400> SEQUENCE: 59 ggg acc aag ctg acc gtc cta ggt                             24
Gly Thr Lys Leu Thr Val Leu Gly
1               5
```

```
<210> SEQ ID NO 60
<211> LENGTH: 8
<212> TYPE: PRT
<213> ORGANISM: Homo sapiens

<400> SEQUENCE: 60

Gly Thr Lys Leu Thr Val Leu Gly
1               5

<210> SEQ ID NO 61
<211> LENGTH: 24
<212> TYPE: DNA
<213> ORGANISM: Homo sapiens
<220> FEATURE:
<223> OTHER INFORMATION: primer
<220> FEATURE:
<221> NAME/KEY: CDS
<222> LOCATION: (1)..(24)
<223> OTHER INFORMATION:

<400> SEQUENCE: 61 ggg acc cag ctc acc gtt tta ggt                                          24
Gly Thr Gln Leu Thr Val Leu Gly
1               5

<210> SEQ ID NO 62
<211> LENGTH: 8
<212> TYPE: PRT
<213> ORGANISM: Homo sapiens

<400> SEQUENCE: 62

Gly Thr Gln Leu Thr Val Leu Gly
1               5

<210> SEQ ID NO 63
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION:

<400> SEQUENCE: 63 gag gtg cag ctg gtg gag tct ggg gga ggc gtg gtc cag cct ggg agg        48
Glu Val Gln Leu Val Glu Ser Gly Gly Gly Val Val Gln Pro Gly Arg
1               5                   10                  15 tcc ctg aga ctc tcc tgt gca gcc tct gga ttc acc ttc agt agc tat        96
Ser Leu Arg Leu Ser Cys Ala Ala Ser Gly Phe Thr Phe Ser Ser Tyr
            20                  25                  30 gct atg cac tgg gtc cgc cag gct cca ggc aag ggg ctg gag tgg gtg       144
Ala Met His Trp Val Arg Gln Ala Pro Gly Lys Gly Leu Glu Trp Val
        35                  40                  45 gca gtt ata tca tat gat gga agc aat aaa tac tac gca gac tcc gtg       192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat       240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt       288
Leu Gln Met Asn Ser Leu Arg Ala Glu Asp Thr Ala Val Tyr Tyr Cys
                85                  90                  95 gcg aga gat cgg cac tcc tac gat ttt tgg agt ggg tcc ctt gac tac       336
Ala Arg Asp Arg His Ser Tyr Asp Phe Trp Ser Gly Ser Leu Asp Tyr
```

```
                    100                 105                 110
tgg ggc cag ggc acc ctg gtc acc gtc tcc tca                        369
Trp Gly Gln Gly Thr Leu Val Thr Val Ser Ser
        115                 120

<210> SEQ ID NO 64
<211> LENGTH: 123
<212> TYPE: PRT
<213> ORGANISM: Homo sapiens

<400> SEQUENCE: 64

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg His Ser Tyr Asp Phe Trp Ser Gly Ser Leu Asp Tyr
            100                 105                 110

Trp Gly Gln Gly Thr Leu Val Thr Val Ser Ser
        115                 120

<210> SEQ ID NO 65
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION:

<400> SEQUENCE: 65 cag gtg cag ctg gtg cag tct ggg gga ggc gtg gtc cag cct ggg agg    48
Gln Val Gln Leu Val Gln Ser Gly Gly Gly Val Val Gln Pro Gly Arg
1               5                   10                  15 tcc ctg aga ctc tcc tgt gca gcc tct gga ttc acc ttc agt agc tat    96
Ser Leu Arg Leu Ser Cys Ala Ala Ser Gly Phe Thr Phe Ser Ser Tyr
            20                  25                  30 gct atg cac tgg gtc cgc cag gct cca ggc aag ggg ctg gag tgg gtg   144
Ala Met His Trp Val Arg Gln Ala Pro Gly Lys Gly Leu Glu Trp Val
        35                  40                  45 gca gtt ata tca tat gat gga agc aat aaa tac tac gca gac tcc gtg   192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat   240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt   288
Leu Gln Met Asn Ser Leu Arg Ala Glu Asp Thr Ala Val Tyr Tyr Cys
                85                  90                  95 gcg aga gat cgg cac tcc tac gat ttt tgg agt ggg tcc ctt gac tac   336
Ala Arg Asp Arg His Ser Tyr Asp Phe Trp Ser Gly Ser Leu Asp Tyr
            100                 105                 110 tgg ggc cag gga acc ctg gtc acc gtc tcc tca                       369
```

<210> SEQ ID NO 66
<211> LENGTH: 123
<212> TYPE: PRT
<213> ORGANISM: Homo sapiens

<400> SEQUENCE: 66

```
Gln Val Gln Leu Val Gln Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Ala Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Asp Arg His Ser Tyr Asp Phe Trp Ser Gly Ser Leu Asp Tyr
            100                 105                 110
Trp Gly Gln Gly Thr Leu Val Thr Val Ser Ser
        115                 120
```

<210> SEQ ID NO 67
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION:

<400> SEQUENCE: 67

```
cag gtg cag ctg gtg cag tct ggg gga ggc gtg gtc cag cct ggg agg    48
Gln Val Gln Leu Val Gln Ser Gly Gly Gly Val Val Gln Pro Gly Arg
1               5                   10                  15 tcc ctg aga ctc tcc tat gca gcc tct gga ttc acc ttc agt agc tat    96
Ser Leu Arg Leu Ser Tyr Ala Ala Ser Gly Phe Thr Phe Ser Ser Tyr
            20                  25                  30 gct atg cac tgg gtc cgc cag gct cca ggc aag ggg ctg gag tgg gtg   144
Ala Met His Trp Val Arg Gln Ala Pro Gly Lys Gly Leu Glu Trp Val
        35                  40                  45 gca gtt ata tca tat gat gga agc aat aaa tgc tac gca gac tcc gtg   192
Ala Val Ile Ser Tyr Asp Gly Ser Asn Lys Cys Tyr Ala Asp Ser Val
    50                  55                  60 aag ggc cga ttc acc atc tcc aga gac aat tcc aag aac acg ctg tat   240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt   288
Leu Gln Met Asn Ser Leu Arg Ala Glu Asp Thr Ala Val Tyr Tyr Cys
                85                  90                  95 gcg aga gat cgg cac tcc tac gat ttt tgg agt ggg tcc ctt gac tac   336
Ala Arg Asp Arg His Ser Tyr Asp Phe Trp Ser Gly Ser Leu Asp Tyr
            100                 105                 110 tgg ggc cag gga acc ctg gtc acc gtc tcc tca                       369
Trp Gly Gln Gly Thr Leu Val Thr Val Ser Ser
        115                 120
```

<210> SEQ ID NO 68
<211> LENGTH: 123
<212> TYPE: PRT
<213> ORGANISM: Homo sapiens

<400> SEQUENCE: 68

```
Gln Val Gln Leu Val Gln Ser Gly Gly Gly Val Val Gln Pro Gly Arg
1               5                   10                  15

Ser Leu Arg Leu Ser Tyr Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Cys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg His Ser Tyr Asp Phe Trp Ser Gly Ser Leu Asp Tyr
            100                 105                 110

Trp Gly Gln Gly Thr Leu Val Thr Val Ser Ser
        115                 120
```

<210> SEQ ID NO 69
<211> LENGTH: 369
<212> TYPE: DNA
<213> ORGANISM: Homo sapiens
<220> FEATURE:
<221> NAME/KEY: CDS
<222> LOCATION: (1)..(369)
<223> OTHER INFORMATION:

<400> SEQUENCE: 69

```
gag gtg cag ctg gtg gag tct ggg gga ggc gtg gtc cag cct ggg agg        48
Glu Val Gln Leu Val Glu Ser Gly Gly Gly Val Val Gln Pro Gly Arg
1               5                   10                  15 tcc ctg aga ctc tcc tgt gca gcc tct gga ttc acc ttc agt agc tat        96
Ser Leu Arg Leu Ser Cys Ala Ala Ser Gly Phe Thr Phe Ser Ser Tyr
            20                  25                  30 gct atg cac tgg gtc cgc cag gct cca ggc aag ggg ctg gag tgg gtg       144
Ala Met His Trp Val Arg Gln Ala Pro Gly Lys Gly Leu Glu Trp Val
        35                  40                  45 gca gtt ata tca tat gat gga agc aat aaa tac tac gca gac tcc gtg       192
Ala Val Ile Ser Tyr Asp Gly Ser Asn Lys Tyr Tyr Ala Asp Ser Val
    50                  55                  60 aag ggc cga ttc acc atc tcc aga gac aat tcc aag aac acg ctg tat       240
Lys Gly Arg Phe Thr Ile Ser Arg Asp Asn Ser Lys Asn Thr Leu Tyr
65                  70                  75                  80 ctg caa atg aac agc ctg aga gct gag gac acg gct gtg tat tac tgt       288
Leu Gln Met Asn Ser Leu Arg Ala Glu Asp Thr Ala Val Tyr Tyr Cys
                85                  90                  95 gcg aga gat cgg cac tcc tac gat ttt tgg agt ggg tcc ctt gac tac       336
Ala Arg Asp Arg His Ser Tyr Asp Phe Trp Ser Gly Ser Leu Asp Tyr
            100                 105                 110 tgg ggc cag gga acc ctg gtc acc gtc tcc tca                            369
Trp Gly Gln Gly Thr Leu Val Thr Val Ser Ser
        115                 120
```

<210> SEQ ID NO 70
<211> LENGTH: 123

<212> TYPE: PRT
<213> ORGANISM: Homo sapiens

<400> SEQUENCE: 70

```
Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg His Ser Tyr Asp Phe Trp Ser Gly Ser Leu Asp Tyr
            100                 105                 110

Trp Gly Gln Gly Thr Leu Val Thr Val Ser Ser
        115                 120
```

<210> SEQ ID NO 71
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION:

<400> SEQUENCE: 71

```
gac atc cag atg acc cag tct cct tcc acc ctg tct gca tct gta gga      48
Asp Ile Gln Met Thr Gln Ser Pro Ser Thr Leu Ser Ala Ser Val Gly
1               5                   10                  15 gac aga gtc acc atc act tgc cgg gcc agt cag agt att agt agc tgg      96
Asp Arg Val Thr Ile Thr Cys Arg Ala Ser Gln Ser Ile Ser Ser Trp
            20                  25                  30 ttg gcc tgg tat cag cag aaa cca ggg aaa gcc cct aag ctc ctg atc     144
Leu Ala Trp Tyr Gln Gln Lys Pro Gly Lys Ala Pro Lys Leu Leu Ile
        35                  40                  45 tat aag gca tct agt tta gaa agt ggg gtc cca tca agg ttc agc ggc     192
Tyr Lys Ala Ser Ser Leu Glu Ser Gly Val Pro Ser Arg Phe Ser Gly
    50                  55                  60 agt gga tct ggg aca gaa ttc act ctc acc atc agc agc ctg cga cct     240
Ser Gly Ser Gly Thr Glu Phe Thr Leu Thr Ile Ser Ser Leu Arg Pro
65                  70                  75                  80 gat gat ttt gca act tat tac tgc caa cag tat aat agt tat tct aac     288
Asp Asp Phe Ala Thr Tyr Tyr Cys Gln Gln Tyr Asn Ser Tyr Ser Asn
                85                  90                  95 act ttt ggc cag ggg acc aag ctg gaa atc aaa cgt                     324
Thr Phe Gly Gln Gly Thr Lys Leu Glu Ile Lys Arg
            100                 105
```

<210> SEQ ID NO 72
<211> LENGTH: 108
<212> TYPE: PRT
<213> ORGANISM: Homo sapiens

<400> SEQUENCE: 72

```
Asp Ile Gln Met Thr Gln Ser Pro Ser Thr Leu Ser Ala Ser Val Gly
1               5                   10                  15
```

```
Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Arg Pro
65                  70                  75                  80

Asp Asp Phe Ala Thr Tyr Tyr Cys Gln Gln Tyr Asn Ser Tyr Ser Asn
                85                  90                  95

Thr Phe Gly Gln Gly Thr Lys Leu Glu Ile Lys Arg
            100                 105
```

<210> SEQ ID NO 73
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION:

<400> SEQUENCE: 73

```
gac atc gtg atg acc cag tct cct tcc acc ctg tct gca tct gta gga      48
Asp Ile Val Met Thr Gln Ser Pro Ser Thr Leu Ser Ala Ser Val Gly
1               5                   10                  15 gac aga gtc acc atc act tgc cgg gcc agt cag agt att agt agc tgg      96
Asp Arg Val Thr Ile Thr Cys Arg Ala Ser Gln Ser Ile Ser Ser Trp
            20                  25                  30 ttg gcc tgg tat cag cag aaa cca ggg aaa gcc cct aag ctc ctg atc     144
Leu Ala Trp Tyr Gln Gln Lys Pro Gly Lys Ala Pro Lys Leu Leu Ile
        35                  40                  45 tat aag gca tct agt tta gaa agt ggg gtc cca tca agg ttc agc ggc     192
Tyr Lys Ala Ser Ser Leu Glu Ser Gly Val Pro Ser Arg Phe Ser Gly
    50                  55                  60 agt gga tct ggg aca gaa ttc act ctc acc atc agc agc ctg cag cct     240
Ser Gly Ser Gly Thr Glu Phe Thr Leu Thr Ile Ser Ser Leu Gln Pro
65                  70                  75                  80 gat gat ttt gca act tat tac tgc caa cag tat aat agt tat tct aac     288
Asp Asp Phe Ala Thr Tyr Tyr Cys Gln Gln Tyr Asn Ser Tyr Ser Asn
                85                  90                  95 act ttt ggc cag ggg acc aag gtg gaa atc aaa cgt                     324
Thr Phe Gly Gln Gly Thr Lys Val Glu Ile Lys Arg
            100                 105
```

<210> SEQ ID NO 74
<211> LENGTH: 108
<212> TYPE: PRT
<213> ORGANISM: Homo sapiens

<400> SEQUENCE: 74

```
Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60
```

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Asn
                 85                  90                  95

Thr Phe Gly Gln Gly Thr Lys Val Glu Ile Lys Arg
            100                 105
```

```
<210> SEQ ID NO 75
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION:

<400> SEQUENCE: 75
```

```
gac atc cag atg acc cag tct cct tcc acc ctg tct gca tct gta gga    48
Asp Ile Gln Met Thr Gln Ser Pro Ser Thr Leu Ser Ala Ser Val Gly
 1               5                  10                  15 gac aga gtc acc atc act tgc cgg gcc agt cag agt att agt agc tgg    96
Asp Arg Val Thr Ile Thr Cys Arg Ala Ser Gln Ser Ile Ser Ser Trp
             20                  25                  30 ttg gcc tgg tat cag cag aaa cca ggg aaa gcc cct aag ctc ctg atc   144
Leu Ala Trp Tyr Gln Gln Lys Pro Gly Lys Ala Pro Lys Leu Leu Ile
         35                  40                  45 tat aag gca tct agt tta gaa agt ggg gtc cca tca agg ttc agc ggc   192
Tyr Lys Ala Ser Ser Leu Glu Ser Gly Val Pro Ser Arg Phe Ser Gly
     50                  55                  60 agt gga tct ggg aca gaa ttc act ctc acc atc agc agc ctg cag cct   240
Ser Gly Ser Gly Thr Glu Phe Thr Leu Thr Ile Ser Ser Leu Gln Pro
 65                  70                  75                  80 gat gat ttt gca act tat tac tgc caa cag tat aat agt tac tct aac   288
Asp Asp Phe Ala Thr Tyr Tyr Cys Gln Gln Tyr Asn Ser Tyr Ser Asn
                 85                  90                  95 act ttt ggc cag ggg acc aag ctg gag atc aaa cgt                   324
Thr Phe Gly Gln Gly Thr Lys Leu Glu Ile Lys Arg
            100                 105
```

```
<210> SEQ ID NO 76
<211> LENGTH: 108
<212> TYPE: PRT
<213> ORGANISM: Homo sapiens

<400> SEQUENCE: 76
```

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Asn
                 85                  90                  95

Thr Phe Gly Gln Gly Thr Lys Leu Glu Ile Lys Arg
            100                 105
```

<210> SEQ ID NO 77
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION:

<400> SEQUENCE: 77

```
gac atc gtg atg acc cag tct cct tcc acc ctg tct gca tct gta gga      48
Asp Ile Val Met Thr Gln Ser Pro Ser Thr Leu Ser Ala Ser Val Gly
1               5                   10                  15 gac aga gtc acc gtc act tgc cgg gcc agt cag agt att agt agc tgg      96
Asp Arg Val Thr Val Thr Cys Arg Ala Ser Gln Ser Ile Ser Ser Trp
            20                  25                  30 ttg gcc tgg tat cag cag aaa cca ggg aaa gcc cct aag ctc ctg atc     144
Leu Ala Trp Tyr Gln Gln Lys Pro Gly Lys Ala Pro Lys Leu Leu Ile
        35                  40                  45 tat aag gca tct agt tta gaa agt ggg gtc cca tca agg ttc agc ggc     192
Tyr Lys Ala Ser Ser Leu Glu Ser Gly Val Pro Ser Arg Phe Ser Gly
    50                  55                  60 agt gga tct ggg acg gaa ttc act ctc acc atc agc agc ctg cag cct     240
Ser Gly Ser Gly Thr Glu Phe Thr Leu Thr Ile Ser Ser Leu Gln Pro
65                  70                  75                  80 gat gat ttt gca act tat tac tgc caa cag tat aat agt tat tct aac     288
Asp Asp Phe Ala Thr Tyr Tyr Cys Gln Gln Tyr Asn Ser Tyr Ser Asn
                85                  90                  95 act ttt ggc cag ggg acc aaa gtg gat atc aaa cgt                     324
Thr Phe Gly Gln Gly Thr Lys Val Asp Ile Lys Arg
            100                 105
```

<210> SEQ ID NO 78
<211> LENGTH: 108
<212> TYPE: PRT
<213> ORGANISM: Homo sapiens

<400> SEQUENCE: 78

```
Asp Ile Val Met Thr Gln Ser Pro Ser Thr Leu Ser Ala Ser Val Gly
1               5                   10                  15

Asp Arg Val Thr Val Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Asn
                85                  90                  95

Thr Phe Gly Gln Gly Thr Lys Val Asp Ile Lys Arg
            100                 105
```

<210> SEQ ID NO 79
<211> LENGTH: 324
<212> TYPE: DNA
<213> ORGANISM: Homo sapiens
<220> FEATURE:
<221> NAME/KEY: CDS
<222> LOCATION: (1)..(324)
<223> OTHER INFORMATION:

<400> SEQUENCE: 79

```
gac atc gtg atg acc cag tct cct tcc acc ctg tct gca tct gta gga      48
Asp Ile Val Met Thr Gln Ser Pro Ser Thr Leu Ser Ala Ser Val Gly
1               5                   10                  15 gac aga gtc acc atc act tgc cgg gcc agt cag agt att agt agc tgg      96
Asp Arg Val Thr Ile Thr Cys Arg Ala Ser Gln Ser Ile Ser Ser Trp
            20                  25                  30 ttg gcc tgg tat cag cag aaa cca ggg aaa gcc cct aag ctc ctg atc     144
Leu Ala Trp Tyr Gln Gln Lys Pro Gly Lys Ala Pro Lys Leu Leu Ile
        35                  40                  45 tat aag gca tct agt tta gaa agt ggg gtc cca tca agg ttc agc ggc     192
Tyr Lys Ala Ser Ser Leu Glu Ser Gly Val Pro Ser Arg Phe Ser Gly
    50                  55                  60 agt gga tct ggg aca gaa ttc act ctc acc atc agc agc ctg cag cct     240
Ser Gly Ser Gly Thr Glu Phe Thr Leu Thr Ile Ser Ser Leu Gln Pro
65                  70                  75                  80 gat gat ttt gca act tat tac tgc caa cag tat aat agt tat tct aac     288
Asp Asp Phe Ala Thr Tyr Tyr Cys Gln Gln Tyr Asn Ser Tyr Ser Asn
                85                  90                  95 act ttt ggc cag ggg acc aag ctg gag atc aaa cgt                     324
Thr Phe Gly Gln Gly Thr Lys Leu Glu Ile Lys Arg
            100                 105

<210> SEQ ID NO 80
<211> LENGTH: 108
<212> TYPE: PRT
<213> ORGANISM: Homo sapiens

<400> SEQUENCE: 80

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Asn
                85                  90                  95

Thr Phe Gly Gln Gly Thr Lys Leu Glu Ile Lys Arg
            100                 105

<210> SEQ ID NO 81
<211> LENGTH: 321
<212> TYPE: DNA
<213> ORGANISM: Homo sapiens
<220> FEATURE:
<221> NAME/KEY: CDS
<222> LOCATION: (1)..(321)
<223> OTHER INFORMATION:

<400> SEQUENCE: 81 gga ggc gtg gtc cag cct ggg agg tcc ctg aga ctc tcc trt gca gcc      48
Gly Gly Val Val Gln Pro Gly Arg Ser Leu Arg Leu Ser Xaa Ala Ala
1               5                   10                  15 tct gga ttc acc ttc agt agc tat gct atg cac tgg gtc cgc cag gct      96
Ser Gly Phe Thr Phe Ser Ser Tyr Ala Met His Trp Val Arg Gln Ala
            20                  25                  30 cca ggc aag ggg ctg gag tgg gtg gca gtt ata tca tat gat gga agc     144
```

```
Pro Gly Lys Gly Leu Glu Trp Val Ala Val Ile Ser Tyr Asp Gly Ser
        35                  40                  45 aat aaa trc tac gca gac tcc gtg aag ggc cga ttc acc atc tcc aga        192
Asn Lys Xaa Tyr Ala Asp Ser Val Lys Gly Arg Phe Thr Ile Ser Arg
    50                  55                  60 gac aat tcc aag aac acg ctg tat ctg caa atg aac agc ctg aga gct        240
Asp Asn Ser Lys Asn Thr Leu Tyr Leu Gln Met Asn Ser Leu Arg Ala
65                  70                  75                  80 gag gac acg gct gtg tat tac tgt gcg aga gat cgg cac tcc tac gat        288
Glu Asp Thr Ala Val Tyr Tyr Cys Ala Arg Asp Arg His Ser Tyr Asp
                85                  90                  95 ttt tgg agt ggg tcc ctt gac tac tgg ggc cag                            321
Phe Trp Ser Gly Ser Leu Asp Tyr Trp Gly Gln
                100                 105
```

<210> SEQ ID NO 82
<211> LENGTH: 107
<212> TYPE: PRT
<213> ORGANISM: Homo sapiens
<220> FEATURE:
<221> NAME/KEY: misc_feature
<222> LOCATION: (14)
<223> OTHER INFORMATION: The 'Xaa' at location 14 stands for Cys, or
      Tyr.
<220> FEATURE:
<221> NAME/KEY: misc_feature
<222> LOCATION: (51)
<223> OTHER INFORMATION: The 'Xaa' at location 51 stands for Cys, or
      Tyr.

<400> SEQUENCE: 82

```
Gly Gly Val Val Gln Pro Gly Arg Ser Leu Arg Leu Ser Xaa Ala Ala
1               5                   10                  15

Ser Gly Phe Thr Phe Ser Ser Tyr Ala Met His Trp Val Arg Gln Ala
                20                  25                  30

Pro Gly Lys Gly Leu Glu Trp Val Ala Val Ile Ser Tyr Asp Gly Ser
        35                  40                  45

Asn Lys Xaa Tyr Ala Asp Ser Val Lys Gly Arg Phe Thr Ile Ser Arg
    50                  55                  60

Asp Asn Ser Lys Asn Thr Leu Tyr Leu Gln Met Asn Ser Leu Arg Ala
65                  70                  75                  80

Glu Asp Thr Ala Val Tyr Tyr Cys Ala Arg Asp Arg His Ser Tyr Asp
                85                  90                  95

Phe Trp Ser Gly Ser Leu Asp Tyr Trp Gly Gln
                100                 105
```

<210> SEQ ID NO 83
<211> LENGTH: 276
<212> TYPE: DNA
<213> ORGANISM: Homo sapiens
<220> FEATURE:
<221> NAME/KEY: CDS
<222> LOCATION: (1)..(276)
<223> OTHER INFORMATION:
<220> FEATURE:
<221> NAME/KEY: misc_feature
<222> LOCATION: (258)
<223> OTHER INFORMATION: n = t or c

<400> SEQUENCE: 83

```
tcc acc ctg tct gca tct gta gga gac aga gtc acc rtc act tgc cgg        48
Ser Thr Leu Ser Ala Ser Val Gly Asp Arg Val Thr Xaa Thr Cys Arg
1               5                   10                  15 gcc agt cag agt att agt agc tgg ttg gcc tgg tat cag cag aaa cca        96
```

```
Ala Ser Gln Ser Ile Ser Ser Trp Leu Ala Trp Tyr Gln Gln Lys Pro
            20                  25                  30 ggg aaa gcc cct aag ctc ctg atc tat aag gca tct agt tta gaa agt       144
Gly Lys Ala Pro Lys Leu Leu Ile Tyr Lys Ala Ser Ser Leu Glu Ser
        35                  40                  45 ggg gtc cca tca agg ttc agc ggc agt gga tct ggg aca gaa ttc act       192
Gly Val Pro Ser Arg Phe Ser Gly Ser Gly Ser Gly Thr Glu Phe Thr
    50                  55                  60 ctc acc atc agc agc ctg cag cct gat gat ttt gca act tat tac tgc       240
Leu Thr Ile Ser Ser Leu Gln Pro Asp Asp Phe Ala Thr Tyr Tyr Cys
65                  70                  75                  80 caa cag tat aat agt tan tct aac act ttt ggc cag                       276
Gln Gln Tyr Asn Ser Tyr Ser Asn Thr Phe Gly Gln
                85                  90
```

<210> SEQ ID NO 84
<211> LENGTH: 92
<212> TYPE: PRT
<213> ORGANISM: Homo sapiens
<220> FEATURE:
<221> NAME/KEY: misc_feature
<222> LOCATION: (13)
<223> OTHER INFORMATION: The 'Xaa' at location 13 stands for Val, or
      Ile.

<400> SEQUENCE: 84

```
Ser Thr Leu Ser Ala Ser Val Gly Asp Arg Val Thr Xaa Thr Cys Arg
1               5                   10                  15

Ala Ser Gln Ser Ile Ser Ser Trp Leu Ala Trp Tyr Gln Gln Lys Pro
            20                  25                  30

Gly Lys Ala Pro Lys Leu Leu Ile Tyr Lys Ala Ser Ser Leu Glu Ser
        35                  40                  45

Gly Val Pro Ser Arg Phe Ser Gly Ser Gly Ser Gly Thr Glu Phe Thr
    50                  55                  60

Leu Thr Ile Ser Ser Leu Gln Pro Asp Asp Phe Ala Thr Tyr Tyr Cys
65                  70                  75                  80

Gln Gln Tyr Asn Ser Tyr Ser Asn Thr Phe Gly Gln
                85                  90
```

<210> SEQ ID NO 85
<211> LENGTH: 15
<212> TYPE: DNA
<213> ORGANISM: Homo sapiens
<220> FEATURE:
<221> NAME/KEY: CDS
<222> LOCATION: (1)..(15)
<223> OTHER INFORMATION:

<400> SEQUENCE: 85

```
agc tat gct atg cac                                                    15
Ser Tyr Ala Met His
1               5
```

<210> SEQ ID NO 86
<211> LENGTH: 5
<212> TYPE: PRT
<213> ORGANISM: Homo sapiens

<400> SEQUENCE: 86

```
Ser Tyr Ala Met His
1               5
```

<210> SEQ ID NO 87

```
<211> LENGTH: 51
<212> TYPE: DNA
<213> ORGANISM: Homo sapiens
<220> FEATURE:
<221> NAME/KEY: CDS
<222> LOCATION: (1)..(51)
<223> OTHER INFORMATION:

<400> SEQUENCE: 87 gtt ata tca tat gat gga agc aat aaa trc tac gca gac tcc gtg aag    48
Val Ile Ser Tyr Asp Gly Ser Asn Lys Xaa Tyr Ala Asp Ser Val Lys
1               5                   10                  15 ggc                                                                51
Gly

<210> SEQ ID NO 88
<211> LENGTH: 17
<212> TYPE: PRT
<213> ORGANISM: Homo sapiens
<220> FEATURE:
<221> NAME/KEY: misc_feature
<222> LOCATION: (10)
<223> OTHER INFORMATION: The 'Xaa' at location 10 stands for Cys, or
      Tyr.

<400> SEQUENCE: 88

Val Ile Ser Tyr Asp Gly Ser Asn Lys Xaa Tyr Ala Asp Ser Val Lys
1               5                   10                  15

Gly

<210> SEQ ID NO 89
<211> LENGTH: 42
<212> TYPE: DNA
<213> ORGANISM: Homo sapiens
<220> FEATURE:
<221> NAME/KEY: CDS
<222> LOCATION: (1)..(42)
<223> OTHER INFORMATION:

<400> SEQUENCE: 89 gat cgg cac tcc tac gat ttt tgg agt ggg tcc ctt gac tac            42
Asp Arg His Ser Tyr Asp Phe Trp Ser Gly Ser Leu Asp Tyr
1               5                   10

<210> SEQ ID NO 90
<211> LENGTH: 14
<212> TYPE: PRT
<213> ORGANISM: Homo sapiens

<400> SEQUENCE: 90

Asp Arg His Ser Tyr Asp Phe Trp Ser Gly Ser Leu Asp Tyr
1               5                   10

<210> SEQ ID NO 91
<211> LENGTH: 33
<212> TYPE: DNA
<213> ORGANISM: Homo sapiens
<220> FEATURE:
<221> NAME/KEY: CDS
<222> LOCATION: (1)..(33)
<223> OTHER INFORMATION:

<400> SEQUENCE: 91 cgg gcc agt cag agt att agt agc tgg ttg gcc                        33
Arg Ala Ser Gln Ser Ile Ser Ser Trp Leu Ala
1               5                   10
```

```
<210> SEQ ID NO 92
<211> LENGTH: 11
<212> TYPE: PRT
<213> ORGANISM: Homo sapiens

<400> SEQUENCE: 92

Arg Ala Ser Gln Ser Ile Ser Ser Trp Leu Ala
1               5                   10

<210> SEQ ID NO 93
<211> LENGTH: 21
<212> TYPE: DNA
<213> ORGANISM: Homo sapiens
<220> FEATURE:
<221> NAME/KEY: CDS
<222> LOCATION: (1)..(21)
<223> OTHER INFORMATION:

<400> SEQUENCE: 93 aag gca tct agt tta gaa agt                                          21
Lys Ala Ser Ser Leu Glu Ser
1               5

<210> SEQ ID NO 94
<211> LENGTH: 7
<212> TYPE: PRT
<213> ORGANISM: Homo sapiens

<400> SEQUENCE: 94

Lys Ala Ser Ser Leu Glu Ser
1               5

<210> SEQ ID NO 95
<211> LENGTH: 27
<212> TYPE: DNA
<213> ORGANISM: Homo sapiens
<220> FEATURE:
<221> NAME/KEY: misc_feature
<222> LOCATION: (18)
<223> OTHER INFORMATION: n = t or c
<220> FEATURE:
<221> NAME/KEY: CDS
<222> LOCATION: (1)..(27)
<223> OTHER INFORMATION:

<400> SEQUENCE: 95 caa cag tat aat agt tan tct aac act                                  27
Gln Gln Tyr Asn Ser Tyr Ser Asn Thr
1               5

<210> SEQ ID NO 96
<211> LENGTH: 9
<212> TYPE: PRT
<213> ORGANISM: Homo sapiens

<400> SEQUENCE: 96

Gln Gln Tyr Asn Ser Tyr Ser Asn Thr
1               5

<210> SEQ ID NO 97
<211> LENGTH: 332
<212> TYPE: DNA
<213> ORGANISM: Unknown
<220> FEATURE:
<223> OTHER INFORMATION: Homo sapiens or Mus musculus
<220> FEATURE:
<221> NAME/KEY: CDS
<222> LOCATION: (1)..(330)
<223> OTHER INFORMATION:
```

<400> SEQUENCE: 97

| | | | | | | | | | | | | | | | | |
|---|---|---|---|---|---|---|---|---|---|---|---|---|---|---|---|---|
| gaa | att | gtg | ctg | act | cag | tct | cct | gct | tcc | tta | gct | gta | tct | ctg | ggg | 48 |
| Glu | Ile | Val | Leu | Thr | Gln | Ser | Pro | Ala | Ser | Leu | Ala | Val | Ser | Leu | Gly | |
| 1 | | | | 5 | | | | | 10 | | | | | 15 | | |
| cag | agg | gcc | acc | atc | tca | tac | agg | gcc | agc | aaa | agt | gtc | agt | aca | tct | 96 |
| Gln | Arg | Ala | Thr | Ile | Ser | Tyr | Arg | Ala | Ser | Lys | Ser | Val | Ser | Thr | Ser | |
| | | | 20 | | | | | 25 | | | | | 30 | | | |
| ggc | tat | agt | tat | atg | cac | tgg | aac | caa | cag | aaa | cca | gga | cag | cca | ccc | 144 |
| Gly | Tyr | Ser | Tyr | Met | His | Trp | Asn | Gln | Gln | Lys | Pro | Gly | Gln | Pro | Pro | |
| | | 35 | | | | | 40 | | | | | 45 | | | | |
| aga | ctc | ctc | atc | tat | ctt | gta | tcc | aac | cta | gaa | tct | ggg | gtc | cct | gcc | 192 |
| Arg | Leu | Leu | Ile | Tyr | Leu | Val | Ser | Asn | Leu | Glu | Ser | Gly | Val | Pro | Ala | |
| 50 | | | | | 55 | | | | | 60 | | | | | | |
| agg | ttc | agt | ggc | agt | ggg | tct | ggg | aca | gac | ttc | acc | ctc | aac | atc | cat | 240 |
| Arg | Phe | Ser | Gly | Ser | Gly | Ser | Gly | Thr | Asp | Phe | Thr | Leu | Asn | Ile | His | |
| 65 | | | | | 70 | | | | | 75 | | | | | 80 | |
| cct | gtg | gag | gag | gag | gat | gct | gca | acc | tat | tac | tgt | cag | cac | att | agg | 288 |
| Pro | Val | Glu | Glu | Glu | Asp | Ala | Ala | Thr | Tyr | Tyr | Cys | Gln | His | Ile | Arg | |
| | | | | 85 | | | | | 90 | | | | | 95 | | |
| gag | ctt | aca | cgt | tcg | gag | ggg | gga | cca | agg | tgg | aaa | tca | aac | ga | | 332 |
| Glu | Leu | Thr | Arg | Ser | Glu | Gly | Gly | Pro | Arg | Trp | Lys | Ser | Asn | | | |
| | | | 100 | | | | | 105 | | | | | 110 | | | |

<210> SEQ ID NO 98
<211> LENGTH: 110
<212> TYPE: PRT
<213> ORGANISM: Unknown
<220> FEATURE:
<223> OTHER INFORMATION: Homo sapiens or Mus musculus

<400> SEQUENCE: 98

Glu Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Arg Trp Lys Ser Asn
            100                 105                 110

<210> SEQ ID NO 99
<211> LENGTH: 332
<212> TYPE: DNA
<213> ORGANISM: Unknown
<220> FEATURE:
<223> OTHER INFORMATION: Homo sapiens or Mus musculus
<220> FEATURE:
<221> NAME/KEY: CDS
<222> LOCATION: (1)..(330)
<223> OTHER INFORMATION:

<400> SEQUENCE: 99

| | | | | | | | | | | | | | | | | |
|---|---|---|---|---|---|---|---|---|---|---|---|---|---|---|---|---|
| gat | gtt | gtg | atg | act | cag | tct | cct | gct | tcc | tta | gct | gta | tct | ctg | ggg | 48 |
| Asp | Val | Val | Met | Thr | Gln | Ser | Pro | Ala | Ser | Leu | Ala | Val | Ser | Leu | Gly | |
| 1 | | | | 5 | | | | | 10 | | | | | 15 | | |

-continued

```
cag agg gcc acc atc tca tac agg gcc agc aaa agt gtc agt aca tct        96
Gln Arg Ala Thr Ile Ser Tyr Arg Ala Ser Lys Ser Val Ser Thr Ser
                20                  25                  30 ggc tat agt tat atg cac tgg aac caa cag aaa cca gga cag cca ccc       144
Gly Tyr Ser Tyr Met His Trp Asn Gln Gln Lys Pro Gly Gln Pro Pro
            35                  40                  45 aga ctc ctc atc tat ctt gta tcc aac cta gaa tct ggg gtc cct gcc       192
Arg Leu Leu Ile Tyr Leu Val Ser Asn Leu Glu Ser Gly Val Pro Ala
        50                  55                  60 agg ttc agt ggc agt ggg tct ggg aca gac ttc acc ctc aac atc cat       240
Arg Phe Ser Gly Ser Gly Ser Gly Thr Asp Phe Thr Leu Asn Ile His
65                  70                  75                  80 cct gtg gag gag gag gat gct gca acc tat tac tgt cag cac att agg       288
Pro Val Glu Glu Glu Asp Ala Ala Thr Tyr Tyr Cys Gln His Ile Arg
                85                  90                  95 gag ctt aca cgt tcg gag ggg gga cca agg tgg aaa tca aac ga            332
Glu Leu Thr Arg Ser Glu Gly Gly Pro Arg Trp Lys Ser Asn
            100                 105                 110
```

<210> SEQ ID NO 100
<211> LENGTH: 110
<212> TYPE: PRT
<213> ORGANISM: Unknown
<220> FEATURE:
<223> OTHER INFORMATION: Homo sapiens or Mus musculus

<400> SEQUENCE: 100

```
Asp Val Val Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Arg Trp Lys Ser Asn
            100                 105                 110
```

<210> SEQ ID NO 101
<211> LENGTH: 332
<212> TYPE: DNA
<213> ORGANISM: Unknown
<220> FEATURE:
<223> OTHER INFORMATION: Homo sapiens or Mus musculus
<220> FEATURE:
<221> NAME/KEY: CDS
<222> LOCATION: (1)..(330)
<223> OTHER INFORMATION:

<400> SEQUENCE: 101

```
gac atc gtg atg acc cag tct cct gct tcc tta gct gta tct ctg ggg        48
Asp Ile Val Met Thr Gln Ser Pro Ala Ser Leu Ala Val Ser Leu Gly
1               5                   10                  15 cag agg gcc acc atc tca tac agg gcc agc aaa agt gtc agt aca tct        96
Gln Arg Ala Thr Ile Ser Tyr Arg Ala Ser Lys Ser Val Ser Thr Ser
                20                  25                  30 ggc tat agt tat atg cac tgg aac caa cag aaa cca gga cag cca ccc       144
Gly Tyr Ser Tyr Met His Trp Asn Gln Gln Lys Pro Gly Gln Pro Pro
```

```
Gly Tyr Ser Tyr Met His Trp Asn Gln Gln Lys Pro Gly Gln Pro
        35                  40                  45 aga ctc ctc atc tat ctt gta tcc aac cta gaa tct ggg gtc cct gcc    192
Arg Leu Leu Ile Tyr Leu Val Ser Asn Leu Glu Ser Gly Val Pro Ala
 50                  55                  60 agg ttc agt ggc agt ggg tct ggg aca gac ttc acc ctc aac atc cat    240
Arg Phe Ser Gly Ser Gly Ser Gly Thr Asp Phe Thr Leu Asn Ile His
 65                  70                  75                  80 cct gtg gag gag gag gat gct gca acc tat tac tgt cag cac att agg    288
Pro Val Glu Glu Glu Asp Ala Ala Thr Tyr Tyr Cys Gln His Ile Arg
                 85                  90                  95 gag ctt aca cgt tcg gag ggg gga cca agg tgg aaa tca aac ga         332
Glu Leu Thr Arg Ser Glu Gly Gly Pro Arg Trp Lys Ser Asn
            100                 105                 110

<210> SEQ ID NO 102
<211> LENGTH: 110
<212> TYPE: PRT
<213> ORGANISM: Unknown
<220> FEATURE:
<223> OTHER INFORMATION: Homo sapiens or Mus musculus

<400> SEQUENCE: 102

Asp Ile Val Met Thr Gln Ser Pro Ala Ser Leu Ala Val Ser Leu Gly
 1               5                  10                  15

Gln Arg Ala Thr Ile Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                 85                  90                  95

Glu Leu Thr Arg Ser Glu Gly Gly Pro Arg Trp Lys Ser Asn
            100                 105                 110

<210> SEQ ID NO 103
<211> LENGTH: 332
<212> TYPE: DNA
<213> ORGANISM: Unknown
<220> FEATURE:
<223> OTHER INFORMATION: Homo sapiens or Mus musculus
<220> FEATURE:
<221> NAME/KEY: CDS
<222> LOCATION: (1)..(330)
<223> OTHER INFORMATION:

<400> SEQUENCE: 103 gat gtt gtg atg act cag tct cct gct tcc tta gct gta tct ctg ggg    48
Asp Val Val Met Thr Gln Ser Pro Ala Ser Leu Ala Val Ser Leu Gly
 1               5                  10                  15 cag agg gcc acc atc tca tac agg gcc agc aaa agt gtc agt aca tct    96
Gln Arg Ala Thr Ile Ser Tyr Arg Ala Ser Lys Ser Val Ser Thr Ser
                20                  25                  30 ggc tat agt tat atg cac tgg aac caa cag aaa cca gga cag cca ccc   144
Gly Tyr Ser Tyr Met His Trp Asn Gln Gln Lys Pro Gly Gln Pro Pro
        35                  40                  45 aga ctc ctc atc tat ctt gta tcc aac cta gaa tct ggg gtc cct gcc   192
Arg Leu Leu Ile Tyr Leu Val Ser Asn Leu Glu Ser Gly Val Pro Ala
 50                  55                  60
```

```
agg ttc agt ggc agt ggg tct ggg aca gac ttc acc ctc aac atc cat    240
Arg Phe Ser Gly Ser Gly Ser Gly Thr Asp Phe Thr Leu Asn Ile His
 65                  70                  75                  80 cct gtg gag gag gag gat gct gca acc tat tac tgt cag cac att agg    288
Pro Val Glu Glu Glu Asp Ala Ala Thr Tyr Tyr Cys Gln His Ile Arg
                 85                  90                  95 gag ctt aca cgt tcg gag ggg gga cca agc tgg aga tca aac ga         332
Glu Leu Thr Arg Ser Glu Gly Gly Pro Ser Trp Arg Ser Asn
            100                 105                 110
```

<210> SEQ ID NO 104
<211> LENGTH: 110
<212> TYPE: PRT
<213> ORGANISM: Unknown
<220> FEATURE:
<223> OTHER INFORMATION: Homo sapiens or Mus musculus

<400> SEQUENCE: 104

```
Asp Val Val Met Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
             20                  25                  30

Gly Tyr Ser Tyr Met His Trp Asn Gln Gln Lys Pro Gly Gln Pro Pro
         35                  40                  45

Arg Leu Leu Ile Tyr Leu Val Ser Asn Leu Glu Ser Gly Val Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                 85                  90                  95

Glu Leu Thr Arg Ser Glu Gly Gly Pro Ser Trp Arg Ser Asn
            100                 105                 110
```

<210> SEQ ID NO 105
<211> LENGTH: 332
<212> TYPE: DNA
<213> ORGANISM: Unknown
<220> FEATURE:
<223> OTHER INFORMATION: Homo sapiens or Mus musculus
<220> FEATURE:
<221> NAME/KEY: CDS
<222> LOCATION: (1)..(330)
<223> OTHER INFORMATION:

<400> SEQUENCE: 105

```
gac atc gtg atg acc cag tct cct gct tcc tta gct gta tct ctg ggg     48
Asp Ile Val Met Thr Gln Ser Pro Ala Ser Leu Ala Val Ser Leu Gly
  1               5                  10                  15 cag agg gcc acc atc tca tac agg gcc agc aaa agt gtc agt aca tct     96
Gln Arg Ala Thr Ile Ser Tyr Arg Ala Ser Lys Ser Val Ser Thr Ser
             20                  25                  30 ggc tat agt tat atg cac tgg aac caa cag aaa cca gga cag cca ccc    144
Gly Tyr Ser Tyr Met His Trp Asn Gln Gln Lys Pro Gly Gln Pro Pro
         35                  40                  45 aga ctc ctc atc tat ctt gta tcc aac cta gaa tct ggg gtc cct gcc    192
Arg Leu Leu Ile Tyr Leu Val Ser Asn Leu Glu Ser Gly Val Pro Ala
     50                  55                  60 agg ttc agt ggc agt ggg tct ggg aca gac ttc acc ctc aac atc cat    240
Arg Phe Ser Gly Ser Gly Ser Gly Thr Asp Phe Thr Leu Asn Ile His
 65                  70                  75                  80 cct gtg gag gag gag gat gct gta acc tat tac tgt cag cac att agg    288
Pro Val Glu Glu Glu Asp Ala Val Thr Tyr Tyr Cys Gln His Ile Arg
                 85                  90                  95
```

```
Pro Val Glu Glu Glu Asp Ala Val Thr Tyr Tyr Cys Gln His Ile Arg
                85                  90                  95 gag ctt aca cgt tcg gag ggg gga cca agc tgg aga tca aac ga         332
Glu Leu Thr Arg Ser Glu Gly Gly Pro Ser Trp Arg Ser Asn
            100                 105                 110

<210> SEQ ID NO 106
<211> LENGTH: 110
<212> TYPE: PRT
<213> ORGANISM: Unknown
<220> FEATURE:
<223> OTHER INFORMATION: Homo sapiens or Mus musculus

<400> SEQUENCE: 106

Asp Ile Val Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Val Thr Tyr Tyr Cys Gln His Ile Arg
                85                  90                  95

Glu Leu Thr Arg Ser Glu Gly Gly Pro Ser Trp Arg Ser Asn
            100                 105                 110

<210> SEQ ID NO 107
<211> LENGTH: 12
<212> TYPE: PRT
<213> ORGANISM: Homo sapiens

<400> SEQUENCE: 107

Val Glu Leu Gln Glu Leu Asn Asp Arg Phe Ala Asn
1               5                   10

<210> SEQ ID NO 108
<211> LENGTH: 24
<212> TYPE: DNA
<213> ORGANISM: Artificial
<220> FEATURE:
<223> OTHER INFORMATION: primer

<400> SEQUENCE: 108
tggaagaggc acgttctttt cttt                                          24

<210> SEQ ID NO 109
<211> LENGTH: 24
<212> TYPE: DNA
<213> ORGANISM: Artificial
<220> FEATURE:
<223> OTHER INFORMATION: primer

<400> SEQUENCE: 109
agactctccc ctgttgaagc tctt                                          24

<210> SEQ ID NO 110
<211> LENGTH: 57
<212> TYPE: DNA
<213> ORGANISM: Homo sapiens
<220> FEATURE:
```

```
<221> NAME/KEY: CDS
<222> LOCATION: (1)..(57)
<223> OTHER INFORMATION:

<400> SEQUENCE: 110 gga acc ctg gtc acc gtc tcc tca ggg agt gca tcc gcc cca acc ctt     48
Gly Thr Leu Val Thr Val Ser Ser Gly Ser Ala Ser Ala Pro Thr Leu
1               5                   10                  15 ttc ccc ctc                                                          57
Phe Pro Leu <210> SEQ ID NO 111
<211> LENGTH: 19
<212> TYPE: PRT
<213> ORGANISM: Homo sapiens

<400> SEQUENCE: 111

Gly Thr Leu Val Thr Val Ser Ser Gly Ser Ala Ser Ala Pro Thr Leu
1               5                   10                  15

Phe Pro Leu

<210> SEQ ID NO 112
<211> LENGTH: 99
<212> TYPE: DNA
<213> ORGANISM: Homo sapiens
<220> FEATURE:
<221> NAME/KEY: CDS
<222> LOCATION: (1)..(99)
<223> OTHER INFORMATION:

<400> SEQUENCE: 112 ggg acc aag ctg gag atc aaa cga act gtg gct gca cca tct gtc ttc     48
Gly Thr Lys Leu Glu Ile Lys Arg Thr Val Ala Ala Pro Ser Val Phe
1               5                   10                  15 atc ttc ccg cca tct gat gag cag ttg aaa tct gga act gcc tct gtt     96
Ile Phe Pro Pro Ser Asp Glu Gln Leu Lys Ser Gly Thr Ala Ser Val
                20                  25                  30 gtg                                                                  99
Val

<210> SEQ ID NO 113
<211> LENGTH: 33
<212> TYPE: PRT
<213> ORGANISM: Homo sapiens

<400> SEQUENCE: 113

Gly Thr Lys Leu Glu Ile Lys Arg Thr Val Ala Ala Pro Ser Val Phe
1               5                   10                  15

Ile Phe Pro Pro Ser Asp Glu Gln Leu Lys Ser Gly Thr Ala Ser Val
                20                  25                  30

Val

<210> SEQ ID NO 114
<211> LENGTH: 345
<212> TYPE: DNA
<213> ORGANISM: Homo sapiens
<220> FEATURE:
<221> NAME/KEY: CDS
<222> LOCATION: (1)..(345)
<223> OTHER INFORMATION:

<400> SEQUENCE: 114 gga ggc gtg gtc cag cct ggg agg tcc ctg aga ctc tcc trt gca gcc     48
Gly Gly Val Val Gln Pro Gly Arg Ser Leu Arg Leu Ser Xaa Ala Ala
```

```
                1               5                   10                  15
tct gga ttc acc ttc agt agc tat gct atg cac tgg gtc cgc cag gct    96
Ser Gly Phe Thr Phe Ser Ser Tyr Ala Met His Trp Val Arg Gln Ala
                    20                  25                  30 cca ggc aag ggg ctg gag tgg gtg gca gtt ata tca tat gat gga agc    144
Pro Gly Lys Gly Leu Glu Trp Val Ala Val Ile Ser Tyr Asp Gly Ser
            35                  40                  45 aat aaa trc tac gca gac tcc gtg aag ggc cga ttc acc atc tcc aga    192
Asn Lys Xaa Tyr Ala Asp Ser Val Lys Gly Arg Phe Thr Ile Ser Arg
    50                  55                  60 gac aat tcc aag aac acg ctg tat ctg caa atg aac agc ctg aga gct    240
Asp Asn Ser Lys Asn Thr Leu Tyr Leu Gln Met Asn Ser Leu Arg Ala
65                  70                  75                  80 gag gac acg gct gtg tat tac tgt gcg aga gat cgg cac tcc tac gat    288
Glu Asp Thr Ala Val Tyr Tyr Cys Ala Arg Asp Arg His Ser Tyr Asp
                85                  90                  95 ttt tgg agt ggg tcc ctt gac tac tgg ggc cag gga acc ctg gtc acc    336
Phe Trp Ser Gly Ser Leu Asp Tyr Trp Gly Gln Gly Thr Leu Val Thr
            100                 105                 110 gtc tcc tca                                                        345
Val Ser Ser
        115

<210> SEQ ID NO 115
<211> LENGTH: 115
<212> TYPE: PRT
<213> ORGANISM: Homo sapiens
<220> FEATURE:
<221> NAME/KEY: misc_feature
<222> LOCATION: (14)
<223> OTHER INFORMATION: The 'Xaa' at location 14 stands for Cys, or
      Tyr.
<220> FEATURE:
<221> NAME/KEY: misc_feature
<222> LOCATION: (51)
<223> OTHER INFORMATION: The 'Xaa' at location 51 stands for Cys, or
      Tyr.

<400> SEQUENCE: 115

Gly Gly Val Val Gln Pro Gly Arg Ser Leu Arg Leu Ser Xaa Ala Ala
1               5                   10                  15

Ser Gly Phe Thr Phe Ser Ser Tyr Ala Met His Trp Val Arg Gln Ala
            20                  25                  30

Pro Gly Lys Gly Leu Glu Trp Val Ala Val Ile Ser Tyr Asp Gly Ser
        35                  40                  45

Asn Lys Xaa Tyr Ala Asp Ser Val Lys Gly Arg Phe Thr Ile Ser Arg
    50                  55                  60

Asp Asn Ser Lys Asn Thr Leu Tyr Leu Gln Met Asn Ser Leu Arg Ala
65                  70                  75                  80

Glu Asp Thr Ala Val Tyr Tyr Cys Ala Arg Asp Arg His Ser Tyr Asp
                85                  90                  95

Phe Trp Ser Gly Ser Leu Asp Tyr Trp Gly Gln Gly Thr Leu Val Thr
            100                 105                 110

Val Ser Ser
        115

<210> SEQ ID NO 116
<211> LENGTH: 300
<212> TYPE: DNA
<213> ORGANISM: Homo sapiens
<220> FEATURE:
<221> NAME/KEY: misc_feature
```

```
<222> LOCATION: (258)
<223> OTHER INFORMATION: n = t or c
<220> FEATURE:
<221> NAME/KEY: CDS
<222> LOCATION: (1)..(300)
<223> OTHER INFORMATION:

<400> SEQUENCE: 116 tcc acc ctg tct gca tct gta gga gac aga gtc acc rtc act tgc cgg       48
Ser Thr Leu Ser Ala Ser Val Gly Asp Arg Val Thr Xaa Thr Cys Arg
 1               5                  10                  15 gcc agt cag agt att agt agc tgg ttg gcc tgg tat cag cag aaa cca       96
Ala Ser Gln Ser Ile Ser Ser Trp Leu Ala Trp Tyr Gln Gln Lys Pro
             20                  25                  30 ggg aaa gcc cct aag ctc ctg atc tat aag gca tct agt tta gaa agt      144
Gly Lys Ala Pro Lys Leu Leu Ile Tyr Lys Ala Ser Ser Leu Glu Ser
         35                  40                  45 ggg gtc cca tca agg ttc agc ggc agt gga tct ggg aca gaa ttc act      192
Gly Val Pro Ser Arg Phe Ser Gly Ser Gly Ser Gly Thr Glu Phe Thr
     50                  55                  60 ctc acc atc agc agc ctg cag cct gat gat ttt gca act tat tac tgc      240
Leu Thr Ile Ser Ser Leu Gln Pro Asp Asp Phe Ala Thr Tyr Tyr Cys
 65                  70                  75                  80 caa cag tat aat agt tan tct aac act ttt ggc cag ggg acc aag ctg      288
Gln Gln Tyr Asn Ser Tyr Ser Asn Thr Phe Gly Gln Gly Thr Lys Leu
                 85                  90                  95 gag atc aaa cga                                                      300
Glu Ile Lys Arg
            100

<210> SEQ ID NO 117
<211> LENGTH: 100
<212> TYPE: PRT
<213> ORGANISM: Homo sapiens
<220> FEATURE:
<221> NAME/KEY: misc_feature
<222> LOCATION: (13)
<223> OTHER INFORMATION: The 'Xaa' at location 13 stands for Val, or
      Ile.

<400> SEQUENCE: 117

Ser Thr Leu Ser Ala Ser Val Gly Asp Arg Val Thr Xaa Thr Cys Arg
 1               5                  10                  15

Ala Ser Gln Ser Ile Ser Ser Trp Leu Ala Trp Tyr Gln Gln Lys Pro
             20                  25                  30

Gly Lys Ala Pro Lys Leu Leu Ile Tyr Lys Ala Ser Ser Leu Glu Ser
         35                  40                  45

Gly Val Pro Ser Arg Phe Ser Gly Ser Gly Ser Gly Thr Glu Phe Thr
     50                  55                  60

Leu Thr Ile Ser Ser Leu Gln Pro Asp Asp Phe Ala Thr Tyr Tyr Cys
 65                  70                  75                  80

Gln Gln Tyr Asn Ser Tyr Ser Asn Thr Phe Gly Gln Gly Thr Lys Leu
                 85                  90                  95

Glu Ile Lys Arg
            100

<210> SEQ ID NO 118
<211> LENGTH: 378
<212> TYPE: DNA
<213> ORGANISM: Homo sapiens
<220> FEATURE:
<221> NAME/KEY: CDS
<222> LOCATION: (1)..(378)
```

```
<223> OTHER INFORMATION:

<400> SEQUENCE: 118 gga ggc gtg gtc cag cct ggg agg tcc ctg aga ctc tcc trt gca gcc      48
Gly Gly Val Val Gln Pro Gly Arg Ser Leu Arg Leu Ser Xaa Ala Ala
1               5                   10                  15 tct gga ttc acc ttc agt agc tat gct atg cac tgg gtc cgc cag gct      96
Ser Gly Phe Thr Phe Ser Ser Tyr Ala Met His Trp Val Arg Gln Ala
            20                  25                  30 cca ggc aag ggg ctg gag tgg gtg gca gtt ata tca tat gat gga agc     144
Pro Gly Lys Gly Leu Glu Trp Val Ala Val Ile Ser Tyr Asp Gly Ser
        35                  40                  45 aat aaa trc tac gca gac tcc gtg aag ggc cga ttc acc atc tcc aga     192
Asn Lys Xaa Tyr Ala Asp Ser Val Lys Gly Arg Phe Thr Ile Ser Arg
    50                  55                  60 gac aat tcc aag aac acg ctg tat ctg caa atg aac agc ctg aga gct     240
Asp Asn Ser Lys Asn Thr Leu Tyr Leu Gln Met Asn Ser Leu Arg Ala
65                  70                  75                  80 gag gac acg gct gtg tat tac tgt gcg aga gat cgg cac tcc tac gat     288
Glu Asp Thr Ala Val Tyr Tyr Cys Ala Arg Asp Arg His Ser Tyr Asp
                85                  90                  95 ttt tgg agt ggg tcc ctt gac tac tgg ggc cag gga acc ctg gtc acc     336
Phe Trp Ser Gly Ser Leu Asp Tyr Trp Gly Gln Gly Thr Leu Val Thr
            100                 105                 110 gtc tcc tca ggg agt gca tcc gcc cca acc ctt ttc ccc ctc             378
Val Ser Ser Gly Ser Ala Ser Ala Pro Thr Leu Phe Pro Leu
        115                 120                 125

<210> SEQ ID NO 119
<211> LENGTH: 126
<212> TYPE: PRT
<213> ORGANISM: Homo sapiens
<220> FEATURE:
<221> NAME/KEY: misc_feature
<222> LOCATION: (14)
<223> OTHER INFORMATION: The 'Xaa' at location 14 stands for Cys, or
      Tyr.
<220> FEATURE:
<221> NAME/KEY: misc_feature
<222> LOCATION: (51)
<223> OTHER INFORMATION: The 'Xaa' at location 51 stands for Cys, or
      Tyr.

<400> SEQUENCE: 119

Gly Gly Val Val Gln Pro Gly Arg Ser Leu Arg Leu Ser Xaa Ala Ala
1               5                   10                  15

Ser Gly Phe Thr Phe Ser Ser Tyr Ala Met His Trp Val Arg Gln Ala
            20                  25                  30

Pro Gly Lys Gly Leu Glu Trp Val Ala Val Ile Ser Tyr Asp Gly Ser
        35                  40                  45

Asn Lys Xaa Tyr Ala Asp Ser Val Lys Gly Arg Phe Thr Ile Ser Arg
    50                  55                  60

Asp Asn Ser Lys Asn Thr Leu Tyr Leu Gln Met Asn Ser Leu Arg Ala
65                  70                  75                  80

Glu Asp Thr Ala Val Tyr Tyr Cys Ala Arg Asp Arg His Ser Tyr Asp
                85                  90                  95

Phe Trp Ser Gly Ser Leu Asp Tyr Trp Gly Gln Gly Thr Leu Val Thr
            100                 105                 110

Val Ser Ser Gly Ser Ala Ser Ala Pro Thr Leu Phe Pro Leu
        115                 120                 125
```

<210> SEQ ID NO 120
<211> LENGTH: 375
<212> TYPE: DNA
<213> ORGANISM: Homo sapiens
<220> FEATURE:
<221> NAME/KEY: misc_feature
<222> LOCATION: (258)
<223> OTHER INFORMATION: n = t or c
<220> FEATURE:
<221> NAME/KEY: CDS
<222> LOCATION: (1)..(375)
<223> OTHER INFORMATION:

<400> SEQUENCE: 120

| tcc | acc | ctg | tct | gca | tct | gta | gga | gac | aga | gtc | acc | rtc | act | tgc | cgg | 48 |
|-----|-----|-----|-----|-----|-----|-----|-----|-----|-----|-----|-----|-----|-----|-----|-----|-----|
| Ser | Thr | Leu | Ser | Ala | Ser | Val | Gly | Asp | Arg | Val | Thr | Xaa | Thr | Cys | Arg | |
| 1 | | | | 5 | | | | | 10 | | | | | 15 | | |

| gcc | agt | cag | agt | att | agt | agc | tgg | ttg | gcc | tgg | tat | cag | cag | aaa | cca | 96 |
|-----|-----|-----|-----|-----|-----|-----|-----|-----|-----|-----|-----|-----|-----|-----|-----|-----|
| Ala | Ser | Gln | Ser | Ile | Ser | Ser | Trp | Leu | Ala | Trp | Tyr | Gln | Gln | Lys | Pro | |
| | | | 20 | | | | | 25 | | | | | 30 | | | |

| ggg | aaa | gcc | cct | aag | ctc | ctg | atc | tat | aag | gca | tct | agt | tta | gaa | agt | 144 |
|-----|-----|-----|-----|-----|-----|-----|-----|-----|-----|-----|-----|-----|-----|-----|-----|-----|
| Gly | Lys | Ala | Pro | Lys | Leu | Leu | Ile | Tyr | Lys | Ala | Ser | Ser | Leu | Glu | Ser | |
| | | 35 | | | | | 40 | | | | | 45 | | | | |

| ggg | gtc | cca | tca | agg | ttc | agc | ggc | agt | gga | tct | ggg | aca | gaa | ttc | act | 192 |
|-----|-----|-----|-----|-----|-----|-----|-----|-----|-----|-----|-----|-----|-----|-----|-----|-----|
| Gly | Val | Pro | Ser | Arg | Phe | Ser | Gly | Ser | Gly | Ser | Gly | Thr | Glu | Phe | Thr | |
| | 50 | | | | | 55 | | | | | 60 | | | | | |

| ctc | acc | atc | agc | agc | ctg | cag | cct | gat | gat | ttt | gca | act | tat | tac | tgc | 240 |
|-----|-----|-----|-----|-----|-----|-----|-----|-----|-----|-----|-----|-----|-----|-----|-----|-----|
| Leu | Thr | Ile | Ser | Ser | Leu | Gln | Pro | Asp | Asp | Phe | Ala | Thr | Tyr | Tyr | Cys | |
| 65 | | | | | 70 | | | | | 75 | | | | | 80 | |

| caa | cag | tat | aat | agt | tan | tct | aac | act | ttt | ggc | cag | ggg | acc | aag | ctg | 288 |
|-----|-----|-----|-----|-----|-----|-----|-----|-----|-----|-----|-----|-----|-----|-----|-----|-----|
| Gln | Gln | Tyr | Asn | Ser | Tyr | Ser | Asn | Thr | Phe | Gly | Gln | Gly | Thr | Lys | Leu | |
| | | | | 85 | | | | | 90 | | | | | 95 | | |

| gag | atc | aaa | cga | act | gtg | gct | gca | cca | tct | gtc | ttc | atc | ttc | ccg | cca | 336 |
|-----|-----|-----|-----|-----|-----|-----|-----|-----|-----|-----|-----|-----|-----|-----|-----|-----|
| Glu | Ile | Lys | Arg | Thr | Val | Ala | Ala | Pro | Ser | Val | Phe | Ile | Phe | Pro | Pro | |
| | | | 100 | | | | | 105 | | | | | 110 | | | |

| tct | gat | gag | cag | ttg | aaa | tct | gga | act | gcc | tct | gtt | gtg | | | | 375 |
|-----|-----|-----|-----|-----|-----|-----|-----|-----|-----|-----|-----|-----|---|---|---|-----|
| Ser | Asp | Glu | Gln | Leu | Lys | Ser | Gly | Thr | Ala | Ser | Val | Val | | | | |
| | | | 115 | | | | | 120 | | | | | 125 | | | |

<210> SEQ ID NO 121
<211> LENGTH: 125
<212> TYPE: PRT
<213> ORGANISM: Homo sapiens
<220> FEATURE:
<221> NAME/KEY: misc_feature
<222> LOCATION: (13)
<223> OTHER INFORMATION: The 'Xaa' at location 13 stands for Val, or
    Ile.

<400> SEQUENCE: 121

Ser Thr Leu Ser Ala Ser Val Gly Asp Arg Val Thr Xaa Thr Cys Arg
1               5                   10                  15

Ala Ser Gln Ser Ile Ser Ser Trp Leu Ala Trp Tyr Gln Gln Lys Pro
            20                  25                  30

Gly Lys Ala Pro Lys Leu Leu Ile Tyr Lys Ala Ser Ser Leu Glu Ser
        35                  40                  45

Gly Val Pro Ser Arg Phe Ser Gly Ser Gly Ser Gly Thr Glu Phe Thr
    50                  55                  60

Leu Thr Ile Ser Ser Leu Gln Pro Asp Asp Phe Ala Thr Tyr Tyr Cys
65                  70                  75                  80

Gln Gln Tyr Asn Ser Tyr Ser Asn Thr Phe Gly Gln Gly Thr Lys Leu
                85                  90                  95

Glu Ile Lys Arg Thr Val Ala Ala Pro Ser Val Phe Ile Phe Pro Pro

```
                100             105              110
Ser Asp Glu Gln Leu Lys Ser Gly Thr Ala Ser Val Val
        115             120              125
```

<210> SEQ ID NO 122
<211> LENGTH: 25
<212> TYPE: DNA
<213> ORGANISM: Artificial
<220> FEATURE:
<223> OTHER INFORMATION: primer

<400> SEQUENCE: 122
cctgggagtt acccgattgg agggc                                           25

<210> SEQ ID NO 123
<211> LENGTH: 94
<212> TYPE: DNA
<213> ORGANISM: Artificial
<220> FEATURE:
<223> OTHER INFORMATION: primer

<400> SEQUENCE: 123
cccaagcttc accatgaaac acctgtggtt cttcctcctg ctggtggcag ctcccagatg     60
ggtcctgtcc gaggtgcagc tggtggagtc tggg                                 94

<210> SEQ ID NO 124
<211> LENGTH: 30
<212> TYPE: DNA
<213> ORGANISM: Artificial
<220> FEATURE:
<223> OTHER INFORMATION: primer

<400> SEQUENCE: 124
cccgctagct gaggagacgg tgaccagggt                                      30

<210> SEQ ID NO 125
<211> LENGTH: 92
<212> TYPE: DNA
<213> ORGANISM: Artificial
<220> FEATURE:
<223> OTHER INFORMATION: primer

<400> SEQUENCE: 125
cccaagctta tggcgttgca gacccaggtc ttcatttctc tgttgctctg gatctctggt     60
gcctacgggg acatcgtgat gacccagtct cc                                   92

<210> SEQ ID NO 126
<211> LENGTH: 30
<212> TYPE: DNA
<213> ORGANISM: Artificial
<220> FEATURE:
<223> OTHER INFORMATION: primer

<400> SEQUENCE: 126
ccccgtacgt ttgatctcca gcttggtccc                                      30

<210> SEQ ID NO 127
<211> LENGTH: 22
<212> TYPE: DNA
<213> ORGANISM: Artificial
<220> FEATURE:
<223> OTHER INFORMATION: primer

<400> SEQUENCE: 127

```
cccactgctt actggcttat cg                                              22
```

<210> SEQ ID NO 128
<211> LENGTH: 18
<212> TYPE: DNA
<213> ORGANISM: Artificial
<220> FEATURE:
<223> OTHER INFORMATION: primer

<400> SEQUENCE: 128

```
ggtgctcttg gaggaggg                                                   18
```

<210> SEQ ID NO 129
<211> LENGTH: 1419
<212> TYPE: DNA
<213> ORGANISM: Homo sapiens
<220> FEATURE:
<221> NAME/KEY: CDS
<222> LOCATION: (1)..(1419)
<223> OTHER INFORMATION:

<400> SEQUENCE: 129

```
atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
 1               5                  10                  15 gtc ctg tcc gag gtg cag ctg gtg gag tct ggg gga ggc gtg gtc cag      96
Val Leu Ser Glu Val Gln Leu Val Glu Ser Gly Gly Gly Val Val Gln
             20                  25                  30 cct ggg agg tcc ctg aga ctc tcc tgt gca gcc tct gga ttc acc ttc     144
Pro Gly Arg Ser Leu Arg Leu Ser Cys Ala Ala Ser Gly Phe Thr Phe
         35                  40                  45 agt agc tat gct atg cac tgg gtc cgc cag gct cca ggc aag ggg ctg     192
Ser Ser Tyr Ala Met His Trp Val Arg Gln Ala Pro Gly Lys Gly Leu
     50                  55                  60 gag tgg gtg gca gtt ata tca tat gat gga agc aat aaa tac tac gca     240
Glu Trp Val Ala Val Ile Ser Tyr Asp Gly Ser Asn Lys Tyr Tyr Ala
 65                  70                  75                  80 gac tcc gtg aag ggc cga ttc acc atc tcc aga gac aat tcc aag aac     288
Asp Ser Val Lys Gly Arg Phe Thr Ile Ser Arg Asp Asn Ser Lys Asn
                 85                  90                  95 acg ctg tat ctg caa atg aac agc ctg aga gct gag gac acg gct gtg     336
Thr Leu Tyr Leu Gln Met Asn Ser Leu Arg Ala Glu Asp Thr Ala Val
            100                 105                 110 tat tac tgt gcg aga gat cgg cac tcc tac gat ttt tgg agt ggg tcc     384
Tyr Tyr Cys Ala Arg Asp Arg His Ser Tyr Asp Phe Trp Ser Gly Ser
        115                 120                 125 ctt gac tac tgg ggc cag gga acc ctg gtc acc gtc tca tca gct agt     432
Leu Asp Tyr Trp Gly Gln Gly Thr Leu Val Thr Val Ser Ser Ala Ser
    130                 135                 140 acc aag ggc cca tcg gtc ttc ccc ctg gca ccc tcc tcc aag agc acc     480
Thr Lys Gly Pro Ser Val Phe Pro Leu Ala Pro Ser Ser Lys Ser Thr
145                 150                 155                 160 tct ggg ggc aca gcg gcc ctg ggc tgc ctg gtc aag gac tac ttc ccc     528
Ser Gly Gly Thr Ala Ala Leu Gly Cys Leu Val Lys Asp Tyr Phe Pro
                165                 170                 175 gaa ccg gtg acg gtg tcg tgg aac tca ggc gcc ctg acc agc ggc gtg     576
Glu Pro Val Thr Val Ser Trp Asn Ser Gly Ala Leu Thr Ser Gly Val
            180                 185                 190 cac acc ttc ccg gct gtc cta cag tcc tca gga ctc tac tcc ctc agc     624
His Thr Phe Pro Ala Val Leu Gln Ser Ser Gly Leu Tyr Ser Leu Ser
        195                 200                 205 agc gtg gtg acc gtg ccc tcc agc agc ttg ggc acc cag acc tac atc     672
```

```
                                                                              -continued Ser Val Val Thr Val Pro Ser Ser Leu Gly Thr Gln Thr Tyr Ile
    210                 215                 220 tgc aac gtg aat cac aag ccc agc aac acc aag gtg gac aag aaa gtt      720
Cys Asn Val Asn His Lys Pro Ser Asn Thr Lys Val Asp Lys Lys Val
225                 230                 235                 240 gag ccc aaa tct tgt gac aaa act cac aca tgc cca ccg tgc cca gca      768
Glu Pro Lys Ser Cys Asp Lys Thr His Thr Cys Pro Pro Cys Pro Ala
                245                 250                 255 cct gaa ctc ctg ggg gga ccg tca gtc ttc ctc ttc ccc cca aaa ccc      816
Pro Glu Leu Leu Gly Gly Pro Ser Val Phe Leu Phe Pro Pro Lys Pro
            260                 265                 270 aag gac acc ctc atg atc tcc cgg acc cct gag gtc aca tgc gtg gtg      864
Lys Asp Thr Leu Met Ile Ser Arg Thr Pro Glu Val Thr Cys Val Val
        275                 280                 285 gtg gac gtg agc cac gaa gac cct gag gtc aag ttc aac tgg tac gtg      912
Val Asp Val Ser His Glu Asp Pro Glu Val Lys Phe Asn Trp Tyr Val
    290                 295                 300 gac ggc gtg gag gtg cat aat gcc aag aca aag ccg cgg gag gag cag      960
Asp Gly Val Glu Val His Asn Ala Lys Thr Lys Pro Arg Glu Glu Gln
305                 310                 315                 320 tac aac agc acg tac cgg gtg gtc agc gtc ctc acc gtc ctg cac cag     1008
Tyr Asn Ser Thr Tyr Arg Val Val Ser Val Leu Thr Val Leu His Gln
                325                 330                 335 gac tgg ctg aat ggc aag gag tac aag tgc aag gtc tcc aac aaa gcc     1056
Asp Trp Leu Asn Gly Lys Glu Tyr Lys Cys Lys Val Ser Asn Lys Ala
            340                 345                 350 ctc cca gcc ccc atc gag aaa acc atc tcc aaa gcc aaa ggg cag ccc     1104
Leu Pro Ala Pro Ile Glu Lys Thr Ile Ser Lys Ala Lys Gly Gln Pro
        355                 360                 365 cga gaa cca cag gtg tac acc ctg ccc cca tcc cgg gat gag ctg acc     1152
Arg Glu Pro Gln Val Tyr Thr Leu Pro Pro Ser Arg Asp Glu Leu Thr
    370                 375                 380 aag aac cag gtc agc ctg acc tgc ctg gtc aaa ggc ttc tat ccc agc     1200
Lys Asn Gln Val Ser Leu Thr Cys Leu Val Lys Gly Phe Tyr Pro Ser
385                 390                 395                 400 gac atc gcc gtg gag tgg gag agc aat ggg cag ccg gag aac aac tac     1248
Asp Ile Ala Val Glu Trp Glu Ser Asn Gly Gln Pro Glu Asn Asn Tyr
                405                 410                 415 aag acc acg cct ccc gtg ctg gac tcc gac ggc tcc ttc ttc ctc tac     1296
Lys Thr Thr Pro Pro Val Leu Asp Ser Asp Gly Ser Phe Phe Leu Tyr
            420                 425                 430 agc aag ctc acc gtg gac aag agc agg tgg cag cag ggg aac gtc ttc     1344
Ser Lys Leu Thr Val Asp Lys Ser Arg Trp Gln Gln Gly Asn Val Phe
        435                 440                 445 tca tgc tcc gtg atg cat gag gct ctg cac aac cac tac acg cat aag     1392
Ser Cys Ser Val Met His Glu Ala Leu His Asn His Tyr Thr His Lys
    450                 455                 460 agc ctc tcc ctg tct ccg ggt aaa tga                                 1419
Ser Leu Ser Leu Ser Pro Gly Lys
465                 470

<210> SEQ ID NO 130
<211> LENGTH: 472
<212> TYPE: PRT
<213> ORGANISM: Homo sapiens

<400> SEQUENCE: 130

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Val Val Gln
```

-continued

```
                 20                  25                  30
Pro Gly Arg Ser Leu Arg Leu Ser Cys Ala Ala Ser Gly Phe Thr Phe
             35                  40                  45
Ser Ser Tyr Ala Met His Trp Val Arg Gln Ala Pro Gly Lys Gly Leu
         50                  55                  60
Glu Trp Val Ala Val Ile Ser Tyr Asp Gly Ser Asn Lys Tyr Tyr Ala
 65                  70                  75                  80
Asp Ser Val Lys Gly Arg Phe Thr Ile Ser Arg Asp Asn Ser Lys Asn
                 85                  90                  95
Thr Leu Tyr Leu Gln Met Asn Ser Leu Arg Ala Glu Asp Thr Ala Val
            100                 105                 110
Tyr Tyr Cys Ala Arg Asp Arg His Ser Tyr Asp Phe Trp Ser Gly Ser
            115                 120                 125
Leu Asp Tyr Trp Gly Gln Gly Thr Leu Val Thr Val Ser Ser Ala Ser
            130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
            195                 200                 205
Ser Val Val Thr Val Pro Ser Ser Leu Gly Thr Gln Thr Tyr Ile
            210                 215                 220
Cys Asn Val Asn His Lys Pro Ser Asn Thr Lys Val Asp Lys Lys Val
225                 230                 235                 240
Glu Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
            275                 280                 285
Val Asp Val Ser His Glu Asp Pro Glu Val Lys Phe Asn Trp Tyr Val
            290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
            355                 360                 365
Arg Glu Pro Gln Val Tyr Thr Leu Pro Pro Ser Arg Asp Glu Leu Thr
            370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
            435                 440                 445
```

```
Ser Cys Ser Val Met His Glu Ala Leu His Asn His Tyr Thr His Lys
    450                 455                 460
Ser Leu Ser Leu Ser Pro Gly Lys
465                 470

<210> SEQ ID NO 131
<211> LENGTH: 705
<212> TYPE: DNA
<213> ORGANISM: Homo sapiens
<220> FEATURE:
<221> NAME/KEY: CDS
<222> LOCATION: (1)..(705)
<223> OTHER INFORMATION:

<400> SEQUENCE: 131 atg gcg ttg cag acc cag gtc ttc att tct ctg ttg ctc tgg atc tct          48
Met Ala Leu Gln Thr Gln Val Phe Ile Ser Leu Leu Leu Trp Ile Ser
1               5                   10                  15 ggt gcc tac ggg gac atc gtg atg acc cag tct cct tcc acc ctg tct          96
Gly Ala Tyr Gly Asp Ile Val Met Thr Gln Ser Pro Ser Thr Leu Ser
            20                  25                  30 gca tct gta gga gac aga gtc acc atc act tgc cgg gcc agt cag agt         144
Ala Ser Val Gly Asp Arg Val Thr Ile Thr Cys Arg Ala Ser Gln Ser
        35                  40                  45 att agt agc tgg ttg gcc tgg tat cag cag aaa cca ggg aaa gcc cct         192
Ile Ser Ser Trp Leu Ala Trp Tyr Gln Gln Lys Pro Gly Lys Ala Pro
    50                  55                  60 aag ctc ctg atc tat aag gca tct agt tta gaa agt ggg gtc cca tca         240
Lys Leu Leu Ile Tyr Lys Ala Ser Ser Leu Glu Ser Gly Val Pro Ser
65                  70                  75                  80 agg ttc agc ggc agt gga tct ggg aca gaa ttc act ctc acc atc agc         288
Arg Phe Ser Gly Ser Gly Ser Gly Thr Glu Phe Thr Leu Thr Ile Ser
                85                  90                  95 agc ctg cag cct gat gat ttt gca act tat tac tgc caa cag tat aat         336
Ser Leu Gln Pro Asp Asp Phe Ala Thr Tyr Tyr Cys Gln Gln Tyr Asn
            100                 105                 110 agt tat tct aac act ttt ggc cag ggg acc aag ctg gag atc aaa cgt         384
Ser Tyr Ser Asn Thr Phe Gly Gln Gly Thr Lys Leu Glu Ile Lys Arg
        115                 120                 125 acc gtg gct gca cca tct gtc ttc atc ttc ccg cca tct gat gag cag         432
Thr Val Ala Ala Pro Ser Val Phe Ile Phe Pro Pro Ser Asp Glu Gln
    130                 135                 140 ttg aaa tct gga act gcc tct gtt gtg tgc ctg ctg aat aac ttc tat         480
Leu Lys Ser Gly Thr Ala Ser Val Val Cys Leu Leu Asn Asn Phe Tyr
145                 150                 155                 160 ccc aga gag gcc aaa gta cag tgg aag gtg gat aac gcc ctc caa tcg         528
Pro Arg Glu Ala Lys Val Gln Trp Lys Val Asp Asn Ala Leu Gln Ser
                165                 170                 175 ggt aac tcc cag gag agt gtc aca gag cag gac agc aag gac agc acc         576
Gly Asn Ser Gln Glu Ser Val Thr Glu Gln Asp Ser Lys Asp Ser Thr
            180                 185                 190 tac agc ctc agc agc acc ctg acg ctg agc aaa gca gac tac gag aaa         624
Tyr Ser Leu Ser Ser Thr Leu Thr Leu Ser Lys Ala Asp Tyr Glu Lys
        195                 200                 205 cac aaa gtc tac gcc tgc gaa gtc acc cat cag ggc ctg agc tcg ccc         672
His Lys Val Tyr Ala Cys Glu Val Thr His Gln Gly Leu Ser Ser Pro
    210                 215                 220 gtc aca aag agc ttc aac agg gga gag tgt tag                             705
Val Thr Lys Ser Phe Asn Arg Gly Glu Cys
225                 230
```

```
<210> SEQ ID NO 132
<211> LENGTH: 234
<212> TYPE: PRT
<213> ORGANISM: Homo sapiens

<400> SEQUENCE: 132

Met Ala Leu Gln Thr Gln Val Phe Ile Ser Leu Leu Leu Trp Ile Ser
1               5                   10                  15

Gly Ala Tyr Gly Asp Ile Val Met Thr Gln Ser Pro Thr Leu Ser
            20                  25                  30

Ala Ser Val Gly Asp Arg Val Thr Ile Thr Cys Arg Ala Ser Gln Ser
            35                  40                  45

Ile Ser Ser Trp Leu Ala Trp Tyr Gln Gln Lys Pro Gly Lys Ala Pro
        50                  55                  60

Lys Leu Leu Ile Tyr Lys Ala Ser Ser Leu Glu Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Asp Asp Phe Ala Thr Tyr Tyr Cys Gln Gln Tyr Asn
                100                 105                 110

Ser Tyr Ser Asn Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

MONOCLONAL ANTIBODY AND GENE ENCODING THE SAME, HYBRIDOMA, PHARMACEUTICAL COMPOSITION, AND DIAGNOSTIC REAGENT

TECHNICAL FIELD

The present invention relates to a novel monoclonal antibody useful for diagnosis and therapy of cancer, and a DNA encoding such a monoclonal antibody, a hybridoma producing such an antibody, and a pharmaceutical composition and a diagnostic reagent, each of which contains such an antibody.

BACKGROUND ART

In the field of cancer therapy, targeting therapy against a specific type of cancer cell has been studied so far for the treatment of solid cancer on which no therapeutic agent shows sufficient effect. In such targeting therapy, a monoclonal antibody that specifically recognizes cancer cells is effective. However, the use of a mouse monoclonal antibody has some problems such as difficulty of repetitive administration because of side effects such as anaphylaxis caused by an immune response (Proc. Natl. Acad. Sci. U.S.A. vol.86, p 4220, 1989).

For solving such problems, attempts have been conducted to obtain monoclonal antibodies with reduced side effects. A technology for producing a chimeric antibody in which constant region is replaced with that of human antibody by genetic engineering, a technology for producing a humanized antibody in which all regions except for hypervariable regions are replaced with those of human antibody, etc. are known. However, a complete human monoclonal antibody has been desired from the viewpoint of reducing side effects. As a method of obtaining a complete human monoclonal antibody, there is a hybridoma method using a lymphocyte derived from human (Cancer Res. vol.45, p 263, 1985). Although there is a few report about a human monoclonal antibody that reacts cancer cells (JP3236667 etc.), preparation of human monoclonal antibodies which adequately react with cancer cells has been still very difficult because of the reasons that it is very difficult to conduct passive immunity for the purpose of obtaining human B cells which produce a desired antibody, and that any efficient methodology which allows infinite reproduction of antibody-producing cells has not been established yet.

Even under such circumstances, some monoclonal antibodies which exhibit a killing-effect or anti-proliferative effect on specific cancer cells by itself or in combination with anti-cancer drugs have been developed using a humanized antibody technology or the like. In recent years, application of an anti-Her2-humanized antibody HERCEPTIN™) to breast cancer (Oncology vol. 63 Suppl 1, pp 25-32, 2002), clinical trials using an anti-EGF receptor antibody (Semin Oncol. vol. 29, No. 5 Suppl 14, pp 18-30, 2002), or an anti-VEGF (vascular endothelial growth factor) antibody (Semin Oncol. vol. 29, No. 6 Suppl 16, pp 10-14, 2002), and the like have been reported. However, any antibody, which can be used for targeting therapy for cancers including a non-small cell lung cancer from which many patients are suffering or refractory cancers such as pancreatic cancer, has not yet been developed. For treating such types of cancer, the acquisition of a monoclonal antibody having high specificity to cancer tissue with reduced side effects has been desired.

Vimentin is a cytoskeletal filament protein of a mesenchymal or nonepithelial cell, and it is known that its gene expression increases upon cell stimulation (Mol Cell Biol. 1987, vol. 7, No. 11, p3908-15). In addition, it is known that the expression of vimentin is not found in normal epithelial cells, whereas high expression of vimentin is found in cytoplasm of some poorly-differentiated tumor cells such as those of pulmonary adenocarcinoma, gastric cancer, endometrial carcinoma, or embryonal cell carcinoma (Mol Cell Biol. 1987, vol. 7, No. 11, p 3908-15). However, a phenomenon that vimentin functions as an antigenic protein has not been known.

SUMMARY OF THE INVENTION

An object of the present invention is to provide a monoclonal antibody useful for diagnosis and treatment of cancer, particularly of non-small cell lung cancer, pancreatic cancer, and gastric cancer with reduced side effects.

The inventors of the present invention have made extensive studies to provide a monoclonal antibody that can be used in targeting therapy on cancer tissues. As a result, they prepared hybridoma cells that produce a novel human monoclonal antibody capable of specifically recognizing cancer cells such as HLC-1, PANC-1 or MKN45, and found that anti-cancer drug useful in targeting therapy can be obtained by using such an antibody. Accordingly, they completed the present invention.

That is, the present invention provides the followings.

(1) A monoclonal antibody, wherein variable region of heavy chain of said monoclonal antibody comprises amino acid sequences of SEQ ID NOS: 86, 88 and 90.

(2) The monoclonal antibody according to (1), wherein the variable region of the heavy chain comprises an amino acid sequence of SEQ ID NO: 82.

(3) The monoclonal antibody according to (1), wherein the variable region of the heavy chain comprises an amino acid sequence of SEQ ID NO: 115.

(4) A monoclonal antibody, wherein variable region of the light chain of said monoclonal antibody comprises amino acid sequences of SEQ ID NOS: 92, 94 and 96.

(5) The monoclonal antibody according to (4), wherein the variable region of the light chain comprises an amino acid sequence of SEQ ID NO: 84.

(6) The monoclonal antibody according to (4), wherein the variable region of the light chain comprises an amino acid sequence of SEQ ID NO: 117.

(7) A monoclonal antibody, wherein variable region of the heavy chain of said monoclonal antibody comprises amino acid sequences of SEQ ID NOS: 86, 88 and 90, and variable region of the light chain of said monoclonal antibody comprises amino acid sequences of SEQ ID NOS: 92, 94 and 96.

(8) The monoclonal antibody according to (7), wherein the variable region of the heavy chain contains an amino acid sequence of SEQ ID NO: 82, and the variable region of the light chain comprises an amino acid sequence of SEQ ID NO: 84.

(9) The monoclonal antibody according to (7), wherein the variable region of the heavy chain comprises an amino acid sequence of SEQ ID NO: 115, and the variable region of the light chain comprises an amino acid sequence of SEQ ID NO: 117.

(10) The monoclonal antibody according to any one of (1) to (9), wherein said monoclonal antibody is a human antibody.

(11) A DNA which encodes the monoclonal antibody according to any one of (1) to (10).

(12) The DNA according to (11), wherein a region that encodes variable region of the heavy chain comprises nucleotide sequences of SEQ ID NOS: 85, 87 and 89, and a region that encodes variable region of the light chain comprises nucleotide sequences of SEQ ID NOS: 91, 93 and 95.

(13) The DNA according to (11) or (12), wherein the region that encodes the variable region of the heavy chain comprises a nucleotide sequence of SEQ ID NO: 81, and the region that encodes the variable region of the light chain comprises a nucleotide sequence of SEQ ID NO: 83.

(14) The DNA according to (11) or (12), wherein a region that encodes the variable region of the heavy chain comprises a nucleotide sequence of SEQ ID NO: 114, and a region that encodes the variable region of the light chain comprises a nucleotide sequence of SEQ ID NO: 116.

(15) A recombinant vector, comprising the DNA according to any one of (11) to (14).

(16) A transformant, comprising the recombinant vector according to (15).

(17) A hybridoma which produces the monoclonal antibody according to any one of (1) to (10).

(18) A pharmaceutical composition, comprising the monoclonal antibody according to any one of (1) to (10).

(19) The pharmaceutical composition according to (18), which is a composition for cancer treatment.

(20) The pharmaceutical composition according to (19), wherein the composition for cancer treatment is a composition for treatment of one or two or more cancers selected from the group consisting of non-small cell lung cancer, pancreatic cancer and gastric cancer.

(21) The pharmaceutical composition according to any one of (18) to (20), wherein the monoclonal antibody is anchored on a surface of a liposome in which a toxin or an anti-cancer drug is encapsulated.

(22) A diagnostic reagent, which comprises the monoclonal antibody according to any one of (1) to (10).

(23) A polypeptide, having the properties of the following (a) and/or (b)
(a) having a reactivity to a cytoskeleton filament,
(b) causing no morphological change against normal cells, and causing a morphological change against cancer cells.

(24) A polypeptide, having the properties of the following (a) and/or (b)
(a) specifically recognizing a protein with a molecular weight of approximately 55 kDa that is derived from a human pancreatic cancer cell line PANC-1 and comprises an amino acid sequence of SEQ ID NO: 107;
(b) causing no morphological change against normal cells, and causing a morphological change against cancer cells.

(25) The polypeptide according to (24), wherein the protein with a molecular weight of approximately 55 kDa is vimentin.

(26) The polypeptide according to any one of (23) to (25), wherein the morphological change is a morphological change to one or more cell morphology selected from an axonal-like morphology, fibroblast-like morphology and neuronal cell-like morphology with neurites.

(27) The polypeptide according to any one of (23) to (26), wherein the polypeptide is the monoclonal antibody according to any one of (1) to (10).

(28) A pharmaceutical composition, comprising the polypeptide according to any one of (23) to (26).

BRIEF DESCRIPTION OF THE DRAWINGS

FIG. 1 depicts the cultured cancer cell line HLC-1 without (A) or with (B) HoAKs-1 antibody; the cultured cancer cell line PANC1 without (C) or with (D) HoAKs-1 antibody; the cultured cancer cell line MKN45 without (E) or with (F) HoAKs-1 antibody; and the cultured cancer cell line HUVECs without (G) or with (H) HoAKs-1 antibody.

FIG. 7 depicts the cultured cancer cell line PANC1 with HoAKs-1 antibody (A) or with human IgM antibody (B); the cultured cancer cell line HLC-1 with HoAKs-1 antibody (C) or with human IgM antibody (D); and the cultured cancer cell line HUVECs with HoAKs-1 antibody (E) or with human IgM antibody (F).

FIG. 8 depicts the cultured cancer cell line PANC1 with antibody derived from the 2F6-1 cell line (A), with antibody derived from the 3F9-1 cell line (B), or with mouse IgM antibody (C); the cultured cancer cell line HLC-1 with antibody derived from the 2F6-1 cell line (D), with antibody derived from the 3F9-1 cell line (E), or with mouse IgM antibody (F); and the cultured cancer cell line HUVECs with antibody derived from the 2F6-1 cell line (G), with antibody derived from the 3F9-1 cell line (H), or with mouse IgM antibody (I).

FIG. 9 depicts the cultured cancer cell line PANC1 with FITC-conjugated anti-human Ig and γ-HoA. antibody (A) or with FITC-conjugated anti-human Ig (B); the cultured cancer cell line HLC-1 with FITC-conjugated anti-human Ig and γ-HoA. antibody (C) or with FITC-conjugated anti-human Ig (D); and the cultured cancer cell line HUVECs with FITC-conjugated anti-human Ig and γ-HoA. antibody (E) or with FITC-conjugated anti-human Ig (F).

DETAILED DESCRIPTION OF THE PREFERRED EMBODIMENTS

Hereinafter, the present invention will be described in detail.

<1> Monoclonal Antibody of the Present Invention

Figure 5:
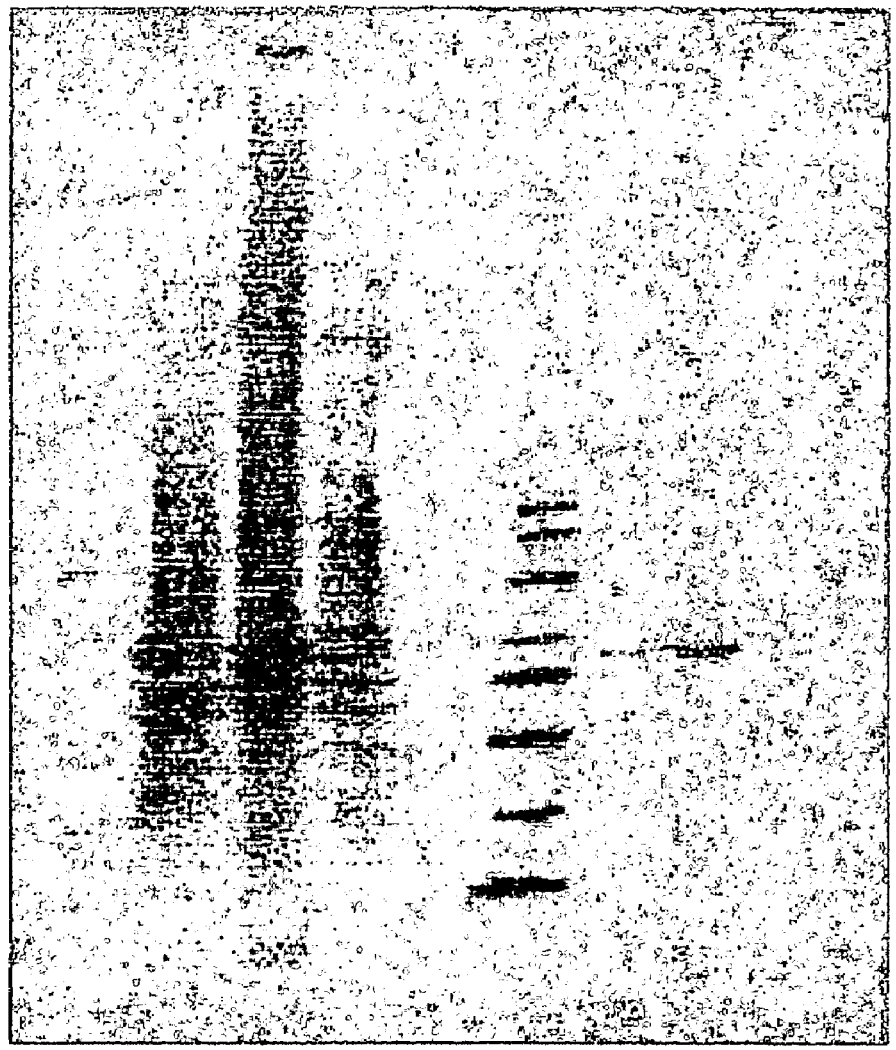
FIG. 5 is a diagram (photograph) showing the results of an analysis on an antigenic protein which the HoAKs-1 antibody recognizes.

The monoclonal antibody of the present invention is a monoclonal antibody that specifically recognizes an antigenic protein shown in FIG. 5, which is derived from a human pancreatic cancer cell line PANC-1 (ATCC No. CRL1469) and has a molecular weight of approximately 55 kDa (a protein comprising an amino acid sequence of SEQ ID NO: 107). In addition, the antibody of the present invention is a monoclonal antibody which does not cause a morphological change in normal cells but cause a morphological change in cancer cells. Furthermore, the antibody of the present invention is a monoclonal antibody that specifically recognizes the protein shown in FIG. 5, that is derived from the human pancreatic cancer cell line PANC-1 and has a molecular weight of approximately 55 kDa (a protein comprising an amino acid sequence of SEQ ID NO: 107), and does not cause a morphological change in normal cells but cause a morphological change in cancer cells. As an antigenic protein of approximately 55 kDa, vimentin can be exemplified. In addition, the term "morphological change" refers to, for example, a morphological change from a normal morphology to an axonal-like morphology, fibroblast-like morphology and a neuronal cell-like morphology with neurites as shown in B and D of FIG. 1.

Specific examples of the monoclonal antibody of the present invention include antibodies in which variable region of the heavy chain comprises amino acid sequences of SEQ ID NOS: 86, 88 and 90 and variable region of the light chain comprises amino acid sequences of SEQ ID NOS: 92, 94 and 96. In the amino acid sequence of SEQ ID NO: 88, the amino acid at position 10 may be Cys or Tyr. In other words, there are two types of variable regions of the heavy chain, one having Cys at position 10 and the other having Tyr at position 10. In addition, the antibody of the present invention may have substitution, deletion, or addition of one or several amino acids in one or more of the above six kinds of sequences as far as the antibody has the specificity that it specifically recognizes the antigenic protein with molecular weight of approximately 55 kDa (a protein comprising an amino acid sequence of SEQ ID NO: 107) derived from the human pancreatic cancer cell line PANC-1. Here, the term "several" means preferably two to five, more preferably two to three, particularly preferably two.

The above six kinds of sequences are the sequences of the regions called as "hypervariable regions" in variable regions of the heavy and light chain. An antibody consists of heavy chains and light chains, and each of these chains is composed of a constant region and a variable region. A variable region comprises hypervariable regions which determine the specificity of immunoglobulin as an antibody and the binding affinity of the antibody to an epitope. Therefore, regions other than hypervariable regions may be derived from any of other antibodies, so far as hypervariable regions of the present invention comprise each of the above sequences. Here, the term "other antibodies" includes antibodies derived from organisms other than human, but antibodies of human origin are preferable in terms of reducing side effects.

In the present invention, a particularly preferable monoclonal antibody may be one comprising an amino acid sequence of SEQ ID NO: 82 in variable region of the heavy chain and an amino acid sequence of SEQ ID NO: 84 in variable region of the light chain, or one comprising an amino acid sequence of SEQ ID NO: 115 in variable region of the heavy chain and an amino acid sequence of SEQ ID NO: 117 in variable region of the light chain. Here, in the sequence of SEQ ID NO: 82 or 115, the combination of the amino acids at positions 14 and 51 may be either (Cys, Tyr) or (Tyr, Cys). In other words, there are two kinds of the sequences of variable region of the heavy chain, one having Cys at position 14 and Tyr at position 51 and the other having Tyr at position 14 and Cys at position 51. Furthermore, the sequence of SEQ ID NO: 84 or 117 may have Val or Ile at position 13. In other words, there are two kinds of the sequences of variable region of the heavy chain, one having Val at position 13 and the other having Ile at position 13.

In the present invention, the term "monoclonal antibody" refers to any of those including monoclonal antibodies and fragments thereof, F(ab')$_2$ antibodies, F(ab') antibodies, short-chain antibodies (scFv), diabodies, and minibodies. When the monoclonal antibody contains a constant region, amino acid sequences of its constant regions of the heavy and light chains are preferably one of those described in Nucleic Acids Research vol. 14, p1779, 1986; The Journal of Biological Chemistry vol. 257, p1516, 1982; and Cell vol. 22, p197, 1980. The antibody of the present invention comprising constant and variable regions may be, for example, one comprising an amino acid sequence of SEQ ID NO: 130 (heavy chain) and SEQ ID NO: 132 (light chain).

The monoclonal antibody of the present invention can be obtained by culturing a hybridoma producing the antibody of the present invention in a culture medium, for example, a RPMI1640 medium that contains fetal bovine serum. Alternatively, it can be obtained by preparing a gene (e.g., a gene comprising SEQ ID NO: 129 (heavy chain) or 131 (light chain)), in which a DNA encoding a constant region of heavy chain or light chain is ligated to a DNA encoding each variable region (e.g. DNA comprising SEQ ID NOS: 81 or 83), by means of a PCR method or a chemical synthesis; inserting the obtained gene into a conventionally-used expression vector (e.g., pcDNA3.1 (Invitrogen)) capable of expressing the gene; expressing the gene in a host cell such as a CHO cell (Chinese hamster ovary cell) or *Escherichia coli* to produce the antibody; and purifying the obtained antibody from the culture medium using a Protein A column or the like.

Furthermore, the monoclonal antibody of the present invention may be obtained by: preparing a hybridoma from an animal immunized with a protein of molecular weight of approximately 55 kDa that is derived from the human pancreatic cancer cell line PANC-1 and comprises an amino acid sequence of SEQ ID NO: 107, preferably vimentin (GenBank Accession No. M14144); culturing the hybridoma; and selecting a monoclonal antibody which can bind to a surface of living cancer cells from the obtained monoclonal antibodies. Examples of such a monoclonal antibody include those produced from hybridoma strains 2F6-1 and 3F9-1, which will be explained in the Examples described later.

<2> DNA of the Present Invention

The DNA of the present invention is a DNA that encodes the monoclonal antibody of the present invention. Examples thereof include a DNA that comprises a region encoding variable region of the heavy chain which comprises amino acid sequences of SEQ ID NOS: 86, 88 and 90; and a region encoding variable region of light chain which comprises amino acid sequences of SEQ ID NOS: 92, 94 and 96. Preferably, such a DNA comprises a region encoding variable region of the heavy chain which comprises nucleotide sequences of SEQ ID NOS: 85, 87 and 89; and a region encoding variable region of the light chain which comprises nucleotide sequences of SEQ ID NOS: 91, 93 and 95. Here, in the sequence of SEQ ID NO: 87, the nucleotide at position 29 may be either "a" or "g". In other words, there are two types of the sequences encoding variable region of the heavy chain, one having "a" at position 29 and the other having "g" at position 29. Furthermore, in the sequence of SEQ ID NO: 95, the nucleotide at position 18 may be either "c" or "t". In other words, there are two types of the sequences encoding variable region of the light chain, one having "c" at position 18 and the other having "t" at position 18.

The hypervariable regions encoded by those DNA sequences are regions that define the specificity of the antibody, so that sequences encoding the other regions may be those derived from other antibodies. Here, the term "other antibodies" includes antibodies derived from organisms other than human, but, antibodies of human origin are preferable in terms of reducing side effect.

In the present invention, particularly preferable DNA may be one comprising a sequence encoding an amino acid sequence of SEQ ID NO: 82 in variable region of the heavy chain and a sequence encoding an amino acid sequence of SEQ ID NO: 84 in variable region of the light chain, or one comprising a sequence encoding an amino acid sequence of SEQ ID NO: 115 in variable region of the heavy chain and a sequence encoding an amino acid sequence of SEQ ID NO: 117 in variable region of the light chain. Of those, a particularly preferable DNA may be one comprising a nucleotide sequence of SEQ ID NO: 81 encoding variable region of the heavy chain and a nucleotide sequence of SEQ ID NO: 83 encoding variable region of the light chain, or one comprising a nucleotide sequence of SEQ ID NO: 114 encoding variable region of the heavy chain and a nucleotide sequence of SEQ ID NO: 116 encoding variable region of the light chain. Here, in the sequence of SEQ ID NO: 81 or 114, the combination of the nucleotides at positions 41 and 152 may be either of (a, g) or (g, a). In other words, there are two types of the sequences encoding variable region of the heavy chain, one having "a" at position 41 and "g" at position 152 and the other having "g" at position 41 and "a" at position 152. Furthermore, in the sequence of SEQ ID NO: 83 or 116, the combination of the nucleotides at positions 37, 183 and 258 may be any of (a, a, t), (a, a, c), and (g, g, t). In other words, there are three types of the sequences encoding variable region of the light chain, one having "a" at position 37, "a" at position 183 and "t" at position 258, one having "a" at position 37, "a" at position 183 and "c" at position 258, and one having "g" at position 37, "g" at position 183, and "t" at position 258.

Furthermore, the DNA of the present invention may be one which is capable of hybridizing with a DNA comprising nucleotide sequences of SEQ ID NOS: 81 and 83, or with a DNA comprising nucleotide sequence of SEQ ID NOS: 114 and 116 under stringent conditions as far as it encodes a monoclonal antibody that specifically recognizes an antigenic protein with a molecular weight of approximately 55 kDa that is derived from the human pancreatic cancer cell line PANC-1 (a protein comprising an amino acid sequence of SEQ ID NO: 107). Here, stringent conditions include those under which hybridization is performed at a salt concentration corresponding to 60° C., 1×SSC, 0.1% SDS, preferably 0.1×SSC, 0.1% SDS, which corresponds to washing conditions in Southern hybridization.

The DNA of the present invention may be one that encodes all of the constant region and variable region of heavy and light chains. Alternatively, it may be one encoding only the variable regions of the heavy and light chains. When the DNA encodes all of the constant region and variable region, the nucleotide sequences of the constant regions of the heavy and light chains are preferably those described in Nucleic Acids Research vol. 14, p1779, 1986, The Journal of Biological Chemistry vol. 257, p1516, 1982, and Cell vol. 22, p197, 1980. The DNA of the present invention, which encodes the constant region and variable region, encompasses a DNA comprising a nucleotide sequence of SEQ ID NO: 129 (heavy chain) and a nucleotide sequence of SEQ ID NO: 131 (light chain).

The DNA of the present invention can be obtained by the method described below. At first, total RNA is prepared from the cells (e.g., hybridoma cells) of the present invention using a commercially-available RNA extraction kit and then cDNA is synthesized from the total RNA by reverse transcriptase using random primers and the like. Subsequently, using the PCR method in which oligonucleotides each having a sequence conserved in a variable region of heavy chain or light chain of human antibody are used as primers, cDNA encoding such an antibody is amplified. The sequence encoding the constant region can be obtained by amplification of the known sequence by the PCR method. The nucleotide sequence of the DNA can be determined by a conventional method after inserting the DNA into a plasmid for sequence determination.

Furthermore, the present invention provides a recombinant vector comprising the DNA of the present invention, and a transformant containing the recombinant vector. The recombinant vector may be a vector which can be used for gene expression in prokaryotic cells such as *Escherichia coli* (e.g., pBR322, pUC119 or a derivative thereof), preferable is a vector which can be used for gene expression in eukaryotic cells, and more preferable is a vector which can be used for gene expression in cells derived from a mammal. Examples of the vectors which can be used for gene expression in cells derived from a mammal include a plasmid vector such as pcDNA3.1 (manufactured by Invitrogen Co., Ltd.) and a virus vector such as pDON-AI DNA (manufactured by TAKARA BIO INC.). The transformant to be introduced with the recombinant vector of the present invention may be a prokaryotic cell such as *Escherichia coli*, but preferable is a eukaryotic cell, and more preferable is a cell derived from a mammal. Examples of the cells derived from a mammal include a Chinese hamster ovary cell (CHO cell).

<3> Hybridoma of the Present Invention

The hybridoma of the present invention is a hybridoma that produces the monoclonal antibody as described above. Examples of the hybridomas of the present invention include hybridoma strains HoAKs-1, 2F6-1 and 3F9-1, which will be explained in the Examples described later. The hybridoma of the present invention can be obtained by the following method. At first, on the basis of the method of A. Imam et. al (Cancer Research vol. 45, 263, 1985), tumor-infiltrating lymphocytes are isolated from the tumor tissue removed from a patient diagnosed with lung cancer and then the cells containing the lymphocytes are fused with mouse myeloma cells using polyethylene glycol to obtain hybridoma cells. Subsequently, enzyme immunoassay is carried out using the supernatant of the obtained hybridoma and then the hybridoma cells that produce antibodies that positively react to various cancer cell lines fixed with paraformaldehyde are selected, followed by cloning the obtained hybridomas by limiting dilution. Alternatively, the hybridoma of the present invention can be also obtained by immunizing a mouse using a protein with a molecular weight of approximately 55 kDa derived from the human pancreatic cancer cell line PANC-1 (a protein comprising the amino acid sequence of SEQ ID NO: 107) shown in FIG. 5 and then fusing the resulting lymphocytes with mouse myeloma cells.

<4> Pharmaceutical Composition of the Present Invention

The pharmaceutical composition OF THE PRESENT INVENTION comprises the monoclonal antibody of the present invention together with a pharmaceutically acceptable carrier. Examples of the pharmaceutically-acceptable carriers include soluble carriers such as known buffers which can be physiologically acceptable (e.g., phosphate buffer) or solid-state carriers such as latex beads.

The pharmaceutical composition OF THE PRESENT INVENTION is suitably used as a therapeutic agent for cancer, particularly for non-small cell lung cancer, pancreatic cancer, and gastric cancer. In addition, the pharmaceutical composition of the present invention may be a composition using the cell-killing effect and anti-proliferative effect of the monoclonal antibody itself, or may be a composition for targeting an anti-cancer drug such as adriamycine to a cancer tissue by binding the anti-cancer drug to the monoclonal antibody of the present invention.

In the present invention, a particularly suitable pharmaceutical composition is one in which the antibody of the present invention is anchored on a liposome containing a toxin, an anti-cancer drug or the like. The liposome used for anchoring the antibody may be composed of a lipid bilayer. Alternatively, the liposome used may be composed of a multiple lipid layers or composed of a single lipid layer. Examples of the constituents of the liposome include phosphatidylcholine, cholesterol and phosphatidyl ethanolamine, and further include phosphatidic acid as a substance for imparting the liposome with electric charge. The ratio of those constituents is, for example, 0.3 to 1 mol, preferably 0.4 to 0.6 mol of cholesterol, 0.01 to 0.2 mol, preferably 0.02 to 0.1 mol of phosphatidylethanolamine, and 0 to 0.4 mol, preferably 0 to 0.15 mol of phosphatidic acid per 1 mol of phosphatidylcholine.

A method of producing the liposome may be any of conventional methods. For instance, it can be produced using a method (Biochimica et Biophysica Acta vol. 812, p55, 1985) in which a mixture of the lipids, from which a solvent has been removed, is emulsified by a homogenizer or the like and then subjected to freeze-thawing to obtain a multilamellar liposome, followed by adjustment of pore size of the liposome appropriately by ultrasonication, high-speed homogenization, or pressure filtration through a membrane having uniform-size pores. Preferably, the liposome has a particle size of 30 to 200 nm.

Examples of the pharmaceutical agents to be encapsulated in the liposome include: carcinostatic agents such as adriamycin, daunomycin, mitomycin, cisplatin, vincristine, epirubicin, methotrexate, 5-Fu (5-Fluorouracil) and aclacinomycin; toxins such as ricin A and diphtheria toxin; and antisense RNA. Encapsulation of the agent into liposome may be accomplished by hydration of the lipids with an aqueous solution of the agent. In addition, adriamycin, daunomycin and epirubicin may be encapsulated into the liposome by a remote-loading method using pH gradient (Cancer Res. vol. 49 p5922, 1989).

Examples of methods of anchoring the monoclonal antibody on the surface of the liposome include a method in which a purified antibody is coupled with a hydrophobic substance for anchoring the antibody on the liposome, and a method in which an antibody is cross-linked to phosphatidyl ethanolamine using glutaraldehyde. More preferable method is a method in which a liposome containing a lipid into which a maleimide group has been introduced is prepared and an anti-cancer agent or toxin is encapsulated therein, and allowing it to react with a thiolated antibody to thereby anchor the antibody on the surface of the liposome. In addition, a water-soluble polymer derivative that contains a reactive site for an amino group, and a thiol- or intrinsic thiol-group moiety can be preferably used (JP 11-152234A). On the other hand, the surface of the liposome may be modified by allowing the remaining maleimide group to react with a thiolated polyalkylene glycol moiety.

Examples of the methods for introducing a thiol-group into the antibody include a method employing N-succinimidyl-3-(2-pyridyldithio)propionate (SPDP) or compounds such as iminothiolane and mercaptoalkylimidate, which is usually used for thiolation of protein, for introducing a thiol-group to the amino group of the antibody, or a method in which an intrinsic dithiol group of the antibody is reduced to form a thiol group. The method using an intrinsic thiol group is preferable from the view point of maintaining the activity of the antibody. Furthermore, the antibody may be treated with an enzyme such as pepsin to form $F(ab')_2$ and then reduced with dithiothreitol (DTT) and the like to form $F(ab')$, which provides one to three thiol groups for binding to the liposome. The binding of the thiolated antibody to the maleimide group-containing liposome may be accomplished by reacting them in a neutral buffer at pH 6.5 to 7.5 for 2 to 16 hours.

The pharmaceutical for cancer treatment of the present invention may be formulated by any of conventional methods such as a dehydration method (JP02-502348A), a method in which a stabilizing agent to obtain a liquid formulation is added (JP64-9331A), and a lyophilization method (JP64-9331A). The pharmaceutical for cancer treatment of the present invention may be administered in intravascularly, intraperitoneally and the like, as local administrations. The dosage thereof can be optimized for the respective drugs encapsulated into the liposome. When the agent is adriamycin, the dosage of adriamycin is 50 mg/kg or less, preferably 10 mg/kg or less, and more preferably 5 mg/kg or less.

<5> Diagnostic Reagent of the Present Invention

Examples of the diagnostic reagents of the present invention include those taking advantage of the specificity of the antibody of the present invention against cancer cells, particularly a cancer diagnostic reagent comprising the antibody of the present invention, a secondary antibody, a detection substrate, and other components.

<6> Polypeptide of the Present Invention

The polypeptide of the present invention includes a polypeptide that specifically recognize a protein with molecular weight of approximately 55 kDa (a protein comprising an amino acid sequence of SEQ ID NO: 107), that is derived from a human pancreatic cancer cell line PANC-1 shown in FIG. 5. In addition, it includes a polypeptide which does not cause a morphological change in a normal cell but cause a morphological change in a cancer cell. Furthermore, it may be a polypeptide that specifically recognizes a protein with a molecular weight of approximately 55 kDa (a protein comprising an amino acid sequence of SEQ ID NO: 107) that is derived from the human pancreatic cancer cell line PANC-1 shown in FIG. 5, and does not cause a morphological change in a normal cell but cause a morphological change in a cancer cell. As the antigenic protein of approximately 55 kDa, vimentin can be exemplified. In addition, the term "morphological change" refers to, for example, the morphological change from a normal cell morphology into an axonal-like morphology, fibroblast-like morphology or a neuronal cell-like morphology with neurites as shown in B and C in FIG. 1.

Specific examples of the polypeptides of the present invention include a polypeptide which is adsorbed on PROSEP-A as explained in the Examples described later. More preferably, the monoclonal antibody of the present invention is included. The polypeptide of the present invention causes a morphological change specifically to cancer cells, so that it can be used for the manufacture of a pharmaceutical composition, particularly for treatment of cancers, such as non-small cell lung cancer, pancreatic cancer and gastric cancer.

EXAMPLES

Hereinafter, the present invention will be described in more detail with reference to examples. However, the present invention is not limited to these examples without departing from the scope of the present invention.

(1) Preparation of Hybridomas by Cell Fusion Between Infiltrating Lymphocytes from a Cancer Patient and Mouse Myeloma Cells (1)-1: Preparation of Lymphocytes A tumor tissue removed from a patient with lung cancer was cut into small masses with a scalpel, and then well suspended in a culture medium A (RPMI1640+50 µg/ml gentamicin sulfate), and the culture medium was collected (named as medium (I)). The small masses of the tumor tissue were further cut into fine pieces with a razor edge, and then cells were dispersed in fresh culture medium A by passing through a pipette. This cell suspension was centrifuged at 1,000 rpm for 5 minutes and the supernatant was collected (named as supernatant II). The medium (I) was mixed with the supernatant (II) and the mixture was centrifuged at 3,000 rpm for 5 minutes, and thereby approximately $4\times10^7$ cells containing tumor-infiltrating lymphocytes were obtained.

(1)-2: Cell Fusion

The cells containing tumor-infiltrating lymphocytes were fused to mouse myeloma cells (approximately $4\times10^7$ cells) using polyethylene glycol 1500 (Roche Diagnostics) according to a standard method (Cancer Research vol. 45, 263, 1985). The fused cells were suspended in a culture medium B (culture medium A supplemented with 10% fetal bovine serum (FCS)) so that the cell density becomes $5\times10^5$ cells/ml. The suspension was dispensed on a 96-well plate at 100 µl/well and cultured at 37° C. in $CO_2$ incubator. On the second day, the culture medium B supplemented with 10 µM hypoxanthine, 0.04 µM aminopterin and 1.6 µM thymidine (culture medium B supplemented with HAT) was added to the wells at 100 µl/well and cultured until colonies of hybridomas appeared. As a result, colonies of hybridomas appeared in 10 wells.

(2) Evaluation of Reactivity of Human Monoclonal Antibody to Cancer Cell Lines (2)-1: Cancer Cell Line and its Maintenance Using the culture supernatant of the obtained hybridomas, reactivity to fixed cancer cell lines including: a lung cancer cell line HLC-1 (Cancer vol. 67, No. 4, pp483-492, 1976; provided from Mr. Suzuki in the Medical Department of the Keio University); a gastric cancer cell line MKN45 (Japanese Journal of Cancer and Chemotherapy, vol. 5, p89, 1978; provided from IBL Co., Ltd.), and a pancreatic cancer cell line SUIT2 (provided from Mr. Iguchi in National Kyushu Cancer Center) was tested to select a hybridoma of interest. Those cancer cell lines were maintained and grown at 37° C. under 5% $CO_2$ in a culture medium D that was prepared by supplementing 5% FCS to culture medium C (D-MEM/F12+50 µg/ml gentamicin sulfate).

(2)-2: Measurement of Reactivity to Cancer Cell Lines

The above-described cancer cell lines were respectively cultured in a 96-well plate for 3 to 4 days until becoming a monolayer. After the supernatant was removed, the plate was washed once with 10 mM phosphate buffer (pH 7.4, 0.15 M NaCl: PBS) and fixed with 2% paraformaldehyde at room temperature for 20 minutes. After washing five times with PBS, the plate was added and blocked with 150 µl/well of PBS solution containing 5% BSA (bovine serum albumin). Then, the plate was washed five times with PBS and supplemented with 50 µl of the hybridoma culture supernatant to react at 37° C. for one and half hours. Next, the plate was washed five times with PBS and then added with 50 µl of a horseradish peroxidase-conjugated goat antibody against a human antibody (CAPPEL; 1,000-fold dilution) to react at 37° C. for 1 hour. Subsequently, the plate was washed with PBS containing 0.05% of Tween 20 (PBS-T) and then added with 50 µl/well of phosphate-citrate buffer containing o-phenylenediamine dihydrochloride (5.2%) and $H_2O_2$ (0.015%). Reaction was conducted at room temperature until color development was observed, followed by the measurement of absorbance at 490 nm with a microphotometer (Nihon Intermed). Cloning of hybridoma was conducted by limiting dilution of the cells obtained from the wells in which reactivity was detected, and thereby a hybridoma cell line HoAKs-1 was obtained. Hereinafter, a monoclonal antibody obtained from this cell line is referred to as a HoAKs-1 antibody.

(3) Purification and Labeling of HoAKs-1 Monoclonal Antibody (3)-1: Culture of Hybridoma HoAKs-1 and Purification of HoAKs-1 Monoclonal Antibody At first, fetal bovine serum was allowed to pass through a protein A-glass bead column (PROSEP-A) (bio PROCESSING) to prepare a serum from which substances adsorbed in the PROSEP-A were removed. The culture medium A supplemented with 7 to 10% of this serum was used to culture the hybridoma HoAKs-1. Next, the culture medium in which the hybridoma HoAKs-1 had been cultured was loaded onto the PROSEP-A to thereby adsorb a PROSEP-A-adsorbed polypeptide, which was then eluted to purify the PROSEP-A-adsorbed polypeptide. This PROSEP-A-adsorbed polypeptide was used as a HoAKs-1 antibody in the subsequent procedures. It was considered that the use of the above-described serum in culture enabled to provide the purified HoAKs-1 antibody with no contamination of substances adsorbed in the PROSEP-A such as antibodies derived from serum. The HoAKs-1 antibody was confirmed to be pure IgM by sodium dodecyl sulfate-polyacrylamide gel electrophoresis (SDS-PAGE) (data not shown).

(3)-2: Biotinylation of HoAKs-1 Antibody

After the HoAKs-1 antibody purified with the PROSEP-A was biotinylated with a biotinylation reagent (Amersham Biosciences) according to the manufacturer's instructions, the labeled antibody was separated from free biotin by gel filtration method.

(4) Analysis of Effects on Living Cancer Cell Lines and Vascular Endothelial Cells (4)-1: Cancer Cell Lines and Vascular Endothelial Cells and their Maintenance A lung cancer cell line HLC-1, a gastric cancer cell line MKN45, and a pancreatic cancer cell line PANC-1 (ATCC No. CRL1469) as human cancer cell lines and vascular endothelial cells HUVECs (DAINIPPON PHARMACEUTICAL Co., Ltd.) as a normal human cell were used. Those cancer cell lines were cultured and grown in the culture medium D at 37° C. under 5% $CO_2$. The human vascular endothelial cell HUVECs was cultured and grown using CS-C culture medium (Cell SYSTEMS).

(4)-2: Analysis of Effects on Morphology of Cancer Cell Lines and Vascular Endothelial Cells The HoAKs-1 antibody was sterilized by filtration. The resulting HoAKs-1 antibody was diluted with the culture medium C or the CS-C culture medium to have a concentration of approximately 140 µg/ml, and dispensed into a 96-well plate at 100 µl/well. Next, each of the cultured cancer cells and vascular endothelial cell HUVECs was diluted to a density of $3\times10^4$ cells/ml with the culture medium C or the CSC-culture medium containing 10% human serum (ICN Biomedicals). The cell suspension was dispensed on a plate at 100 µl/well so that the number of cells in each well became 1.5×10³ cells/well and the concentration of the HoAKs-1 antibody became approximately 70 µg/ml. The plate was incubated at 37° C. under 5% $CO_2$. The culture supernatant was changed by the same medium as described above once every other day, three times in total. On the sixth day, morphological changes of the cells were observed under a light microscope.

Figure 1:
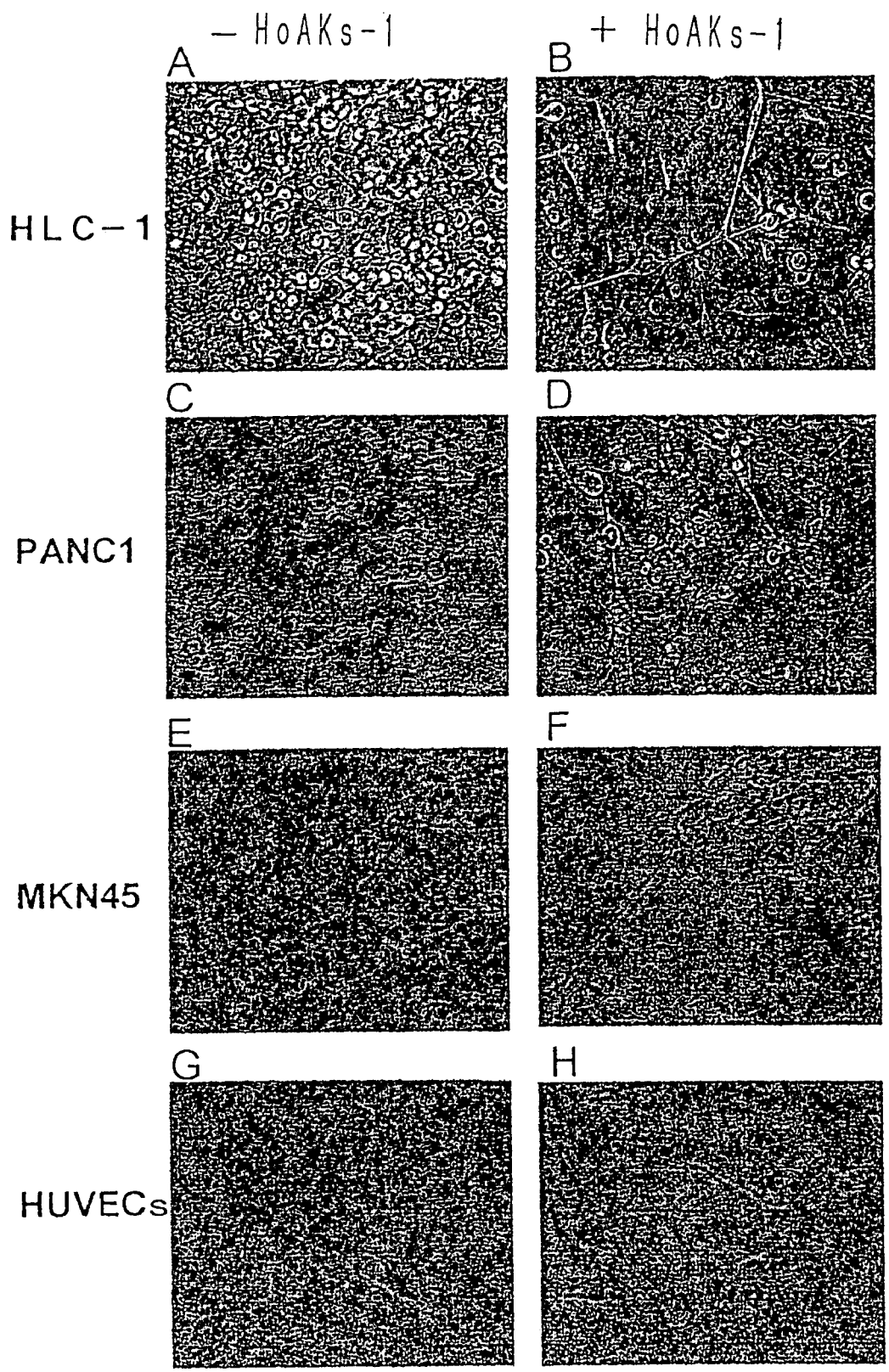
FIG. 1 is a diagram (photograph) showing a morphological change of each cell when HoAKs-1 antibody is added to cultured cancer cell lines.

The result of observation is shown in FIG. 1. No cytomorphological change by the addition of the antibody was observed in the vascular endothelial cells HUVECs as a normal cell (FIGS. 1-G and 1-H), while remarkable morphological changes by the addition of the antibody were observed in the lung cancer cell line HLC-1 (FIGS. 1-A and 1-B) and the pancreatic cancer cell line PANC-1 (FIGS. 1-C and 1-D). Those cells were changed into axon-like morphology, fibroblast-like morphology, or neuronal cell-like morphology with protrusion. Especially, the pancreatic cancer cell line PANC-1 exhibited morphological changes similar to those observed in starved condition. Moreover, slight morphological changes were observed in the gastric cancer cell line MKN45 (FIGS. 1-E and 1-F). From the above observations, the possibility that the HoAKs-1 antibody had some effects on the cancer cell lines was suggested.

(4)-3: Analysis of Anti-Proliferative Effect on Cancer Cell Lines

The lung cancer cell line HLC-1 and the gastric cancer cell line MKN45 in which morphological changes had been observed and the vascular endothelial cell HUVECs as a normal cell in which no morphological change had been observed were seeded on a 96-well plate under the same conditions, and cultured at 37° C. under 5% $CO_2$ in the presence of approximately 70 µg/ml of the HoAKs-1 antibody; the culture supernatant was changed by the same medium as described above once every other day, three times in total; and on the 6th day, the number of living cancer cells was compared by MTT assay (J. Immunol. Methods vol. 70, p257, 1984). As a control, human antibody IgM (CHEMICON) was used to conduct the same experiment.

Figure 2:
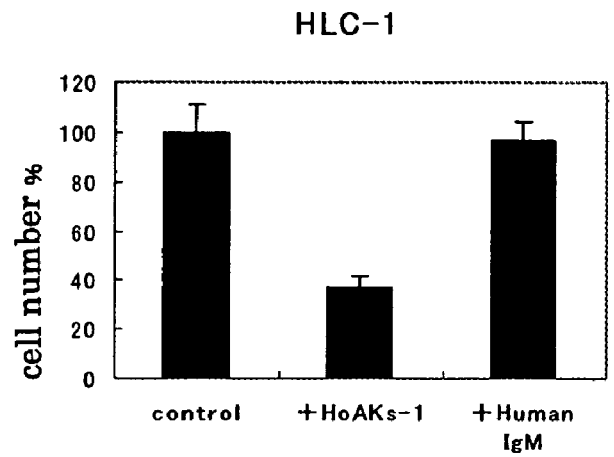
FIG. 2 is a diagram showing anti-proliferative effects of the HoAKs-1 antibody on the cultured cancer cell lines HLC-1, MKN45, and HUVECs.
Figure 2:
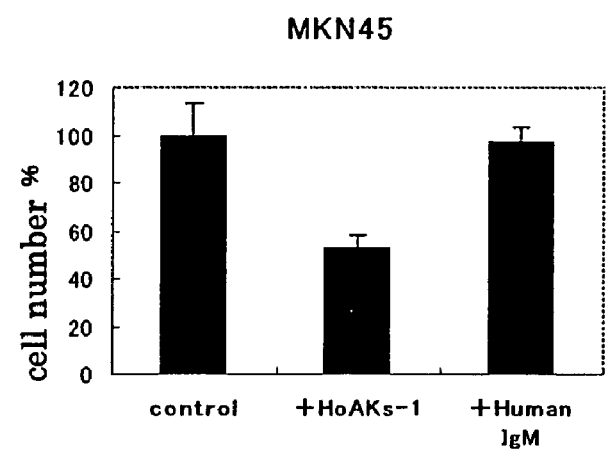
Figure 2:
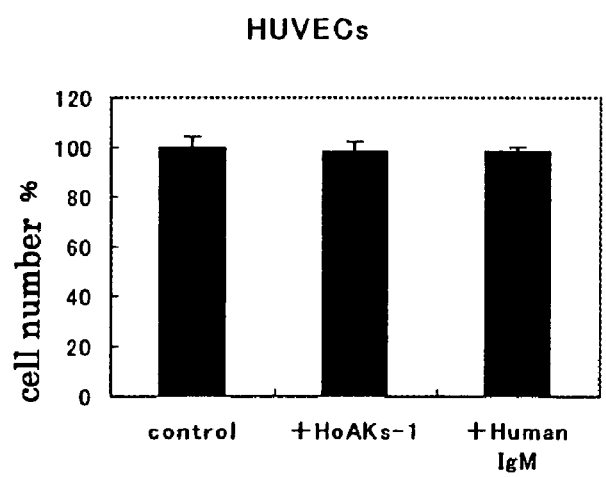

The result is shown in FIG. 2. When the number of cells under control conditions without the addition of the antibody was defined as 100%, approximately 60% and approximately 50% anti-proliferative effects were observed in the lung cancer cell line HLC-1 and the gastric cancer cell line MKN45, respectively, by the addition of the HoAKs-1 antibody. On the other hand, no difference was observed in the vascular endothelial cell HUVECs. Moreover, no anti-proliferative effect on the cancer cell lines by the addition of the antibody was observed when the human IgM was used as a control.

The cancer cell line PANC-1 in which morphological changes had been observed was seeded on a 96-well plate at 1×10³ cells/well and cultured at 37° C. under 5% $CO_2$ in the presence of 300 µg/ml, 100 µg/ml or 30 µg/ml of the HoAKs-1 antibody, respectively. The culture supernatant was changed by the same medium as described above once every other day, three times in total. On the 6th day, the number of living cancer cells was compared using a bromodeoxyuridin (BrdU) cell proliferation assay kit (Oncogene). On the 6th day, the BrdU solution was added to each well according to the instructions of the kit and cells were cultured overnight, and the amount of BrdU uptaken by the living cancer cells was measured on the 7th day. For control, human IgM was used to conduct the same experiment.

Figure 3:
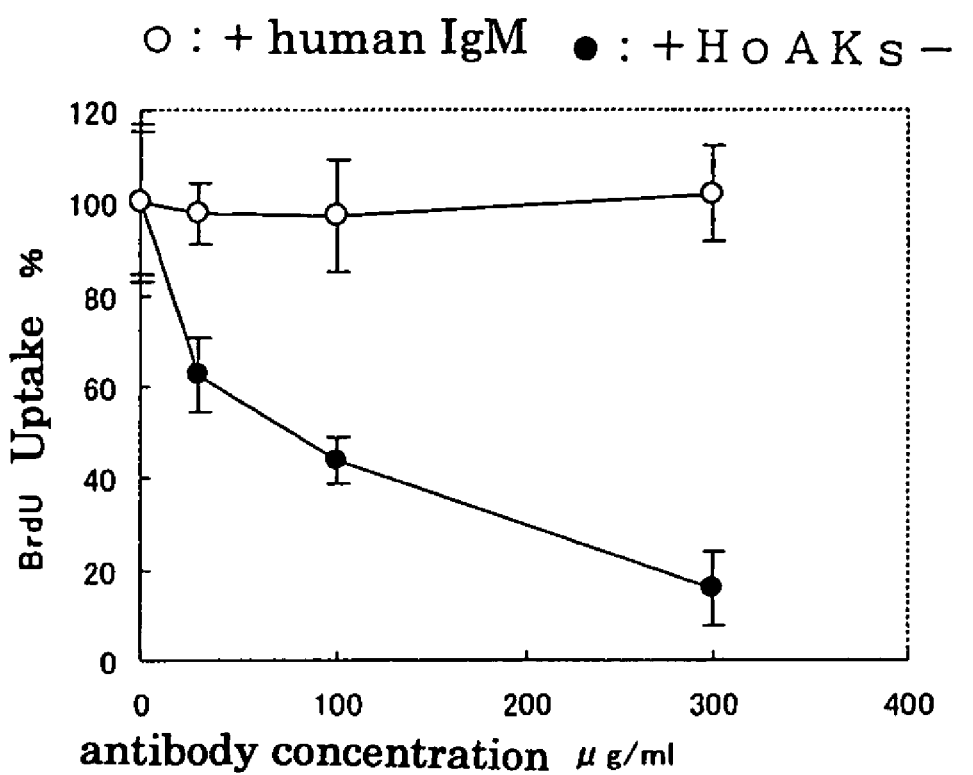
FIG. 3 is a diagram showing anti-proliferative effects of the HoAKs-1 antibody on the pancreatic cancer cell line PANC-1.

The result is shown in FIG. 3. The amount of BrdU uptaken under control conditions without the addition of the antibody was indicated by 100%. It was confirmed that the proliferation of the pancreatic cancer cell line PANC-1 was suppressed in a concentration-dependent manner by the HoAKs-1 antibody. No anti-proliferative effect on the cancer cell lines by the addition of the antibody was observed when the IgM was used as a control.

(5) Analysis of Reactivity to Various Tissue Sections (5)-1: Preparation of Various Tissue Sections Lung cancer tissue sections from which the lymphocytes used for preparation of the HoAKs-1-producing hybridoma had been derived, and noncancerous lung tissue sections surrounding the same cancer tissue were fixed in formalin solution according to a standard method and embedded in paraffin to prepare tissue sections. In addition, various cancer cell lines (lung cancer cell lines: HLC-1 (Keio University), A549 and PC9 (IBL); pancreatic cancer cell lines: SUIT2 (Kyushu Cancer Center), PANC-1 and PK8 (the Cell Resource Center for Biomedical Research; the Institute of Development, Aging and Cancer of the Tohoku University); gastric cancer cell lines: MKN45, MKN74, and HSC-3 (all of which from IBL Co., Ltd.); and colon cancer cell lines: HT29 (ATCC No. HTB38), DLD-1 (ATCC No. CCL221), LoVo (ATCC No. CCL229), and COLO205 (ATCC No. CCL222)) were respectively grown in the culture medium D at 37° C. under 5% $CO_2$ and transplanted at approximately 1×10⁶ to 1×10⁷ cells subcutaneously in nude mice (CLEA Japan, Inc.) to form tumors. The formed tumors were extracted and tumor tissue sections were prepared in the same way as described above.

(5)-2: Detection of Reactivity to Various Tissue Sections

After the prepared various tissue sections were subjected to deparaffinization and blocking procedures according to a standard method, the resulting tissue sections were reacted with the biotinylated HoAKs-1 antibody described in Example (3)-2. DAKO Catalyzed Signal Amplification (CSA) System (DAKO) was used for detection, and reactivity was detected as reddish brown stain by diaminobenzidine. For the immunostained tissue sections, cell nuclei in the tissues were stained in blue with hematoxylin in order to obtain tissue images.

Figure 4:
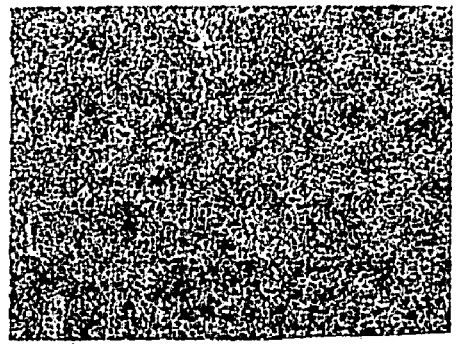
FIG. 4 is a diagram (photograph) showing the reactivity of the HoAKs-1 antibody to various tissue slices.
Figure 4:
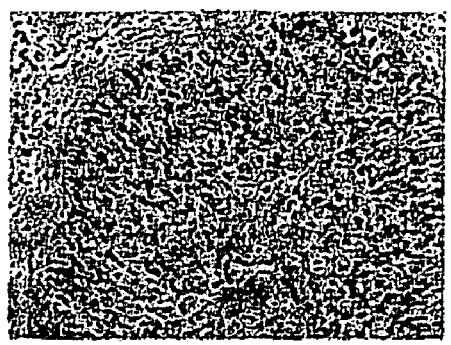
Figure 4:
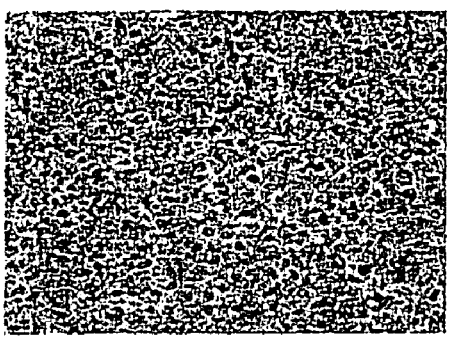
Figure 4:
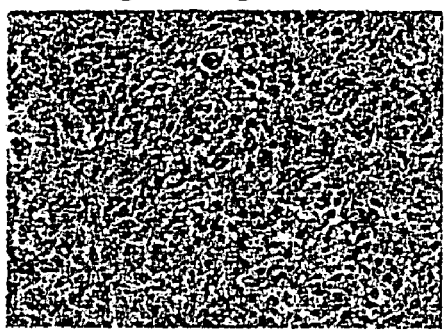
Figure 4:
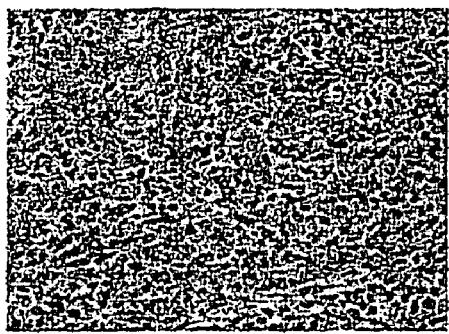
Figure 4:
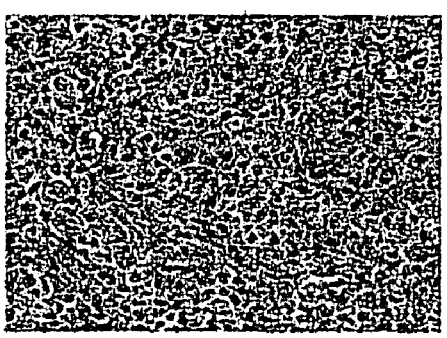
Figure 4:
Figure 4:
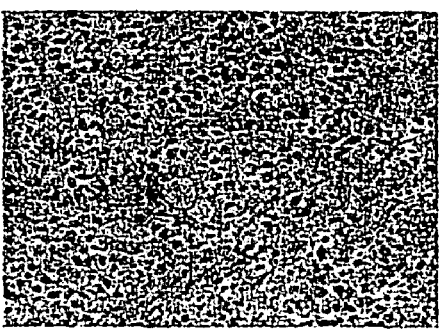

The stained images of various tumor tissue sections in which reactivity was observed and tissue sections from the autologous lung noncancerous portion are shown in FIG. 4. It was found that the HoAKs-1 antibody exhibits strong reactivity to the tumor cells in the tissue sections of autologous lung-cancer from which the hybridoma had been derived, and against the tumor cells formed in the nude mice including lung cancer cell line-mediated tumors such as HLC-1 and A549, the pancreatic cancer cell line-mediated tumors such as SUIT2, PANC-1 and PK-8, and the gastric cancer cell line-mediated tumor such as MKN45. On the other hand, no reactivity was observed against the tissue sections from the noncancerous portion.

Although not shown in FIG. 4, staining was also conducted in the same procedures as described above by using, as a control, a human antibody purified from human serum with the PROSEP-A column in the same way as the HoAKs-1 or by using an IgM-type human monoclonal antibody A having the same subtype as the HoAKs-1 antibody, which was obtained in the same way. Those antibodies had no reactivity to the insoluble fraction of the PANC-1 cell as described below nor specific reactivity to each of the tissue sections as described above.

(6) Analysis of an Antigen Recognized by HoAKs-1 Antibody (6)-1: Preparation of Antigen Sample from Cancer Cell Line Using proteins derived from the pancreatic cancer cell line PANC-1 that showed remarkable morphological changes and was confirmed to have reactivity to the antibody in the tumor formed by transplanting the cell line in the nude mouse, substances with which the HoAKs-1 antibody reacted was identified by Western blotting. The pancreatic cancer cell line PANC-1 was grown in a flask at 37° C. under 5% $CO_2$. The culture supernatant in the flask was removed and the cells were washed once with PBS. A small amount of PBS was then added to the flask and the cells were removed with a cell scraper and transferred to a centrifuge tube, followed by the collection of the cells by centrifugation at 1,000 rpm for 5 minutes. After washing twice with PBS, TNE-buffer (10 mM Tris-HCL (pH 7.6), 150 mM NaCl, 1 mM EDTA) containing protease inhibitor (5 µg/ml leupeptin, 5 µg/ml pepstatin A, 5 µg/ml chymostatin (all of which from PEPTIDE INSTITUTE, Inc.)) was added in an amount (v/v) 10 times the amount of the collected cells. The cells were disrupted under ice-cooling condition using a glass homogenizer and centrifuged at 10,000 g for 20 minutes, and thereby soluble supernatant fraction and insoluble precipitates were obtained. The precipitates were suspended by the addition of RIPA-buffer (50 mM Tris-HCL (pH 8.0), 150 mM NaCl, 1% Nonidet P-40, 0.5% deoxycholic acid, 0.1% SDS) containing protease inhibitor (5 µg/ml leupeptin, 5 µg/ml pepstatin A, 5 µg/ml chymostatin) in the same volume as the volume of the previously added TNE-buffer, and subjected to ultrasonic homogenization for about 3 minutes to disperse the precipitates.

(6)-2: Analysis by Western Blotting

Approximately 20 µg of each of the proteins from the above-described soluble fraction and the proteins from insoluble fraction solubilized with the RIPA buffer that were both derived from the PANC-1 was used to perform electrophoresis on 2 to 15% acrylamide gradient gel. After electrophoresis, the proteins were transferred from the gel to a PVDF membrane. After the PVDF membrane was blocked, the membrane was reacted with HoAKs-1 antibody over night at 4° C. and subsequently at 37° C. for 1 hour. Then, the PVDF membrane was washed with PBS-T and added with a horseradish peroxidase (HRP)-conjugated goat antibody against a human antibody (1,000-fold dilution, CAPPEL) to react at 37° C. for 1 hour. Next, the PVDF membrane was washed with PBS-T and substances that reacted with the HoAKs-1 were detected with Western blotting luminol reagent (Santa Cruz Biotechnology).

The electrophoretic pattern of the proteins derived from the PANC-1 cell (Coomassie Brilliant Blue staining) and the result of Western blotting are shown in FIG. 5. It was found that the HoAKs-1 antibody exhibited reactivity to a single protein of approximately 55 kDa from the insoluble fraction (membrane fraction) of the homogenate of the pancreatic cancer cell line PANC-1.

(6)-3: Amino Acid Sequencing Analysis

Approximately 560 µg of the above-described insoluble fraction derived from PANC-1 was solubilized with the RIPA buffer and treated with Amersham Plus One 2-D Clean-Up kit, and then approximately 40 µg of the sample was subjected to two-dimensional electrophoresis. In the first dimension of electrophoresis, the sample was penetrated into ZOOM STRIP (pH 3-10NL) (Invitrogen) to carry out isoelectric focusing. In the second dimension, 10% acrylamide gel was used to carry out SDS-electrophoresis. Substance that reacted with HoAKs-1 was detected on the two-dimensional electrophoretic pattern in the same way as the above-described Western blotting. The two-dimensional electrophoresis was repeated thirteen times using the same kind of sample. The gel after electrophoresis was stained with Coomassie Brilliant Blue and 13 spots corresponding to the reactants of the HoAKs-1 antibody detected in the Western blotting were excised from the gel.

The excised gel sections were washed and added with Tris buffer (pH 8.5) containing lysyl-end peptidase to conduct overnight treatment at 35° C. Thereafter, the solution was subjected to reversed phase HPLC (TSKgel ODS-80Ts) to separate peptide fragments. Of the separated peptides, the fraction No. 58 was loaded onto the amino acid sequence analyzer (Procise 494 HT Protein Sequencing System), and thereby a peptide sequence from Val at its N terminal up to the twelfth residue was determined among mainly detected amino acid sequences. That sequence was VELQELNDRFAN (SEQ ID NO: 107) and found to conform to the internal sequences of various kinds of vimentins (Mol. Cell. Biol. Vol. 6, p3614-3620, 1986, GenBank Accession No. M14144) and desmins (Gene vol. 78, p243-254, 1989) as a result of homology research. Because vimentin and desmin are cytoskeletal filaments, the HoAKs-1 antibody was considered to be an antibody having reactivity to cytoskeletal filaments.

It was considered that the HoAKs-1 antibody exhibits morphological changes (FIG. 1) and anti-proliferative effects (FIGS. 2 and 3) on the tumor cells via a protein containing this amino acid sequence VELQELNDRFAN (SEQ ID NO: 107). Because the tumor cells exhibit morphological changes by adding the HoAKs-1 antibody in culture medium, this antigenic protein was predicted to exist on the membrane surface of the tumor cells.

(7) Cloning of a Gene Encoding Human Monoclonal Antibody HoAKs-1 and Determination of its Nucleotide Sequence Total RNA was prepared from the HoAKs-1 antibody-producing hybridoma using an RNeasy™ Protect Mini kit (QIAGEN). Reverse transcription reaction was performed using RNA PCR KIT (AMV) (TAKARA BIO INC.) and random 9mers as primers to synthesize cDNAs.

Based on the known sequence of a gene encoding antibody (J Mol Biol. vol. 222, pp581-597, 1991), for amplifying variable region of the heavy chain, a mixture of equal amounts of PCR primers (5' end-primers) including VH1 (SEQ ID NO: 1), VH2 (SEQ ID NO: 3), VH3 (SEQ ID NO: 5), VH4 (SEQ ID NO: 7), VH5 (SEQ ID NO: 9) and VH6 (SEQ ID NO: 11) each corresponding to the N-terminal amino acid sequences (SEQ ID NOS: 2, 4, 6, 8, 10 and 12) conserved in the frame 1 of variable region of the heavy chain of human antibodies and a mixture of equal amounts of PCR primers (3' end-primers) including JH1 (SEQ ID NO: 13), JH2 (SEQ ID NO: 15), JH3 (SEQ ID NO: 17) and JH4 (SEQ ID NO: 19) each corresponding to the C-terminal amino acid sequences (SEQ ID NOS:14, 16, 18 and 20) conserved in the frame 4 of variable region of the heavy chain of human antibodies were used as primers for PCR amplification.

A mixture of equal amounts of PCR primers (5' end-primers) including VK1 (SEQ ID NO: 21), VK2 (SEQ ID NO: 23), VK3 (SEQ ID NO: 25), VK4 (SEQ ID NO: 27), VK5 (SEQ ID NO: 29) and VK6 (SEQ ID NO: 31) each corresponding to the N-terminal amino acid sequences (SEQ ID NOS: 22, 24, 26, 28, 30, and 32) conserved in the frame 1 of variable region of κ chain of human antibodies and a mixture of equal amounts of PCR primers (3' end-primers) including JK1 (SEQ ID NO:

33), JK2 (SEQ ID NO: 35), JK3 (SEQ ID NO: 37), JK4 (SEQ ID NO: 39) and JK5 (SEQ ID NO: 41) each corresponding to the C-terminal amino acid sequences (SEQ ID NOS: 34, 36, 38, 40 and 42) conserved in the frame 4 of variable region of κ chain of human antibodies were used as primers for amplifying variable region of the κ chain.

A mixture of equal amounts of PCR primers (5' end-primers) including VL1 (SEQ ID NO: 43), VL2 (SEQ ID NO: 45), VL3 (SEQ ID NO: 47), VL4 (SEQ ID NO: 49), VL5 (SEQ ID NO: 51), VL6 (SEQ ID NO: 53) and VL7 (SEQ ID NO: 55) each corresponding to the N-terminal amino acid sequences (SEQ ID NOS: 44, 46, 48, 50, 52, 54 and 56) conserved in the frame 1 of variable region of λ chain of human antibodies and a mixture of equal amounts of PCR primers (3' end-primers) including JL1 (SEQ ID NO: 57), JL2 (SEQ ID NO: 59) and JL3 (SEQ ID NO: 61) each corresponding to the C-terminal amino acid sequences (SEQ ID NOS: 58, 60 and 62) conserved in the frame 4 of variable region of λ chain of human antibodies were used as primers for amplifying variable region of the λ chain.

PCR reaction was performed using Perkin Elmer Gene Amp PCR System 2400 and RNA PCR KIT (AMV) (TAKARA BIO INC.) according to the manufacturer's instructions. As a result, the light chain was amplified by PCR with the primers for the K chain but not amplified with the primers for the λ chain. Therefore, it was revealed that the light chain of the antibody produced by the hybridoma was a κ chain.

The amplified DNA fragments each encoding variable region of the heavy or light chain were purified using MinElute™ PCR Purification kit (QIAGEN). Next, using TOPO™ TA cloning kit (Invitrogen), the purified PCR products were ligated to pCR™2.1-TOPO™ cloning vector, and the obtained plasmids were used to transform *E. coli*. Appeared colonies were picked up and plasmids were isolated using QIAGEN Plasmid mini kit (QIAGEN), followed by digestion with EcoRI at 37° C. for 15 minutes and electrophoresis on 2% agarose gel to confirm the insertion of a DNA fragment of interest.

The nucleotide sequences of the inserted DNA fragments were analyzed for several colonies by CEQ 2000 DNA Analysis System (Beckman) using M13 primers. As a result, four sequences including HO9 (SEQ ID NO: 63), H12 (SEQ ID NO: 65), H27 (SEQ ID NO: 67) and H30 (SEQ ID NO: 69) were identified from the analysis of the heavy chain. Ten sequences including K30 (SEQ ID NO: 71), K31 (SEQ ID NO: 73), K32 (SEQ ID NO: 75), K35 (SEQ ID NO: 77), K39 (SEQ ID NO: 79), KMO5 (SEQ ID NO: 97), KMO6 (SEQ ID NO: 99), KMO26 (SEQ ID NO: 101), KMO36 (SEQ ID NO: 103) and KMO40 (SEQ ID NO: 105) were identified from the analysis of the κ chain. Of those sequences, HO9, H12, H27, H30, K30, K31, K32, K35 and K39 were considered to encode heavy and light chains of human antibody. By comparing those nucleotide sequences and the corresponding amino acid sequences (heavy chain: SEQ ID NOS: 64, 66 and 68; κ chain: SEQ ID NOS: 70, 72, 74, 76, 78 and 80), the nucleotide sequences of the variable regions (heavy chain: SEQ ID NO: 81; light chain: SEQ ID NO: 83) and the amino acid sequences (heavy chain: SEQ ID NO: 82; light chain: SEQ ID NO: 84) were determined for each of the heavy and light chains.

For the gene encoding HoAKs-1 antibody, a sequence of the 3'-region relative to the above-determined sequence was further determined. The amplification of the 3'-region of the heavy-chain gene was carried out by PCR using a 5'-side primer of primer VH3 (SEQ ID NO: 5) corresponding to the N-terminal amino acid sequence conserved in the frame 1 of variable region of the heavy chain of human antibodies, and a 3'-side primer of PCR primer IgMFOR (SEQ ID NO: 108) corresponding to the amino acid sequence of constant region of the heavy chain of human antibodies. The resulting PCR product was inserted into a plasmid in the same way as described above to determine the nucleotide sequence. As a result, a sequence composed of 57 nucleotides (SEQ ID NO: 110) which follows the above-described nucleotide sequence of variable region of the heavy chain (SEQ ID NO: 81) was determined. This nucleotide sequence was predicted to encode 19 amino acids (SEQ ID NO: 111). The nucleotide sequence of a gene encoding the heavy-chain of HoAKs-1 antibody including these 57 nucleotides and the predicted amino acid sequence are shown in SEQ ID NO: 118 and SEQ ID NO: 119, respectively. On the other hand, because these 57 nucleotides also contain the sequence encoding the constant region, the nucleotide sequence of the gene encoding the heavy chain of the HoAKs-1 antibody including only variable region (24 nucleotides) and the predicted amino acid sequence are shown in SEQ ID NO: 114 and SEQ ID NO: 115, respectively.

The amplification of a gene encoding the κ-chain of the HoAKs-1 antibody was carried out by PCR using a 5'-side primer of PCR primer VK4 (SEQ ID NO: 27) corresponding to the N-terminal amino acid sequence conserved in the frame 1 of variable region of the κ chain of human antibodies, and a 3'-side primer of PCR primer GKFOR (SEQ ID NO: 109) corresponding to the C-terminal amino acid sequence of constant region of κ chain of human antibodies. The resulting PCR product was inserted into a plasmid in the same way as described above to determine the nucleotide sequence. As a result, a sequence composed of 99 nucleotides (SEQ ID NO: 112) which follows the 3'-side of the above-described nucleotide sequence of variable region of the κ chain (SEQ ID NO: 83) was determined. This nucleotide sequence was predicted to encode 33 amino acids (SEQ ID NO: 113). The nucleotide sequence of the gene encoding the κ-chain of 1-HoAKs-1 antibody including these 99 nucleotides and the predicted amino acid sequence are shown in SEQ ID NO: 120 and SEQ ID NO: 121, respectively. On the other hand, because these 99 nucleotides also contain the sequence encoding the constant region, the nucleotide sequence of the gene encoding the κ chain of HoAKs-1 antibody including only variable region (24 nucleotides and the predicted amino acid sequence are shown in SEQ ID NO: 116 and SEQ ID NO: 117, respectively.

A boundary between the hypervariable region (CDR) and the framework was determined with reference to the literature of Kabat et. al. (Sequences of Proteins of Immunological Interest, fifth edition, National Institutes of Health, Bethesda, Md., 1991). As a result, the CDRs of the heavy chain were determined to be HCDR1 (nucleotide sequence: SEQ ID NO: 85, amino acid sequence: SEQ ID NO: 86), HCDR2 (nucleotide sequence: SEQ ID NO: 87, amino acid sequence: SEQ ID NO: 88), and HCDR3 (nucleotide sequence: SEQ ID NO: 89, amino acid sequence: SEQ ID NO: 90). The CDRs of the light chain were determined to be LCDR1 (nucleotide sequence: SEQ ID NO: 91, amino acid sequence: SEQ ID NO: 92), LCDR2 (nucleotide sequence: SEQ ID NO: 93, amino acid sequence: SEQ ID NO: 94), and LCDR3 (nucleotide sequence: SEQ ID NO: 95, amino acid sequence: SEQ ID NO: 96).

(8) Duration of Morphological Changes

Figure 6:
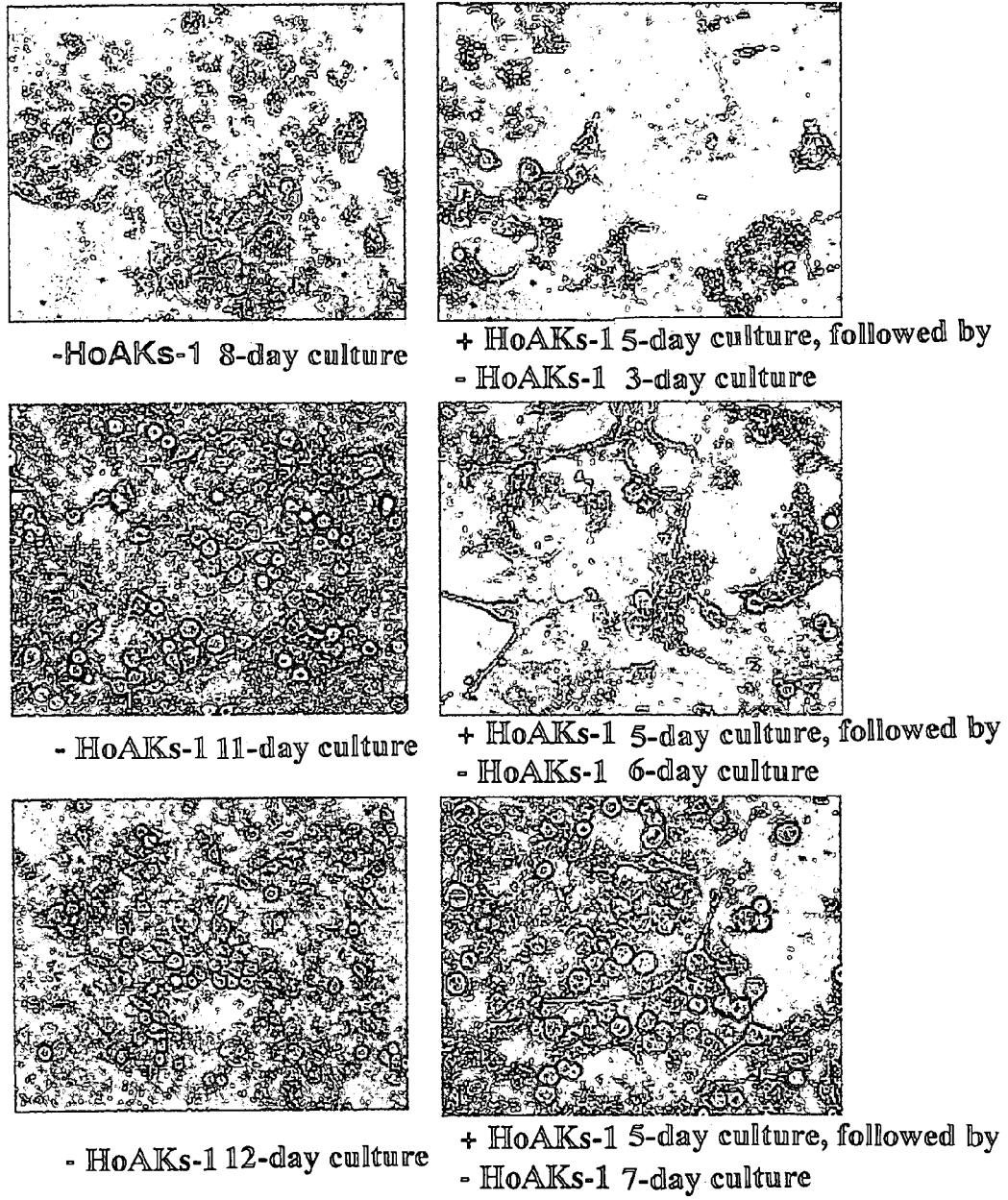
FIG. 6 is a diagram (photograph) showing a morphological change of each cell when the HoAKs-1 antibody is removed from culture medium after allowing the antibody to act on the cultured cancer cell line for a certain period of time.

The pancreatic cancer cell line PANC-1 in which morphological changes had been observed by the addition of the HoAKs-1 antibody was used to study the duration of its morphological changes. The pancreatic cancer cell line PANC-1 was cultured for 5 days at 37° C. under 5% $CO_2$ in the presence of approximately 100 μg/ml of the HoAKs-1 antibody, and then, culture medium was replaced with culture medium free from the HoAKs-1 antibody and cultured for additional 7 days. The microscopic images of the morphology of the cells on 3rd, 6th and 7th days post-removal of the HoAKs-1 antibody are shown in FIG. 6. Morphological changes of the PANC-1 cell caused by the HoAKs-1 antibody were continuously observed for a long term even after the removal of the antibody.

(9) Binding of HoAKs-1 Antibody to Surfaces of Living Cancer Cells

Figure 7:
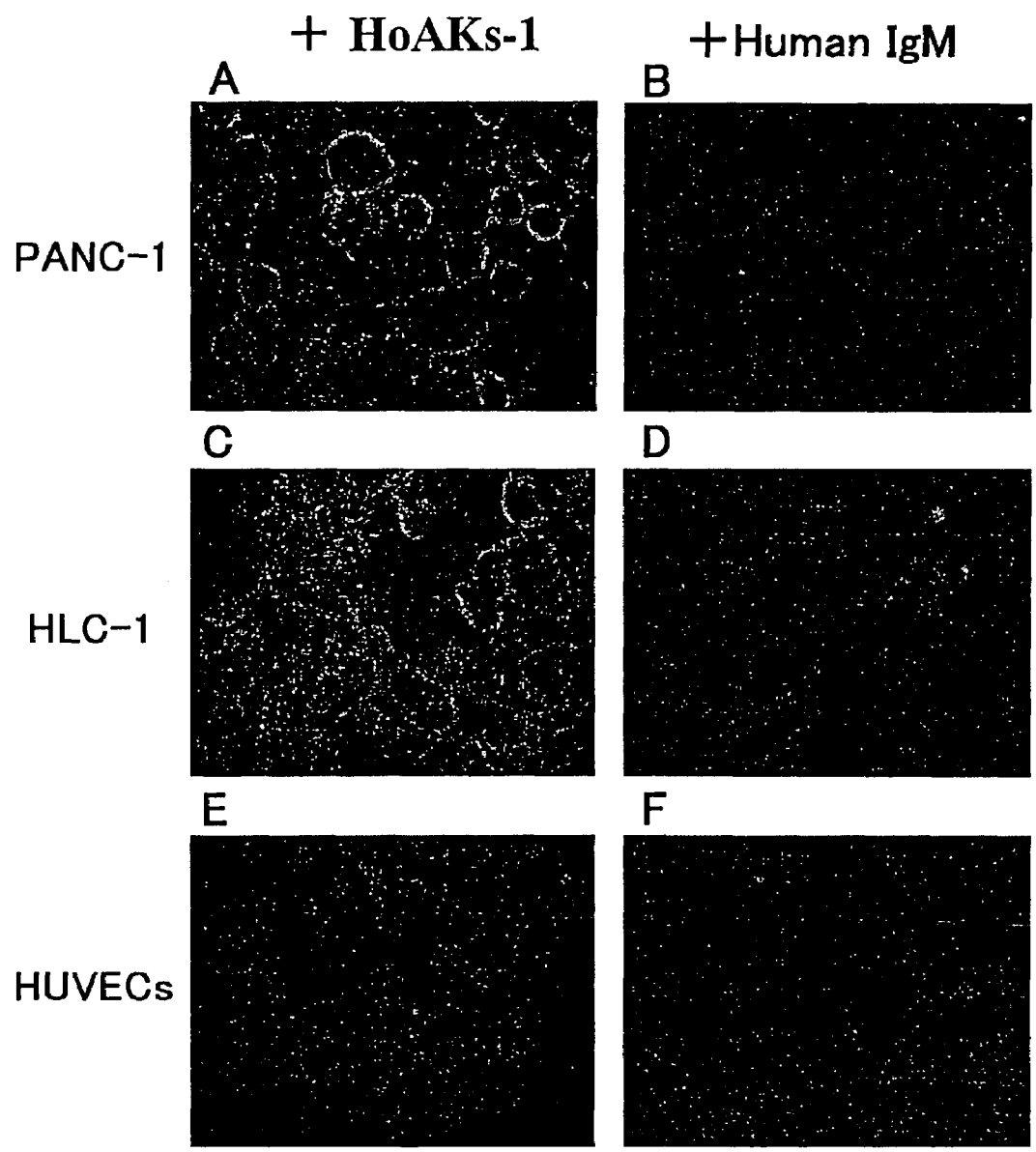
FIG. 7 is a diagram (photograph) showing the binding activity of the HoAKs-1 antibody to the surface of each living cancer cell.

The pancreatic cancer cell line PANC-1, the human lung cancer cell line HLC-1 and the human vascular endothelial cells HUVECs were seeded on a 96-well plate (3603, available from Corning Inc.) and cultured at 37° C. under 5% $CO_2$ for 1 day. The plate was then added with a solution containing 50 μg/ml of the biotinylated HoAKs-1 antibody described in Example (3)-2 and 0.05% sodium azide, and allowed to react at room temperature for 60 minutes. After the removal of the antibody solution, a solution containing 20 nM of Qdot™565 streptavidin-label (available from Quantm Dot Corporation) and 0.05% sodium azide was added and incubated at room temperature for 30 minutes. After removal of the solution, PBS containing 0.05% sodium azide was added and cells were observed with a confocal fluorescence microscope (CSU10, available from Yokogawa Electric Corporation). The binding of the HoAKs-1 antibody to the surface of each living cell is shown in FIG. 7. The HoAKs-1 antibody exhibited binding to the surfaces of the living cells of the PANC-1 and the HLC-1 (FIGS. 7-A and 7-C), but no binding to the HUVEC cells (FIG. 7-E). The human IgM antibody used as a control exhibited no binding to all of the cells (FIGS. 7-B, 7-D, and 7-F).

(10) Preparation of a Mouse Monoclonal Antibody Against Approximately 55 kDa Protein Derived from Pancreatic Cancer Cell Line PANC-1

(10)-1: Immunization of Mouse and Cell Fusion

The proteins in the insoluble fraction after solubilization with the RIPA buffer were prepared from the homogenate of the PANC-1 cell in the same way as in Example (6)-1. Approximately 180 μg of the proteins were subjected to electrophoresis on 10% acrylamide gel. After electrophoresis, the gel was stained with Coomassie Brilliant Blue and the band corresponding to an approximately 55 kDa protein to which the HoAKs-1 antibody reacted was excised.

The excised gel was fractured and mixed with 0.2 ml of Freund's complete adjuvant (DIFCO LABORATORIES). The mixture was injected intraperitoneally into a mouse (Balb/cA Jcl, 6-week old, female, CLEA JAPAN) to carry out primary immunization. After additional two weeks, the same kind of gel was mixed with incomplete adjuvant and the preparation as prepared as described above was used to immunize the mouse again. After 4 days, the spleen was extracted from the same mouse. Lymphocytes were prepared ($2.4 \times 10^8$ cells) and used to fuse to mouse myeloma cells P3U1s according to a standard method (Experimental Manual for Monoclonal Antibody, published by Kodansha Scientific). The fused cells were suspended in the culture medium D (eRDF+50 μg/ml gentamicin+10% FCS) supplemented with usual concentrations of HAT. The suspension was dispensed on a 96-well plate and cultured at 37° C. in a $CO_2$ incubator. After approximately 2 weeks from cell fusion, the appearance of hybridomas was detected. Using the culture supernatant, reactivity to the approximately 55 kDa protein was detected by Western blotting and thereby a hybridoma of interest was selected.

(10)-2: Detection of Reactivity to Approximately 55 kDa Protein

Approximately 4 mg of the proteins in the insoluble fraction after solubilization of the homogenate of the PANC-1 cell with the RIPA buffer was used for electrophoresis on 10% acrylamide gel. The proteins were transferred from the gel to a PVDF membrane and the membrane was blocked. The culture supernatant was collected from the well of the 96-well plate as described in Example (10)-1 and used to react with the transferred PVDF membrane at 37° C. for 1 hour. The PVDF membrane was washed with PBS-T. The resulting PVDF membrane was added with a HRP-conjugated goat antibody against a mouse antibody (1,000-fold dilution, CAPPEL) and further reacted at 37° C. for 1 hour. Next, the PVDF membrane was washed with PBS-T and the reactivity of the culture supernatant to the approximately 55 kDa protein was determined using Konica Immunostain HRP-1000 (Konica). Cloning of hybridoma was performed by limiting dilution from the wells in which reactivity was detected, and thereby hybridoma cell lines 2F6-1 and 3F9-1 were established.

(11) Binding of an Anti-55 kDa Mouse Monoclonal Antibody to Surfaces of Living Cancer Cells (11)-1: Purification and Labeling of the Anti-55 kDa Mouse Monoclonal Antibody The hybridoma cell lines 2F6-1 and 3F9-1 established in Example (10)-2 were cultured. The culture supernatant of each of the hybridoma cell lines was collected and loaded onto the PROSEP-A to purify the antibody. Each monoclonal antibody was found to be IgM by SDS-PAGE analysis. After each of the purified antibodies was biotinylated using a biotinylation reagent according to the manufacturer's instructions, the labeled antibody was separated from free biotin by a gel filtration method.

(11)-2: Binding of the Antibody to Surface of Living Cancer Cells

Figure 8:
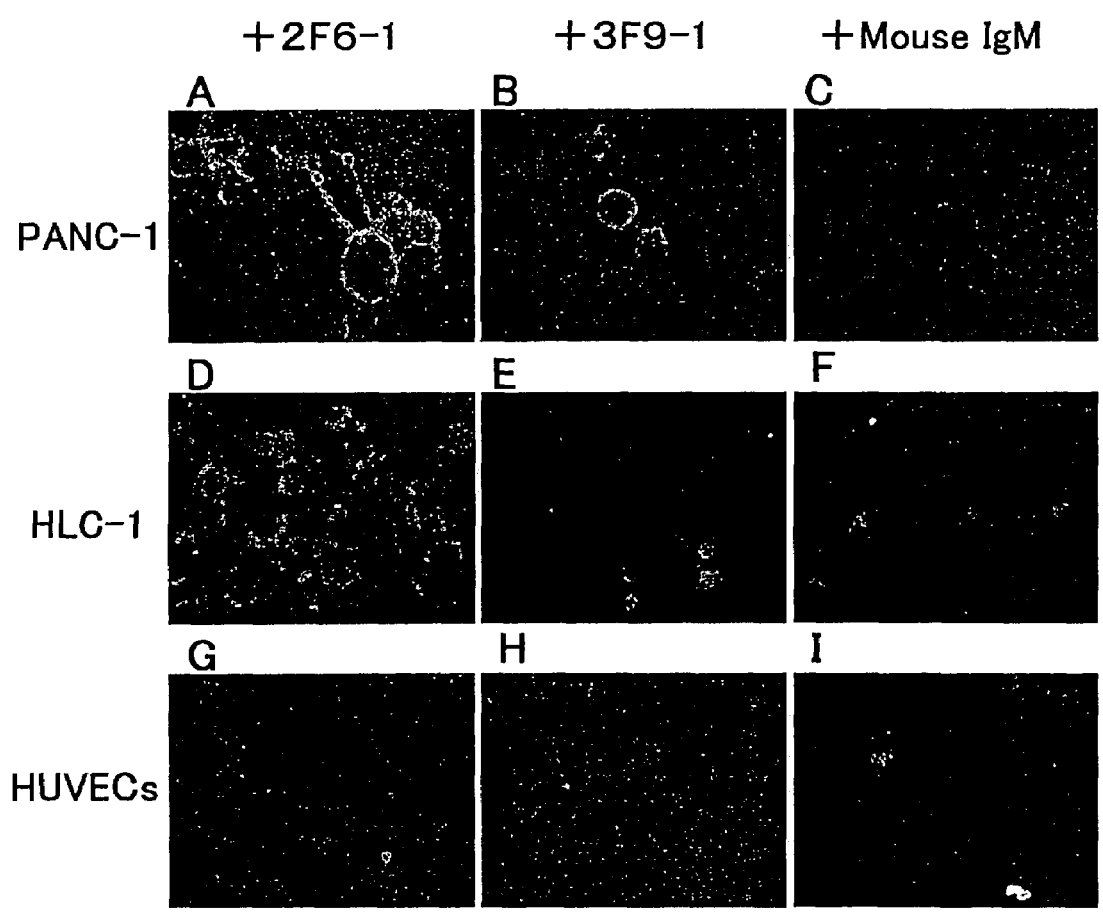
FIG. 8 is a diagram (photograph) showing the binding activity of an anti-55 kDa mouse monoclonal antibody to the surface of each living cancer cell.

The pancreatic cancer cell line PANC-1, the lung cancer cell line HLC-1, and the vascular endothelial cells HUVECs were seeded on a 96-well plate (3603, Corning) and cultured at 37° C. under 5% $CO_2$ for 1 day in the same way as in Example (9). The plate was then added with a solution containing 50 μg/ml of the biotinylated anti-55 kDa mouse monoclonal antibody described in Example (11)–1 and 0.05% sodium azide, and allowed to react at room temperature for 60 minutes. After the removal of the antibody solution, a solution containing 20 nM of Qdot™565 streptavidin-labeled (Quantm Dot Corporation) and 0.05% sodium azide was added and reacted at room temperature for 30 minutes. After removal of the solution, PBS containing 0.05% sodium azide was added and cells were observed with a confocal fluorescence microscope (CSU10, Yokogawa Electric Corporation). The binding of the anti-55 kDa mouse monoclonal antibody to the surface of each living cell is shown in FIG. 8. The antibody derived from 2F6-1 and 3F9-1 exhibited binding to the surfaces of the living cells of the PANC-1 and the HLC-1 like HoAKs-1 antibody described in Example (9) (FIGS. 8-A, 8-B, 8-D, and 8-E), but exhibited no binding to the HUVECs cells (FIGS. 8-G and 8-H).

(12) Reactivity of Anti-Vimentin Antibody and Anti-Desmin Antibody to Approximately 55 kDa Protein Evaluated by Western Blotting The proteins in the insoluble fraction after solubilization of the homogenate of the PANC-1 cells with the RIPA buffer was loaded onto the lanes of 10% acrylamide gel at approximately 10 μg/lane for electrophoresis. The proteins were transferred from the gel to a PVDF membrane and the membrane was blocked. An anti-vimentin mouse monoclonal antibody (sc-6260, Santa Cruz Biotechnology) or an anti-desmin goat antibody (sc-7559,Santa Cruz Biotechnology) was reacted with the PVDF membrane at 37° C. for 1 hour. The PVDF membrane was then washed with PBS-T and added with a HRP-conjugated goat antibody against a mouse antibody (1,000-fold dilution, CAPPEL) or HRP-conjugated mouse antibody against a goat antibody (1,000-fold dilution), and further reacted at 37° C. for 1 hour. Next, the PVDF membrane was washed with PBS-T and substances that reacted to the antibodies were detected using Western blotting luminol reagent. Although the anti-vimentin antibody exhibited reactivity to the approximately 55 kDa protein, the anti-desmin antibody exhibited no reactivity.

Those results have demonstrated that the approximately 55 kDa protein derived from the PANC-1 that was recognized by the HoAKs-1 antibody is determined to be vimentin and that there exists an antibody having binding ability to the surface of the living cancer cells among the antibodies having reactivity to the protein.

(13) Preparation of γ-HoA. (Recombinant HoAKs-1 Antibody)

(13-1) Preparation of cDNA and Cloning of a DNA Fragment Encoding a Variable Region of HoAKs-1

The preparation of cDNA from the total RNA (described in Example (7)) and the PCR reaction were carried out using Perkin Elmer Gene Amp PCR System 2400 and Thermo-Script™ RT-PCR Systems plus platinum Tag DNA polymerase High Fidelity (Invitrogen) according to the manufacturer's instructions. Random hexamers supplied in the kit were used as primers for preparing the cDNA of the heavy chain. P1 (SEQ ID NO: 122) was used as a primer for preparing the cDNA of the κ chain.

For amplification of the variable regions of the heavy chain and the κ chain, primers having a restriction enzyme site for insertion into an expression plasmid were used. For amplification of the variable region of the heavy chain, primer P2 (SEQ ID NO: 123) containing a HindIII site and a signal sequence at the 5' terminus and primer P3 (SEQ ID NO: 124) containing a NheI site at the 3' side were used. For amplification of the variable region of the κ chain, primer P4 (SEQ ID NO: 125) containing a HindIII site and a signal sequence at the 5' side and primer P5 (SEQ ID NO: 126) containing a BsiWI site at the 3' side were used.

The DNA fragment of the variable region of each of the amplified heavy and κ chains was purified using QIAquick™ PCR Purification Kit (QIAGEN). Next, for insertion into the expression vector, the DNA fragments were digested with restriction enzymes. The fragment of the heavy chain was digested with HindIII and NheI at 37° C. for 2 hours. The DNA fragment of the κ chain was initially digested with BsiWI at 37° C. for 2 hours and then purified with the QIAquick™ PCR Purification Kit (QIAGEN), followed by subsequent digestion with HindIII at 37° C. for 2 hours. The digested DNA fragments were subjected to 1.5% agarose electrophoresis to purify a DNA fragment of interest using a QIAquick™ Gel Extraction Kit (QIAGEN).

(13-2) Digestion of Expression Plasmid and Preparation of Plasmid Fragment

For expressing the human IgG1-type recombinant antibody of the HoAKs-1, pEX-G1-WLpHy containing the sequence of the constant region of the heavy chain was used as a plasmid for expressing the heavy chain, and pKS-κ'-Hind-5 containing the sequence of the constant region of the κ chain was used as a plasmid for expressing the κ chain. The pEX-G1-WLpHy was digested with HindIII and SpeI at 37° C. for 2 hours. The pKS-κ'-Hind-5 was digested with Asp718 at 37° C. for 2 hours and then purified with a QIAquick™ PCR Purification Kit (QIAGEN), followed by subsequent digestion with HindIII at 37° C. for 2 hours. The digested fragments were subjected to 0.8% agarose electrophoresis to purify a fragment of interest using QIAquick™ Gel Extraction Kit (QIAGEN).

(13-3) Insertion of HoAKs-1 Variable Region into the Expression Plasmid

The DNA fragment containing heavy chain of the variable region of the HoAKs-1 obtained by the above-described method was inserted into the digested expression plasmid pEX-G1-WLpHy using Ligation Kit Ver. 2.1 (TAKARA BIO INC.) according to the manufacturer's instructions, and the obtained plasmid was used to transform E. coli DH5α-T1 (Invitrogen) according to the manufacturer's instructions. The appeared colonies were picked up and the plasmid was purified using QIAprep™ Spin Miniprep Kit (QIAGEN). The plasmid containing the nucleotide sequence of the heavy chain was digested with NdeI at 37° C. for 1 hour and subjected to 1.5% agarose electrophoresis, and thereby a desired plasmid pEX-HoAKs-H was obtained. For the obtained plasmid, the nucleotide sequence was analyzed using P6 primer (SEQ ID NO: 127) at the 5' side and P7 primer (SEQ ID NO: 128) at the 3' side. The nucleotide sequence of the structural gene of the heavy-chain of the HoAKs-1 recombinant antibody is shown in SEQ ID NO: 129.

On the other hand, the DNA fragment containing the variable region of the κ chain of the HoAKs-1 was inserted into the digested expression plasmid pKS-κ'-Hind-5 using Ligation Kit Ver. 2.1 (TAKARA BIO INC.) according to the manufacturer's instructions, and the obtained plasmid was used to transform E. coli DH5α-T1 (Invitrogen). The appeared colonies were picked up and the plasmid was purified using QIAprep™ Spin Miniprep Kit (QIAGEN). The plasmid containing the nucleotide sequence of the κ chain was digested with BsiWI at 37° C. for 1 hour and subjected to 1.5% agarose electrophoresis, and thereby a desired plasmid pKS-HoAKs-K was obtained. For the obtained plasmid, the nucleotide sequence was confirmed using primer P6 at the 5' side and primer P1 at the 3' side. The nucleotide sequence of the structural gene of the κ-chain of the HoAKs-1 recombinant antibody is shown in SEQ ID NO: 131.

(13-3) Insertion of a Gene Encoding Heavy Chain of HoAKs-1 into a Plasmid Containing HoAKs-1 κ Chain For ligating the heavy chain and κ chain of HoAKs-1 on one plasmid, the plasmids obtained above were digested with restriction enzymes. The pEX-HoAKs-H was digested with NheI at 37° C. for 2 hours and the pKS-HoAKs-K was digested with NheI and SpeI at 37° C. for 2 hours. The resulting fragments were purified using QIAquick™ PCR Purification Kit (QIAGEN). The fragments were ligated with each other using Ligation Kit Ver. 2.1 (TAKARA BIO INC.) according to the manufacturer's instructions, and the obtained plasmid was used to transform E. coli DH5α-T1 (Invitrogen). The appeared colonies were picked up and the plasmid was purified using QIAprep™ Spin Miniprep Kit (QIAGEN). The resulting plasmid was digested with NheI at 37° C. for 30 minutes and subjected to 0.8% agarose electrophoresis, and thereby a desired plasmid pEX-HoAKs-HK was obtained.

(13-4) Construction of γ-HoA.-Expressing Plasmid

The pEX-HoAKs-HK obtained above was ligated with a plasmid pSV2dhfr" containing a dhfr gene to construct a plasmid for expressing γ-HoA. The pEX-HoAKs-HK was first digested with BamHI and NheI at 37° C. for 2 hours and then subjected to 0.8% agarose electrophoresis, followed by purification of a DNA fragment of interest using QIAquick™ Gel Extraction Kit (QIAGEN). The pSV2dhfr" was digested with BamHI and NheI at 37° C. for 2 hours and then treated at 65° C. for 15 minutes by the addition of Alkaline Phosphatase (TAKARA BIO INC.), followed by purification using QIAquick™ PCR Purification Kit (QIAGEN). Thereafter, the resulting mixture was subjected to 0.8% agarose electrophoresis, and a DNA fragment of interest was purified using QIAquick™ Gel Extraction Kit (QIAGEN).

The fragments were ligated with each other using Ligation Kit Ver. 2.1 (TAKARA BIO INC.) according to the manufacturer's instructions, and the obtained plasmid was used to transform *E. coli* DH5α-T1 (Invitrogen). The appeared colonies were picked up and the plasmid was purified using QIAprep™ Spin Miniprep Kit (QIAGEN). The resulting plasmid was digested with NdeI at 37° C. for 1 hour and subjected to 1.5% agarose electrophoresis, and thereby a desired plasmid pEX-HoAKs-HK/pSV2dhfr" for expression of recombinant antibody was obtained.

(13-5) Preparation of γ-HoA.-Producing Cells

CHO (DG325) cell lines culturable in a serum-free medium were used as cell lines for producing γ-HoA. The CHOs (DG325) were diluted in CHO-S-SFMII (GIBCO) at $1 \times 10^6$ cells/ml. Thereafter, 2 μg of pEX-HoAKs-HK/pSV2dhft" DNA and 6 μL of FuGENE™ 6 transfection reagent (Roche) were mixed to transfect the CHOs (DG325) according to the manufacturer's instructions. At 5 hours after transfection, EX-CELL325-PF (Nichirei) was added. After two-day culture, 400 μg/ml of G418 Sulfate (Promega) and 0, 25, or 50 nM of methotrexate (Sigma) were added to the medium for selection and culture was further conducted, and thereby γ-HoA.-producing cells were obtained.

(13-6) Measurement of Production Amount of Antibody Using ELISA Assay

The amount of γ-HoA. produced by the cells was measured by sandwich ELISA assay. At first, a rabbit anti-human immunoglobulin antibody (CAPPEL) was diluted to 50 μg/ml with the solution 1 (PBS) and added to a 96-well flexible plate (FALCON) at 50 μL/well to treat at 37° C. for 2 hours. The solution in the wells was then discarded and the solution 2 (0.1% Gelatin/PBS/0.05% Tween 20) was added to the wells at 200 μL/well to react at 4° C. for 16 or more hours. The solution in each of the wells was then discarded and the plate was added with 50 μL/well of the culture supernatant diluted with the solution 2 to incubate at 4° C. for 16 or more hours. After reaction, the solution in each of the wells was discarded. After washed five times with a solution 3 (PBS/0.05% Tween 20), the plate was added with 50 μL/well of a HRP-labeled rabbit anti-human immunoglobulin antibody (CAPPEL) which had been diluted 1,000-fold with the solution 2, and reacted at 37° C. for 1 hour. The solution in each of the wells was discarded. After washing five times with PBS/0.05% Tween 20, the plate was added with 50 μL/well of substrate solution (light-shaded and adjusted before use) in which an o-phenylenediamine tablet (Wako Pure Chemical Industries) had been dissolved in 50 mM citrate buffer (pH 5.0) and supplemented with hydrogen peroxide solution. After the plate was reacted at room temperature for about 3 minutes for color development, 1 N $H_2SO_4$ was added at 50 μL/well to terminate the reaction. Absorbance A1 at L1=495 nm and absorbance A2 at L2=650 nm were measured with a multi-plate reader SPECTRA MAX250 (Molecular Devices), and the value of "A1-A2" was calculated. Human IgG1κ (CAPPEL) was diluted and used as a standard solution. A calibration curve was made to calculate the amount of the antibodies in the culture supernatant. From the calculated result, a cell having the largest amount of the antibody production was selected and used for producing γ-HoA.

(13-7) Purification of γ-HoA.

The γ-HoA.-producing cell line obtained above was cultured in EX-CELL325-PF (Nichirei) supplemented with G418 Sulfate (Promega) and methotrexate (Sigma) to obtain a culture medium containing γ-HoA. Next, the culture medium was loaded onto the PROSEP-A for adsorbing the γ-HoA. on it. The adsorbedγ-HoA. was then eluted and thereby the γ-HoA. was purified. It was confirmed that the γ-HoA. was a pure IgG by SDS-PAGE (not shown).

(14) Detection of Reactivity of γ-HoA. to Approximately 55 kDa Protein Derived from Pancreatic Cancer Cell Line PANC-1

Each 10 μg of the proteins in the insoluble fraction after solubilization of the homogenate of the PANC-1 cell with the RIPA buffer was subjected to electrophoresis on 10% acrylamide gel. The protein was transferred from the gel to a PVDF membrane and the membrane was blocked. The transferred PVDF membrane was reacted with the purified γ-HoA. described in Example (13-7) at 37° C. for 1 hour. The PVDF membrane was washed with PBS-T. The resulting PVDF membrane was added with an HRP-conjugated goat antibody against a human antibody (1,000-fold dilution, CAPPEL) and further reacted at 37° C. for 1 hour. Next, the PVDF membrane was washed with PBS-T. The reactivity of the γ-HoA. to the approximately 55 kDa protein was detected by using Western blotting luminol reagent (Santa Cruz Biotechnology), which revealed that the γ-HoA. had reactivity to the approximately 55 kDa protein like the HoAKs-1 antibody.

(15) Binding of γ-HoA. to Surfaces of Living Cancer Cells

Figure 9:
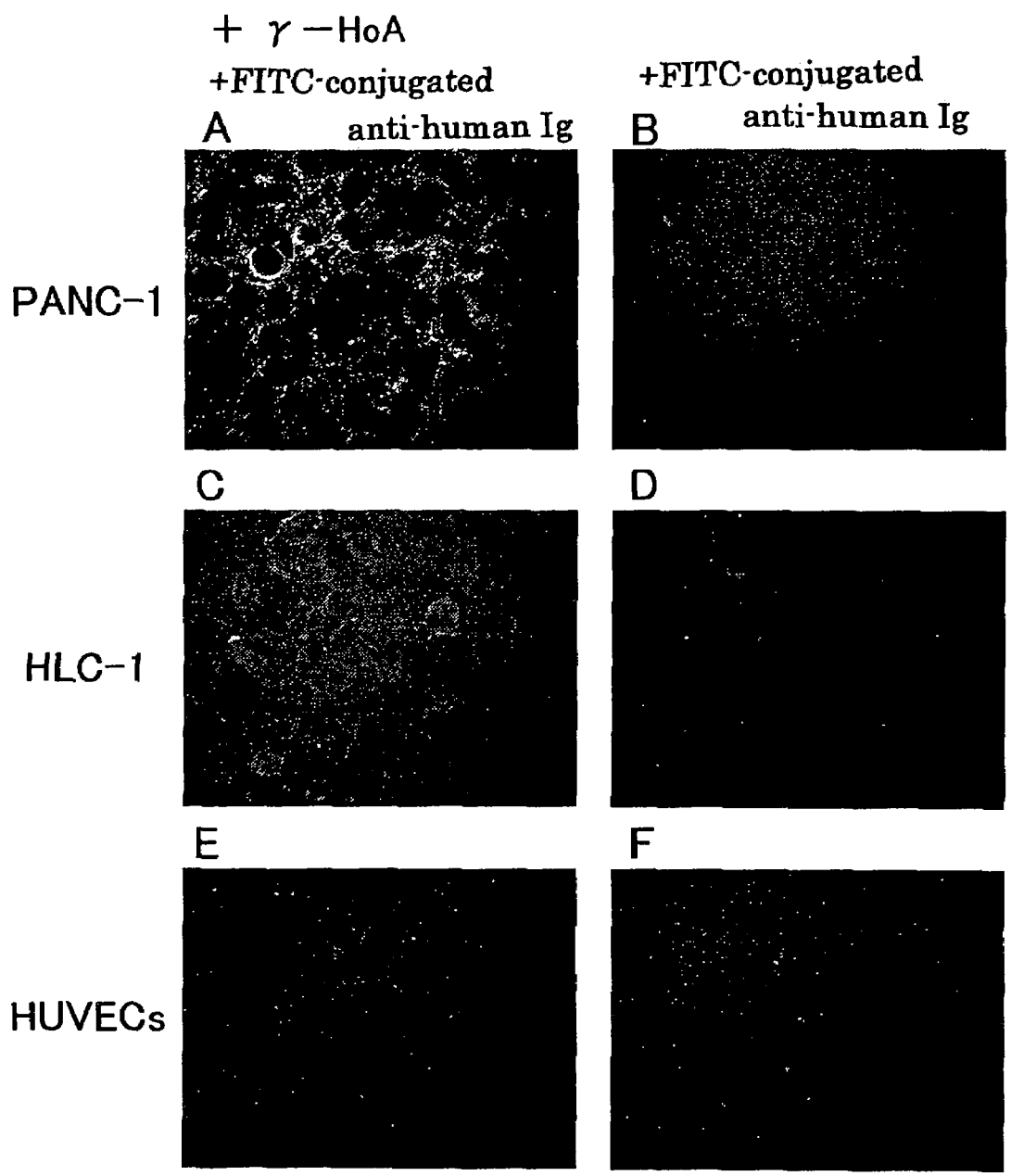
FIG. 9 is a diagram (photograph) showing the binding activity of γ-HoA. antibody to the surface of each living cancer cell.

The pancreatic cancer cell line PANC-1, the lung cancer cell line HLC-1 and the vascular endothelial cells HUVECs were seeded on a 96-well plate (3603, Corning) and cultured at 37° C. under 5% $CO_2$ for 1 day. The plate was then added with a solution containing the purified γ-HoA. described in Example (13)-7 and 0.05% sodium azide, and reacted at room temperature for 60 minutes. After the removal of the γ-HoA. solution, the plate was added with a solution containing FITC-conjugated goat antibody against a human antibody diluted 20-fold (CAPPEL) and 0.05% sodium azide and reacted at room temperature for 30 minutes. After removal of the solution, PBS containing 0.05% sodium azide was added and cells were observed with a confocal fluorescence microscope (CSU10, Yokogawa Electric Corporation). The binding of the antibody to the surface of each living cell is shown in FIG. 9. The γ-HoA. exhibited binding to the surfaces of the living cells of the PANC-1 and the HLC-1 (FIGS. 9-A and 9-C), but no binding to the HUVEC cells (FIG. 9-E), like the HoAKs-1 antibody described in Example (9).

INDUSTRIAL APPLICABILITY

By using a monoclonal antibody obtained in the present invention, an anti-cancer drug that selectively attacks cancer tissues, particularly non-small cell lung cancer, pancreatic cancer or gastric cancer can be provided. Moreover, when the human monoclonal antibody of the present invention is used, an anti-cancer drug capable of continuous administration with reduced side effects can be provided.

---

The invention claimed is:

1. An isolated monoclonal antibody which specifically binds human vimentin and which has a heavy chain and a light chain, wherein the variable region of the heavy chain of said the monoclonal antibody comprises the amino acid sequences of SEQ ID NOS: 86, 88 and 90, and wherein the variable region of the light chain of the monoclonal antibody comprises the amino acid sequences of SEQ ID NOS: 92, 94 and 96.

2. The monoclonal antibody according to claim 1, wherein the variable region of the heavy chain comprises the amino acid sequence of SEQ ID NO: 82.

3. The monoclonal antibody according to claim 1, wherein the variable region of the heavy chain comprises the amino acid sequence of SEQ ID NO: 115.

4. The monoclonal antibody according to claim 1, wherein the variable region of the light chain comprises the amino acid sequence of SEQ ID NO: 84.

5. The monoclonal antibody according to claim 1, wherein the variable region of the light chain comprises the amino acid sequence of SEQ ID NO: 117.

6. The monoclonal antibody according to claim 1, wherein the variable region of the heavy chain contains the amino acid sequence of SEQ ID NO: 82, and the variable region of the light chain comprises the amino acid sequence of SEQ ID NO: 84.

7. The monoclonal antibody according to claim 1, wherein the variable region of the heavy chain comprises the amino acid sequence of SEQ ID NO: 115, and the variable region of the light chain comprises an the amino acid sequence of SEQ ID NO: 117.

8. The monoclonal antibody according to claim 1, wherein said monoclonal antibody is a human antibody.

9. An isolated DNA which encodes the monoclonal antibody according to claim 1.

10. The DNA according to claim 9, wherein the variable region of the heavy chain of the monoclonal antibody is encoded by a nucleotide sequence comprising SEQ ID NOS: 85, 87 and 89, and a region that encodes the variable region of the light chain of the monoclonal antibody is encoded by a nucleotide sequence comprising SEQ ID NOS: 91, 93 and 95.

11. The DNA according to claim 9, wherein the variable region of the heavy chain of the monoclonal antibody is encoded by a nucleotide sequence comprising SEQ ID NO: 81, and the variable region of the light chain of the monoclonal antibody is encoded by a nucleotide sequence comprising SEQ ID NO: 83.

12. The DNA according to claim 9, wherein the variable region of the heavy chain of the monoclonal antibody is encoded by a nucleotide sequence comprising SEQ ID NO: 114, and the variable region of the light chain of the monoclonal antibody is encoded by a nucleotide sequence comprising SEQ ID NO: 116.

13. An isolated recombinant vector comprising the DNA according to claim 9.

14. An isolated transformant, comprising the recombinant vector according to claim 13.

15. A pharmaceutical composition, comprising the monoclonal antibody according to claim 1.

16. A diagnostic reagent, which comprises the monoclonal antibody according to claim 1.

* * * * *